US011969465B2

(12) United States Patent
McLeod et al.

(10) Patent No.: US 11,969,465 B2
(45) Date of Patent: Apr. 30, 2024

(54) TOXOPLASMA GONDII VACCINES AND THEIR USE

(71) Applicants: Alpha-O Peptides AG, Riehen (CH); Emergent Travel Health Inc., Redwood City, CA (US)

(72) Inventors: Rima McLeod, Chicago, IL (US); Kamal El Bissati, Chicago, IL (US); Ying Zhou, Chicago, IL (US); Jeff Alexander, Redwood City, CA (US); Steve Reed, Seattle, WA (US); Peter Burkhard, Riehen (CH); Mariane Melo, Cambridge, MA (US); Darrel Irvine, Cambridge, MA (US); Ron Weiss, Cambridge, MA (US); Yuan Zhang, Cambridge, MA (US)

(73) Assignee: EMERGENT TRAVEL HEALTH INC., Redwood City, CA (US)

( * ) Notice: Subject to any disclaimer, the term of this patent is extended or adjusted under 35 U.S.C. 154(b) by 0 days.

(21) Appl. No.: 17/692,333

(22) Filed: Mar. 11, 2022

(65) Prior Publication Data
US 2022/0202921 A1 Jun. 30, 2022

Related U.S. Application Data

(63) Continuation of application No. 16/892,083, filed on Jun. 3, 2020, now abandoned, which is a continuation of application No. 16/094,394, filed as application No. PCT/US2017/027675 on Apr. 14, 2017, now abandoned.

(60) Provisional application No. 62/324,225, filed on Apr. 18, 2016.

(51) Int. Cl.
*A61K 39/002* (2006.01)
*A61K 9/00* (2006.01)
*A61K 39/00* (2006.01)
*A61K 39/012* (2006.01)
*A61P 33/02* (2006.01)

(52) U.S. Cl.
CPC .......... *A61K 39/002* (2013.01); *A61K 9/0009* (2013.01); *A61K 9/0019* (2013.01); *A61K 39/012* (2013.01); *A61P 33/02* (2018.01); A61K 2039/55566 (2013.01); A61K 2039/57 (2013.01); A61K 2039/70 (2013.01); C07K 2319/00 (2013.01)

(58) Field of Classification Search
CPC .... A61K 39/00; A61K 9/0009; A61K 9/0019; A61K 9/012; A61K 2039/55566; A61K 2039/57; A61K 2039/70; A61P 33/02; C07K 2319/00
See application file for complete search history.

(56) References Cited

U.S. PATENT DOCUMENTS

2002/0141975 A1    10/2002    Olmsted et al.
2009/0293148 A1    11/2009    Ren et al.

FOREIGN PATENT DOCUMENTS

| WO | 1992010578 | 6/1992 |
| WO | 1997/027300 | 7/1997 |
| WO | 2012061599 | 5/2012 |
| WO | 2014/163684 | 10/2014 |

OTHER PUBLICATIONS

The International Search Report (ISR) with Written Opinion for PCT/US2017/027675 dated Jun. 15, 2017, pp. 1-14.
Bagaev A. V. i dr. Vliyanie TLR-agonistov na ekspressiu v antigenprezentiruuschikh kletkakh tselevogo belka-antigena, zakodirovannogo v adenovirusnom vektore. Immunologiya, 2015, tom 36, c. 188-189.
Coler R.N. et al. "Development and characterization of synthetic glucopyranosyl lipid adjuvant system as a vaccine adjuvant" PloS one, 2011,6 (I):e16333, p. 1-11, especially, abstract.
Greenspan et al. (Nature Biotechnology 7: 936-937, 1999).

*Primary Examiner* — Robert A Zeman
(74) *Attorney, Agent, or Firm* — McDonnell Boehnen Hulbert & Berghoff LLP

(57) ABSTRACT

Disclosed herein are polynucleotides encoding multi-epitope polypeptides and assemblies thereof, and their use for treating or limiting *Toxoplasma gondii* infection.

9 Claims, 19 Drawing Sheets

Specification includes a Sequence Listing.

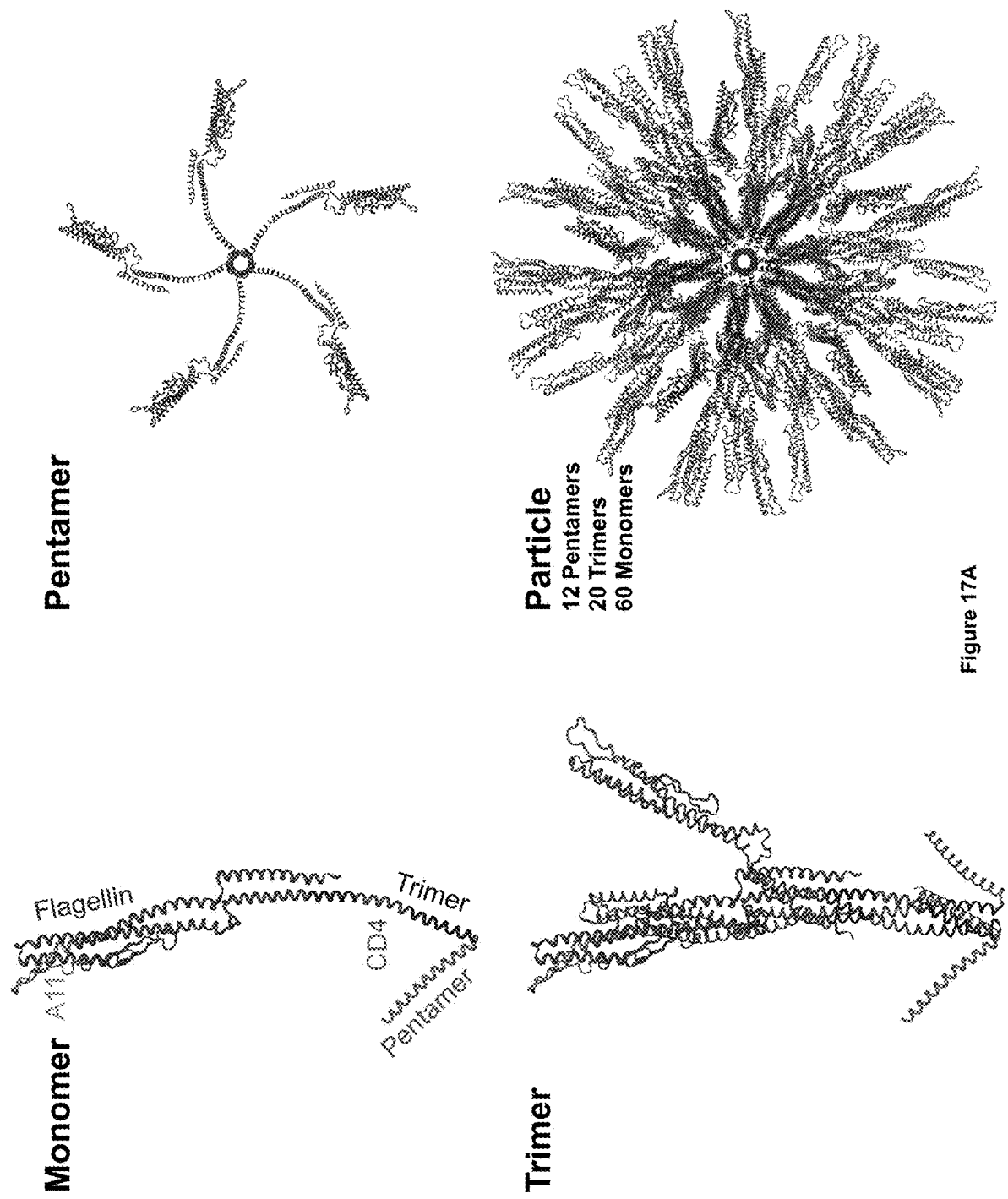

TOXOPLASMA GONDII VACCINES AND THEIR USE

CROSS REFERENCE

This application is a Continuation of U.S. patent application Ser. No. 16/892,083, filed on Jun. 3, 2020, which is a Continuation of U.S. patent application Ser. No. 16/094,394, filed on Oct. 17, 2018, which is a U.S. national phase of International Application No. PCT/US2017/027675, filed on Apr. 14, 2017, which claims priority to U.S. Provisional Application No. 62/324,225, filed Apr. 18, 2016, both of which are incorporated by reference herein in their entirety.

STATEMENT REGARDING FEDERALLY SPONSORED RESEARCH

This invention was made with U.S. government support under grant numbers DMID-NIAID U01 AI77887, RO1 27530, and U19 AI110819, all awarded by The National Institutes of Health. The U.S. Government has certain rights in the invention.

BACKGROUND

*Toxoplasma gondii* is an intracellular parasite that can cause severe ocular and neurological diseases in fetuses, newborn infants, and immunocompromised individuals (1). The acute infection is characterized by proliferation of tachyzoites, which replicate rapidly within host cells and lyse their host cells within 24-48 hours to release large numbers of progeny. In response to immune pressure, the parasite differentiates into a slow-growing form called bradyzoites, which resides within intracellular cysts. Formation of tissue cysts normally occurs in long-lived cells such as muscle or neuronal cells. Although antiparasitic medicines such as sulfadiazine and pyrimethamine are effective against tachyzoites, they are associated with toxicity or hypersensitivity and do not eliminate the latent, cyst form of the parasite. Thus, there is a need for development of a safe, protective vaccine.

SUMMARY OF THE INVENTION

In one aspect, the invention provides isolated polynucleotides encoding a chimeric polypeptide, wherein the chimeric polypeptide comprises
(a) a plurality of first peptide domains wherein each first peptide domain is a CD8+ T cell eliciting epitope, including but not limited to FLSLSLLVI (SEQ ID NO: 1), FMIAFISCFA (SEQ ID NO: 2), FVIFACNFV (SEQ ID NO: 3), FMIVSISLV (SEQ ID NO: 4), FLLGLLVHV (SEQ ID NO: 5), FLTDYIPGA (SEQ ID NO: 6), ITMGSLFFV (SEQ ID NO: 7), GLAAAVVAV (SEQ ID NO: 8), VLLPVLFGV (SEQ ID NO: 9), FAAAFFPAV (SEQ ID NO: 10), VVFVVFMGV (SEQ ID NO: 11), FMGVLVNSL (SEQ ID NO: 12), FLVPFVVFL (SEQ ID NO: 13), STFWPCLLR (SEQ ID NO: 14), SSAYVFSVK (SEQ ID NO: 15), KSFKDILPK (SEQ ID NO: 16), AVVSLLRLLK (SEQ ID NO: 17), and AMLTAFFLR (SEQ ID NO: 18)); and
(b) one or more second peptide domains, wherein each second peptide domain is a CD4+ epitope, including but not limited to AKFVAAWTLKAAA (SEQ ID NO: 19), AVEIHRPVPGTAPPS (SEQ ID NO: 20), IRLLASLHH (SEQ ID NO: 39), LIRLLASLH (SEQ ID NO: 40), LTLQLIRLL (SEQ ID NO: 41, VIEEFNRI (SEQ ID NO: 42), LQLIRLLAS (SEQ ID NO: 43), IDVVIEELF (SEQ ID NO: 44), or a derivative thereof.

In one embodiment, the plurality of first peptide domains comprises at least 5 peptide domains, wherein the at least 5 peptide domains include KSFKDILPK (SEQ ID NO: 16), STFWPCLLR (SEQ ID NO: 14), AVVSLLRLLK (SEQ ID NO: 17), SSAYVFSVK (SEQ ID NO: 15), AMLTAFFLR (SEQ ID NO: 18). In another embodiment, the one or more second peptide domains include AKFVAAWTLKAAA (SEQ ID NO: 19) or a derivative thereof. In another embodiment, the chimeric polypeptide comprises the amino acid sequence AVVSLLRLLKNAMLTAFFLRNAAAKSFKDILPKKAAASSAYVFSVKKAAAKFVAA WTLKAAAKSTFWPCLLR (SEQ ID NO: 24). In another embodiment, the chimeric polypeptide further comprises a third peptide domain comprising a peptide capable of promoting self-assembly/multimerization (2, 3, 4, 5, 6, or more assembled copies) of the polypeptide. In further embodiments, the chimeric polypeptide comprises the amino acid sequence SE ID NOS:27-28.

In another aspect, the invention provides recombinant expression vectors, comprising the isolated polynucleotide of any embodiment or combination of embodiments of the invention operatively linked to a control sequence. In a further embodiment, the invention provides chimeric polypeptides comprising the chimeric polypeptide encoded by the polynucleotide or the expression vector of any embodiment or combination of embodiment of the claims. In a further aspect, the invention provides assemblies comprising a plurality of the polypeptides or RNAs of the invention.

The invention further provides pharmaceutical composition, comprising: (a) the chimeric polynucleotide, the expression vector, the chimeric polypeptide, the chimeric RNA, and/or the assembly of any embodiment or combination of embodiments of the invention; and
(b) a pharmaceutically acceptable carrier. In one embodiment, the composition comprises an adjuvant, such as a TLR4 ligand or gluco glucopyranosyl lipid adjuvant in a stable emulsion (GLA-SE).

In another aspect, the invention provides methods for treating or limiting *Toxoplasma gondii* infection, comprising administering to a subject at risk of *Toxoplasma gondii* infection an amount effective to treat or limit the infection of the chimeric polynucleotide, the expression vector, the chimeric polypeptide, the chimeric RNA, and/or the assembly of any embodiment or combination of embodiments of the invention.

DESCRIPTION OF THE FIGURES

FIG. 17A: Schematic diagram of the A11 SAPN (SEQ ID NO:27) in monomeric, trimeric, pentameric, and particle form.

DETAILED DESCRIPTION OF THE INVENTION

Figure 1:
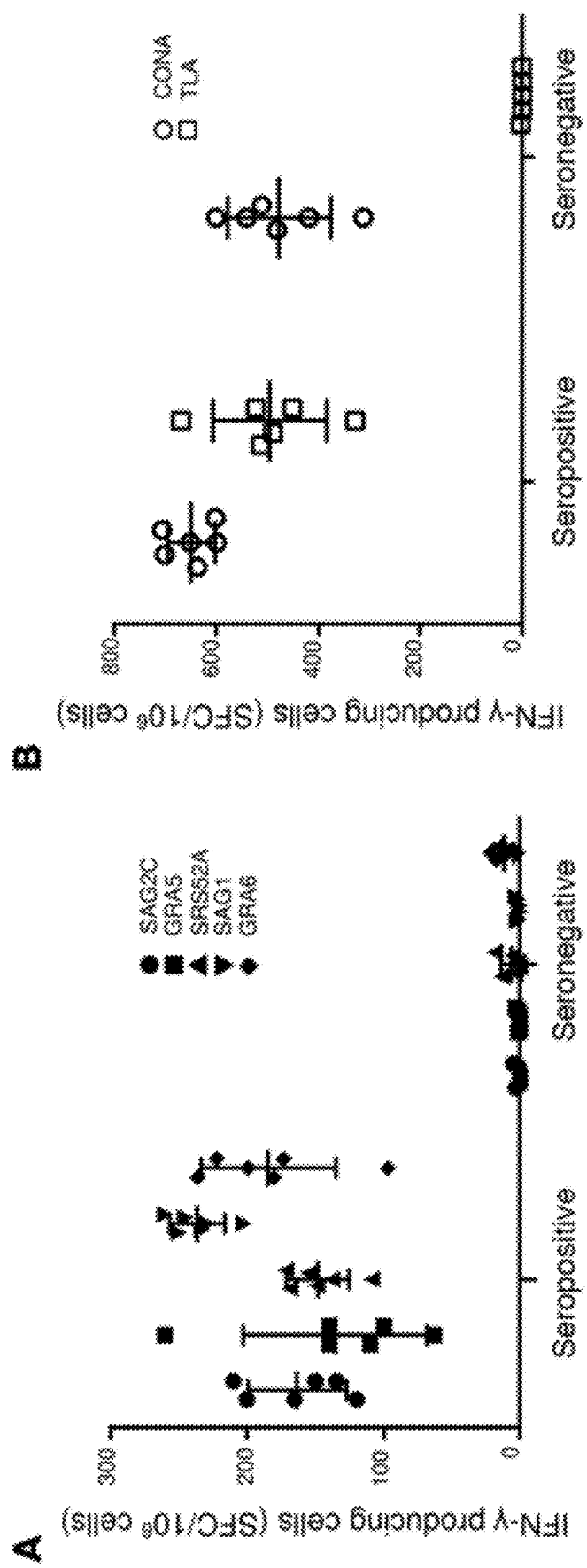
FIG. 1. Testing of peptides with PBMCs from HLA-A03 supertype *T. gondii* seropositive and seronegative donors. (A) PBMC from donors who were seropositive and seronegative for *T. gondii* were tested for response to predicted HLA-A03—restricted CD8+ T cell epitopes. Individual peptides were tested using IFN-γ ELISpot assay. (B) Concanavalin A (Con A) and tachyzoite antigen lysates (TLA) were used as controls. In A, experiments were performed 3 times. A representative experiment with one seropositive and one seronegative person shows the variability for each individual. For each person for each peptide, there were 6 determinations (wells). Each symbol represents one of these measurements of IFN-γ. The horizontal line is the mean of these 6 determinations with the SD shown. In B, methods, numbers of determinations, and comparisons were the same as for the peptides but were for Con A and TLA stimulation as controls. In 3 replicate experiments, PBMCs also were obtained from 3 *T. gondii* seropositive and 3 *T. gondii* seronegative HLA-A03 individuals. In these experiments, in the comparison of 3 seropositive and 3 seronegative persons, differences between the seropositive and seronegative persons were significant for each peptide when tested by Student's t test (P<0.05; n=3 per group, data not shown). Stimulation for seropositive and seronegative persons for TLA were different and achieved statistical significance (P<0.05). In contrast, stimulation with Con A demonstrated response of PBMC from both seronegative and seropositive donors (data not shown).

All references cited are herein incorporated by reference in their entirety. Within this application, unless otherwise stated, the techniques utilized may be found in any of several well-known references such as: Molecular Cloning: A Laboratory Manual (Sambrook, et al., 1989, Cold Spring Harbor Laboratory Press), Gene Expression Technology (Methods in Enzymology, Vol. 185, edited by D. Goeddel, 1991. Academic Press, San Diego, CA), "Guide to Protein Purification" in Methods in Enzymology (M. P. Deutshcer, ed., (1990) Academic Press, Inc.); PCR Protocols: A Guide to Methods and Applications (Innis, et al. 1990. Academic Press, San Diego, CA), Culture of Animal Cells: A Manual of Basic Technique, 2nd Ed. (R. I. Freshney. 1987. Liss, Inc. New York, NY), Gene Transfer and Expression Protocols, pp. 109-128, ed. E. J. Murray, The Humana Press Inc., Clifton, N.J.), and the Ambion 1998 Catalog (Ambion, Austin, TX).

As used herein, the singular forms "a", "an" and "the" include plural referents unless the context clearly dictates otherwise. "And" as used herein is interchangeably used with "or" unless expressly stated otherwise.

All embodiments of any aspect of the invention can be used in combination, unless the context clearly dictates otherwise.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

In a first aspect, the invention provides isolated polynucleotide encoding a chimeric polypeptide, wherein the chimeric polypeptide comprises
(a) a plurality (2, 3, 4, 5, 6, 7, 8, 9, or more) of first peptide domains wherein each first peptide domain is a $CD8^+$ T cell eliciting epitope, including but not limited to FLSLSLLVI (SEQ ID NO: 1), FMIAFISCFA (SEQ ID NO: 2), FVIFACNFV (SEQ ID NO: 3), FMIVSISLV (SEQ ID NO: 4), FLLGLLVHV (SEQ ID NO: 5), FLTDYIPGA (SEQ ID NO: 6), ITMGSLFFV (SEQ ID NO: 7), GLAAAVVAV (SEQ ID NO: 8), VLLPVLFGV (SEQ ID NO: 9), FAAAFFPAV (SEQ ID NO: 10), VVFVVFMGV (SEQ ID NO: 11), FMGVLVNSL (SEQ ID NO: 12), FLVPFVVFL (SEQ ID NO: 13), STFWPCLLR (SEQ ID NO: 14), SSAYVFSVK (SEQ ID NO: 15), KSFKDILPK (SEQ ID NO: 16), AVVSLLRLLK (SEQ ID NO: 17), and AMLTAFFLR (SEQ ID NO: 18); and
(b) one or more second peptide domains, wherein each second peptide domain is a CD4+ epitope, including but not limited to AKFVAAWTLKAAA (SEQ ID NO: 19), AVEIHRPVPGTAPPS (SEQ ID NO: 20), IRLLASLHH (SEQ ID NO: 39), LIRLLASLH (SEQ ID NO: 40), LTLQLIRLL (SEQ ID NO: 41), VIEEFNRI (SEQ ID NO: 42), LQLIRLLAS (SEQ ID NO: 43), IDVVIEELF (SEQ ID NO: 44), or a derivative thereof.

The isolated polynucleotides of the invention are shown in the examples that follow to be useful, for example, as multi-epitope nucleic acid vaccines, or to encode multi-epitope protein vaccines against *Toxoplasma gondii*. These multi-epitope vaccines are shown to increase memory $CD8^+$ T cells that produced IFN-γ and to protects mice against parasite burden when challenged with *T. gondii*, demonstrating their efficacy in cross presentation of $CD8^+$ T cell eliciting epitopes in a vaccine that can limit or prevent toxoplasmosis.

The plurality of epitopes includes at least two different $CD8^+$ T cell eliciting epitopes. In one embodiment, the plurality of epitopes includes 2, 3, 4, 5, 6, 7, 8, 9, or more of FLSLSLLVI (SEQ ID NO: 1), FMIAFISCFA (SEQ ID NO: 2), FVIFACNFV (SEQ ID NO: 3), FMIVSISLV (SEQ ID NO: 4), FLLGLLVHV (SEQ ID NO: 5), FLTDYIPGA (SEQ ID NO: 6), ITMGSLFFV (SEQ ID NO: 7), GLAAAVVAV (SEQ ID NO: 8), VLLPVLFGV (SEQ ID NO: 9), FAAAFFPAV (SEQ ID NO: 10), VVFVVFMGV (SEQ ID NO: 11), FMGVLVNSL (SEQ ID NO: 12), FLVPFVVFL (SEQ ID NO: 13), STFWPCLLR (SEQ ID NO: 14), SSAYVFSVK (SEQ ID NO: 15), KSFKDILPK (SEQ ID NO: 16), AVVSLLRLLK (SEQ ID NO: 17), and AMLTAFFLR (SEQ ID NO: 18). In one specific embodiment, the plurality of first peptide domains comprises at least 5 peptide domains, wherein the at least 5 peptide domains include KSFKDILPK (SEQ ID NO: 16), STFWPCLLR (SEQ ID NO: 14), AVVSLLRLLK (SEQ ID NO: 17), SSAYVFSVK (SEQ ID NO: 15), AMLTAFFLR (SEQ ID NO: 18). This embodiment is specifically described in the examples that follow.

The second peptide domain may be present in one or more copies. In another specific embodiment, the one or more second peptide domains include AKFVAAWTLKAAA (SEQ ID NO: 19) or a derivative thereof. This embodiment is also specifically described in the examples that follow.

In a further embodiment, some (2, 3, 4, 5, etc.) or all of the plurality of first peptide domains are separated from the other first peptide domains peptides by a spacer of 1 or more (2, 3, 4, 5, etc.) amino acid residues and/or by the one or more second peptide domains. Where multiple spacers are included in a construct, each copy of the spacer may have the same sequence, or the spacers may include 2 or more different spacers. In various specific embodiments, the spacer(s) is/are selected from the group consisting of N, K, $NA_{1-3}$ (SEQ ID NO: 21), $KA_{1-3}$ (SEQ ID NO: 22), and/or GPGPG (SEQ ID NO: 23).

In one specific embodiment, the chimeric polypeptide comprises the amino acid sequence AVVSLLRLLKNAML-TAFFLRNAAAKSFKDILPKKAAASSAYVFSVK-KAAAKFVAA WTLKAAAKSTFWPCLLR (SEQ ID NO: 24)

In another embodiment, the chimeric polypeptide further comprises a third peptide domain comprising a peptide capable of promoting self-assembly/multimerization (2, 3, 4, 5, 6, or more assembled copies) of the polypeptide. In these embodiments, the polypeptides are self-assembling protein nanoparticles, as fully described in the examples that follow. Any suitable peptide domain capable of promoting self-assembly/multimerization can be used. Non-limiting examples of the third peptide domains known to those of skill in the art and suitable for use in the present invention include, but are not limited to peptide helices containing at least one helix, or a structure formed by a helix, a coil and another helix, etc., coiled coil structures, dimerization domains within, for example, many cell surface signaling receptors, Fc regions or hinge regions of an antibody, leucine zippers, the STAT protein N terminal domain, FK506 binding protein, the LexA protein C-terminal domain, nuclear receptors, the FkpA N-terminal domain, orange carotenoid protein from *A. maxima*, M1 matrix protein from influenza, neuraminidase from influenza virus, *E. coli* fuculose aldolase;

and the like. (see, e.g., O'Shea, Science. 254: 539 (1991), Barahmand-Pour et al., Curr. Top. Microbiol. Immunol. 211: 121-128 (1996); Klemm et al., Annu. Rev. Immunol. 16: 569-592 (1998); Klemm et al., Annu. Rev. Immunol. 16: 569-592 (1998); Ho et al., Nature. 382: 822-826 (1996); and Pomeranz et al., Biochem. 37: 965 (1998)). Further examples include residues 325 to 410 in the bovine papillomavirus E2 protein, (Dostatni, N., et al., EMBO J 7 (1988) 3807-3816; Haugen, T., et al. EMBO J 7 (1988) 4245-4253; McBride, A., et al., EMBO J 7 (1988) 533-539; McBride, A., et al., Proc Natl Acad Sci USA 86 (1989) 510-514), Type I deiodinase (D1): DFLVIYIEEAHASDGW (SEQ ID NO: 31) or ADFL—YI-EAH—DGW (SEQ ID NO: 32); HIV-1 Capsid Protein: QGPKEPFRDYVDRFYKTLRA (SEQ ID NO: 33); leucine zipper dimerization motif of yeast GCN4: HMKQL D VEEL S NYHL N VARL K VGER (SEQ ID NO: 34); leucine zipper in *Escherichia coli* transcriptional antiterminator protein; and BglG: GVTQLMREMLQ-LIKFQFSLNYQEESLSYQRLVT (SEQ ID NO: 35). In various specific embodiments, the third peptide domain comprises one or more copies of a pentameric coiled coil (such as WEEWNARWDE-WENDWNDWREDWQAWRDDWARWRATWM (SEQ ID NO: 25)), a trimeric coiled coil such as RLLSRLERL-ERRNEELRRLLQLIRHENRMVLQFVRALSMQNAEL-ERRLEEL (SEQ ID NO: 26), or both.

In another embodiment, the third polypeptide comprises a flagellin protein or domain thereof, including but not limited to:

```
                                         (SEQ ID NO: 45)
MAQVINTNSLSLLTQNNLNRSQSALGTAIERLSSGLRINSARDDAAGQ

AIANRFTANIRGLTQASRNANDGISIAQTTEGALNEINNNLQRVRELA

VQSANSTNSQSDLDSIQAEITQRLNEIDRVSGQTQFNGVRVLAQDNTL

TIQVGANDGETIDIDLRQINSQTLGLDQLNV;
and/or
                                         (SEQ ID NO: 46)
TENPLQRIDAALAQVDALRSDLGAVQNRFNSAITNLGNTVNNLSEARS

RIEDSDYATEVSNMSRAQILQQAGTSVLAQANQVPQNVLSLLR
``` of *Salmonella enterica* flagellin.

In another specific embodiment, the chimeric polypeptide comprises or consists of the amino acid sequence selected from the group consisting of SEQ ID NOS:27-28.

A11 (residues in parentheses are optional)

```
                                         (SEQ ID NO: 27)
((MGDKHHHHHHHHH))KDGSDKGSWEEWNARWDEWENDWNDWREDW

QAWRDDWARWRATWMGGRLLSRLERLERRNEELRRLLQLIRHENRMVL

QFVRALSMQNAELERRLEELARGMAQVINTNSLSLLTQNNLNRSQSAL

GTAIERLSSGLRINSARDDAAGQAIANRFTANIRGLTQASRNANDGIS

IAQTTEGALNEINNNLQRVRELAVQSANSTNSQSDLDSIQAEITQRLN

EIDRVSGQTQFNGVRVLAQDNTLTIQVGANDGETIDIDLRQINSQTLG
```

-continued

```
LDQLNVQQEYESDDAVVSLLRLLKNAMLTAFFLRNAAA

KSFKDILPKKAAASSAYVFSVKKAAAKFVAAWTLKAAAKSTFWPC

LLRDSDSDTENPLQRIDAALAQVDALRSDLGAVQNRFNSAITNLGNTV

NNLSEARSRIEDSDYATEVSNMSRAQILQQAGTSVLAQANQVPQNVLS

LLR;
``` and

Tox-all (residues in parentheses are optional)

```
                                         (SEQ ID NO: 28)
(MGDDHHHHHHHHHH)

WFMGVLVNSLQDITMGSLFFVQDFMIVSISLVQDGLAAAVVAVQDLPQ

FATAATRDSPASGRYIQQMLDQRCQEIAAELCQSGLRKMCVPSSRIVA

RNAVGITHQNTLQWRCFDTASLLESNQENNGVNCVDDCGHTIPCPGGV

HRQNSNHATRHEILSKLVEEGVQRFCSPYQASANKYCNDKFPGTIARR

SKGFGNNVEVAWRCYEKASLLYSVYAECASNCGTTWYCPGGRRGTSTE

LDKRHYTEEEGIRQAIGSVDSPCSEVEVCLPKDENPPLCLDESGQISR

GSWEEWNARWDEWENDWNDWREDWQAWRDDWARWRATWMGGRLLSRLE

RLERRNEELRRLLQLIRHENRMVLQFVRALSMQNAELERRLEELARGM

AQVINTNSLSLLTQNNLNRSQSALGTAIERLSSGLRINSARDDAAGQA

IANRFTANIRGLTQASRNANDGISIAQTTEGALNEINNNLQRVRELAV

QSANSTNSQSDLDSIQAEITQRLNEIDRVSGQTQFNGVRVLAQDNTLT

IQVGANDGETIDIDLRQINSQTLGLDQLNVQQEYESDDAVVSLLRLLK

NAMLTAFFLRNAAAKSFKDILPKKAAASSAYVFSVKKAAAKFVAAWTL

KAAAKSTFWPCLLRDSDSDTENPLQRIDAALAQVDALRSDLGAVQNRF

NSAITNLGNTVNNLSEARSRIEDSDYATEVSNMSRAQILQQAGTSVLA

QANQVPQNVLSLLR.
```

As used herein, the amino acid residues are abbreviated as follows: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

As used throughout the present application, the term "polypeptide" is used in its broadest sense to refer to a sequence of subunit amino acids. The polypeptides of the invention may comprise L-amino acids, D-amino acids (which are resistant to L-amino acid-specific proteases in vivo), or a combination of D- and L-amino acids. The polypeptides described herein may be chemically synthesized or recombinantly expressed. The polypeptides may be linked to other compounds to promote an increased half-life in vivo, such as by PEGylation, HESylation, PASylation, glycosylation, or may be produced as an Fc-fusion or in de-immunized variants. Such linkage can be covalent or non-covalent as is understood by those of skill in the art.

In another embodiment, the chimeric polypeptide further comprises a secretory signal. Any suitable secretory signal may be used; in one non-limiting embodiment, the secretory signal is the murine Igκ-chain signal sequence (MGMQVQIQSLFLLLLWVPGSRG (SEQ ID NO: 47)). In a preferred embodiment, the secretory signal is present at the N-terminus of the chimeric polypeptide.

In another aspect, the invention provides recombinant expression vector, comprising the isolated polynucleotide of any embodiment or combination of embodiments of the invention operatively linked to a control sequence.

As used herein, a "recombinant expression vector" includes vectors that operatively link a nucleic acid coding region or gene to any control sequences capable of effecting expression of the encoded polypeptide. "Control sequences" operably linked to the nucleic acid sequences of the invention are nucleic acid sequences capable of effecting the expression of the nucleic acid molecules. The control sequences need not be contiguous with the nucleic acid sequences, so long as they function to direct the expression thereof. Thus, for example, intervening untranslated yet transcribed sequences can be present between a promoter sequence and the nucleic acid sequences and the promoter sequence can still be considered "operably linked" to the coding sequence. Other such control sequences include, but are not limited to, polyadenylation signals, termination signals, and ribosome binding sites. Such expression vectors can be of any type known in the art, including but not limited plasmid and viral-based expression vectors. The control sequence used to drive expression of the disclosed nucleic acid sequences in a mammalian system may be constitutive (driven by any of a variety of promoters, including but not limited to, CMV, SV40, RSV, actin, EF) or inducible (driven by any of a number of inducible promoters including, but not limited to, tetracycline, ecdysone, steroid-responsive). The construction of expression vectors for use in transfecting prokaryotic cells is also well known in the art, and thus can be accomplished via standard techniques. (See, for example, Sambrook, Fritsch, and Maniatis, in: Molecular Cloning, A Laboratory Manual, Cold Spring Harbor Laboratory Press, 1989; Gene Transfer and Expression Protocols, pp. 109-128, ed. E. J. Murray, The Humana Press Inc., Clifton, N.J.), and the Ambion 1998 Catalog (Ambion, Austin, TX). The expression vector must be replicable in the host organisms either as an episome or by integration into host chromosomal DNA. In a preferred embodiment, the expression vector comprises a plasmid. However, the invention is intended to include other expression vectors that serve equivalent functions, such as viral vectors.

In one embodiment, of the recombinant expression vectors of the invention, the control sequences comprise viral proteins required for RNA replication, such as viral proteins encoded by an alphavirus genome including but not limited to Venezuelan Equine Encephalitis (VEE) alphavirus. In a further embodiment, the vector comprises a gene encoding a self-amplifying RNA operatively linked to the polynucleotide (i.e.: self-amplification of the self-amplifying RNA results in amplification of RNA encoding the chimeric polypeptide). Any suitable self-amplifying RNA may be used, including but not limited to the self-amplifying RNA of SEQ ID NO:29.

```
                                       (SEQ ID NO: 29)
GAAUUUGCUGCGACGAUGGGUAUGCAAGUCCAGAUCCAGAGCCUGUUC

CUGCUGCUGCUGUGGGUGCCGGGUUCACGCGGUAUGGCGGUGGUUAGC

CUGCUGCGUCUGCUGAAAAACGCCAUGCUGACCGCAUUUUUCCUGCGC

AAUGCGGCCGCAAAGAGUUUCAAGGAUAUCCUGCCGAAAAAGGCUGCG
```

-continued
```
GCCAGCUCUGCGUAUGUCUUUUCCGUGAAAAAGGCAGCUGCGAAAUUC

GUUGCUGCCUGGACCCUGAAAGCUGCCGCUAAAUCGACGUUCUGGCCG

UGUCUGCUGCGU.
```

In another embodiment, the self-amplifying RNA is encoded by the nucleic acid sequence of SEQ ID NO:30.

```
                                       (SEQ ID NO: 30)
CATGGGTATGCAGGTCCAGATTCAGTCACTCTTTCTCCTCCTCCTCTG

GGTCCCCGGTAGCCGGGGTATGGCCGTGGTCAGCCTGCTCAGGCTGCT

CAAGAACGCCATGCTGACCGCTTTCTTTCTCAGAAATGCCGCTGCAAA

GTCTTTCAAAGACATCCTGCCCAAGAAAGCCGCTGCAAGCTCCGCCTA

CGTGTTCAGTGTCAAGAAAGCCGCTGCAAAATTTGTGGCC
```

In another aspect, the invention provides chimeric polypeptides comprising a polypeptide encoded by the polynucleotide or expression vector of any embodiment or combination of the embodiments of the present invention, or a chimeric RNA comprising an RNA encoded by the polynucleotide or expression vector of any embodiment or combination of the embodiments of the present invention.

In a further aspect, the invention provides assemblies, comprising a plurality (2, 3, 4, 5, 6, or more) of the polypeptides or RNAs of any embodiment or combination of embodiments of the invention having the third peptide domain. In this embodiment, the plurality of polypeptides are self-assembled via non-covalent binding of the third domains. Any suitable peptide domain capable of promoting self-assembly/multimerization can be used. Non-limiting examples of the third peptide domains known to those of skill in the art and suitable for use in the present invention include, but are not limited to peptide helices containing at least one helix, or a structure formed by a helix, a coil and another helix, etc., coiled coil structures, dimerization domains within, for example, many cell surface signaling receptors, Fc regions or hinge regions of an antibody, leucine zippers, the STAT protein N terminal domain, FK506 binding protein, the LexA protein C-terminal domain, nuclear receptors, the FkpA N-terminal domain, orange carotenoid protein from *A. maxima*, M1 matrix protein from influenza, neuraminidase from influenza virus, *E. coli* fuculose aldolase; and the like. (see, e.g., O'Shea, Science. 254: 539 (1991), Barahmand-Pour et al., Curr. Top. Microbiol. Immunol. 211: 121-128 (1996); Klemm et al., Annu. Rev. Immunol. 16: 569-592 (1998); Klemm et al., Annu. Rev. Immunol. 16: 569-592 (1998); Ho et al., Nature. 382: 822-826 (1996); and Pomeranz et al., Biochem. 37: 965 (1998)). Further examples include residues 325 to 410 in the bovine papillomavirus E2 protein, (Dostatni, N., et al., EMBO J 7 (1988) 3807-3816; Haugen, T., et al. EMBO J 7 (1988) 4245-4253; McBride, A., et al., EMBO J 7 (1988) 533-539; McBride, A., et al., Proc Natl Acad Sci USA 86 (1989) 510-514), Type I deiodinase (D1): DFLVIYIEEAHASDGW (SEQ ID NO: 31) or ADFL—YI-EAH—DGW (SEQ ID NO: 32); HIV-1 Capsid Protein: QGPKEPFRDYVDRFYKTLRA (SEQ ID NO: 33); leucine zipper dimerization motif of yeast GCN4: HMKQL D VEEL S NYHL N VARL K VGER (SEQ ID NO: 34); leucine zipper in *Escherichia coli* transcriptional antiterminator protein; and BglG: GVTQLMREMLQ-LIKFQFSLNYQEESLSYQRLVT (SEQ ID NO: 35). In various specific embodiments, the third peptide domain comprises one or more copies of a pentameric coiled coil (such as WEEWNARWDE-WENDWNDWREDWQAWRDDWARWRATWM (SEQ ID NO: 25)), a trimeric coiled coil such as RLLSRLERL-ERRNEELRRLLQLIRHENRMVLQFVRALSMQNAEL-ERRLEEL (SEQ ID NO: 26), or both. In another embodiment, the third polypeptide comprises a flagellin protein or domain thereof, including but not limited to:

```
                                         (SEQ ID NO: 45)
MAQVINTNSLSLLTQNNLNRSQSALGTAIERLSSGLRINSARDDAAGQ

AIANRFTANIRGLTQASRNANDGISIAQTTEGALNEINNNLQRVRELA

VQSANSTNSQSDLDSIQAEITQRLNEIDRVSGQTQFNGVRVLAQDNTL

TIQVGANDGETIDIDLRQINSQTLGLDQLNV;
and/or (SEQ ID NO: 46)
TENPLQRIDAALAQVDALRSDLGAVQNRFNSAITNLGNTVNNLSEARS

RIEDSDYATEVSNMSRAQILQQAGTSVLAQANQVPQNVLSLLR
``` of *Salmonella enterica* flagellin.

In another aspect, the invention provides pharmaceutical compositions, comprising:
 (a) the chimeric polynucleotide, the expression vector, the chimeric polypeptide, the chimeric RNA, and/or the assembly of any embodiment or combination of embodiments of the invention; and
 (b) a pharmaceutically acceptable carrier.

As used herein, the phrase "pharmaceutically acceptable salt" refers to both pharmaceutically acceptable acid and base addition salts and solvates. Such pharmaceutically acceptable salts include salts of acids such as hydrochloric, phosphoric, hydrobromic, sulfuric, sulfinic, formic, toluene-sulfonic, methanesulfonic, nitric, benzoic, citric, tartaric, maleic, hydroiodic, alkanoic such as acetic, HOOC—(CH$_2$)$_n$—COOH where n is 0-4, and the like. Non-toxic pharmaceutical base addition salts include salts of bases such as sodium, potassium, calcium, ammonium, and the like. Those skilled in the art will recognize a wide variety of non-toxic pharmaceutically acceptable addition salts.

The chimeric polynucleotide, the expression vector, the chimeric polypeptide, the chimeric RNA, and/or the assembly may be the sole active agent in the composition, or the composition may further comprise one or more other agents suitable for an intended use, including but not limited to adjuvants to stimulate the immune system generally and improve immune responses overall. Any suitable adjuvant can be used. The term "adjuvant" refers to a compound or mixture that enhances the immune response to an antigen. Exemplary adjuvants include, but are not limited to, Adju-Phos, Adjumer™, albumin-heparin microparticles, Algal Glucan, Algammulin, Alum, Antigen Formulation, AS-2 adjuvant, autologous dendritic cells, autologous PBMC, Avridine™, B7-2, BAK, BAY R1005, Bupivacaine, Bupivacaine-HCl, BWZL, Calcitriol, Calcium Phosphate Gel, CCR5 peptides, CFA, Cholera holotoxin (CT) and Cholera toxin B subunit (CTB), Cholera toxin A1-subunit-Protein A D-fragment fusion protein, CpG, CRL1005, Cytokine-containing Liposomes, D-Murapalmitine, DDA, DHEA, Diphtheria toxoid, DL-PGL, DMPC, DMPG, DOC/Alum Complex, Fowlpox, Freund's Complete Adjuvant, Gamma Inulin, Gerbu Adjuvant, GM-CSF, GMDP, hGM-CSF, hIL-12 (N222L), hTNF-alpha, IFA, IFN-gamma in pcDNA3, IL-12 DNA, IL-12 plasmid, IL-12/GMCSF plasmid (Sykes), IL-2 in pcDNA3, IL-2/Ig plasmid, IL-2/Ig protein, IL-4, IL-4 in pcDNA3, Imiquimod, ImmTher™, Immunoliposomes Containing Antibodies to Costimulatory Molecules, Interferon-gamma, Interleukin-1 beta, Interleukin-12, Interleukin-2, Interleukin-7, ISCOM(s)™, Iscoprep 7.0.3™, Keyhole Limpet Hemocyanin, Lipid-based Adjuvant, Liposomes, Loxoribine, LT(R192G), LT-OA or LT Oral Adjuvant, LT-R192G, LTK63, LTK72, MF59, MONTANIDE ISA 51, MONTANIDE ISA 720, MPL.TM., MPL-SE, MTP-PE, MTP-PE Liposomes, Murametide, Murapalmitine, NAGO, nCT native Cholera Toxin, Non-Ionic Surfactant Vesicles, non-toxic mutant E112K of Cholera Toxin mCT-E112K, p-Hydroxybenzoique acid methyl ester, pCIL-10, pCIL12, pCMVmCAT1, pCMVN, Peptomer-NP, Pleuran, PLG, PLGA, PGA, and PLA, Pluronic L121, PMMA, PODDS™, Poly rA: Poly rU, Polysorbate 80, Protein Cochleates, QS-21, Quadri A saponin, Quil-A, Rehydragel HPA, Rehydragel LV, RIBI, Ribilike adjuvant system (MPL, TMD, CWS), S-28463, SAF-1, Sclavo peptide, Sendai Proteoliposomes, Sendai-containing Lipid Matrices, Span 85, Specol, Squalane 1, Squalene 2, Stearyl Tyrosine, Tetanus toxoid (TT), Theramide™, Threonyl muramyl dipeptide (TMDP), Ty Particles, and Walter Reed Liposomes. In one specific embodiment, the adjuvant comprises a TLR4 ligand. In another specific embodiment, the adjuvant comprises gluco glucopyranosyl lipid adjuvant in a stable emulsion (GLA-SE).

In another embodiment, the carrier may comprise a liposome; this embodiment may be particularly useful for polynucleotides and/or RNA embodiments of the invention.

In another aspect, the invention provides methods for treating or limiting *Toxoplasma gondii* infection, comprising administering to a subject at risk of *Toxoplasma gondii* infection an amount effective to treat or limit the infection of the chimeric polynucleotide, the expression vector, the chimeric polypeptide, the chimeric RNA, the assembly, or the pharmaceutical composition of any embodiment or combination of embodiments of the invention.

As used herein, the term "subject" refers to any animal, including mammals, preferably mice, rats, other rodents, rabbits, dogs, cats, swine, cattle, sheep, horses, or primates, and most preferably humans.

As used herein, the phrase "amount effective", "therapeutically effective amount" or "effective to treat" refers to the amount of active compound or pharmaceutical agent that elicits the biological or medicinal response that is being sought in a tissue, system, animal, individual or human by a researcher, veterinarian, medical doctor or other clinician.

In certain embodiments, a therapeutically effective amount can be an amount suitable for
 (1) limiting development of the disease; for example, limiting development of a disease, condition or disorder in an individual who may be predisposed to the disease, condition or disorder but does not yet experience or display the pathology or symptomatology of the disease;
 (2) inhibiting the disease; for example, inhibiting a disease, condition or disorder in an individual who is experiencing or displaying the pathology or symptomatology of the disease, condition or disorder; or
 (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

As used here, the terms "treatment" and "treating" means (i) ameliorating the referenced disease state, for example, ameliorating a disease, condition or disorder in an individual who is experiencing or displaying the pathology or symptomatology of the disease, condition or disorder (i.e., reversing or improving the pathology and/or symptomatology) such as decreasing the severity of disease; or (ii) eliciting the referenced biological effect (e.g., reducing parasitic load or adverse effects the parasite is causing in the human it infects).

In another embodiment, the administering comprising
(a) administering an initial dose of the chimeric polynucleotide or the expression vector of any embodiment or combination of embodiments in combination with an adjuvant, including but not limited to GLA-SE; and
(b) administering a booster dose of the chimeric polypeptide, assembly thereof, or a pharmaceutical composition thereof. In one embodiment, the booster composition comprises an adjuvant including but not limited to GLA-SE.

For all methods disclosed herein, the compositions are typically formulated as a pharmaceutical composition for administration, such as those disclosed above, and can be administered via any suitable route, including orally, parentally, by inhalation spray, rectally, topically, or by electroporation in dosage unit formulations containing conventional pharmaceutically acceptable carriers, adjuvants, and vehicles. The term parenteral as used herein includes, subcutaneous, intravenous, intra-arterial, intramuscular, intrasternal, intratendinous, intraspinal, intracranial, intrathoracic, infusion techniques or intraperitoneally. Dosage regimens can be adjusted to provide the optimum desired response (e.g., a therapeutic or prophylactic response). A suitable dosage range may, for instance, be 0.1 ug/kg-100 mg/kg body weight; alternatively, it may be 0.5 ug/kg to 50 mg/kg; 1 ug/kg to 25 mg/kg, or 5 ug/kg to 10 mg/kg body weight. The compositions can be delivered in a single bolus, or may be administered more than once (e.g., 2, 3, 4, 5, or more times) as determined by an attending physician. When adjuvant is used dosage regimens can be adjusted to lower the amount of targeted antigen used to provide the optimum desired response.

Example 1. Adjuvanted Multi-Epitope Vaccines Protect HLA-A*1101 Transgenic Mice Against *Toxoplasma gondii*

We created and tested multi-epitope DNA or protein vaccines with TLR4 ligand emulsion adjuvant (gluco glucopyranosyl lipid adjuvant in a stable emulsion (GLA-SE)) for their ability to protect against *Toxoplasma gondii* in HLA transgenic mice. Our constructs each included five of down selected CD8$^+$ T cell eliciting epitopes, a universal CD4$^+$ helper T lymphocyte epitope (PADRE), a secretory signal, all arranged to maximize MHC Class I presentation. Their capacity to elicit immune and protective responses was studied using immunization of HLA-A*1101 transgenic mice. These multi-epitope vaccines increased memory CD8$^+$ T cells that produced IFN-$\gamma$ and protected mice against parasite burden when challenged with *T. gondii*. Endocytosis of emulsion-trapped protein and cross presentation of the antigens may account for the immunogenicity of our adjuvanted protein. This work demonstrates a novel adjuvanted platform assembly of peptides resulting in cross presentation of CD8$^+$ T cell eliciting epitopes in a vaccine that prevents toxoplasmosis.

Results
Identification of New Candidate *T. gondii* Specific HLA-A*1101-Restricted Epitopes Five peptide epitopes that show high affinity binding to HLA-A*1101 molecules, derived from SAG1, SRS52A, SAG2C, GRA6 and GRA5 have representative affinities for HLA-A*1101 molecules, a haplotype that covered 16-30% population in China; 7-16% in Europe and North America; 1.5-10% in South America.

To determine which of these peptides would be recognized in the context of *Toxoplasma* infection, peripheral blood mononuclear cells (PBMC) from *T. gondii*-seropositive HLA-A03 individuals were tested for response to these peptides in pools or individually by using an IFN-$\gamma$ ELISpot assay. Candidate peptides were considered immunogenic if they induced IFN-$\gamma$-secreting spot formation that was significant compared to an irrelevant HLA-A*1101-restricted peptide. As shown in FIG. 1, there were five peptide pools which stimulated significant response by PBMC derived from *Toxoplasma* seropositive HLA-A03 individuals. These were: one from SAG1$_{224-232}$ (KSFKDILPK (SEQ ID NO: 16)), SAG2C$_{13-21}$ (STFWPCLLR (SEQ ID NO: 14)), GRA5$_{89-98}$ (AVVSLLRLLK (SEQ ID NO: 17)), SRS52A$_{250-258}$ (SSAYVFSVK (SEQ ID NO: 15)), and GRA6$_{164-172}$ (AMLTAFFLR (SEQ ID NO: 18)).

HLA-A*1101-Transgenic Mice as a Model to Assess Cellular Immunogenicity of 5 Identified HLA-A*1101-Restricted CD8+ T Cell Epitope Peptides To address the HLA-A11-specific genetic restriction of the 5 HLA-A*1101 epitopes identified to prime for IFN-$\gamma$ responses, HLA-A*1101-transgenic and C57BL/6 wild-type control mice were immunized subcutaneously with peptides alone or mixed with GLA-SE. As shown in Table 1, robust IFN-$\gamma$ responses from splenocytes were observed following immunization by a pool of peptides (5 HLA-A*1101 peptides+PADRE) mixed with GLA-SE in HLA-A*1101-transgenic mice compared with C57BL/6 control mice. Immunization of HLA-A*1101-transgenic mice with GLA-SE alone did not elicit IFN-$\gamma$ when splenocytes were tested with or without peptides (i.e. background levels).

Figure 2:
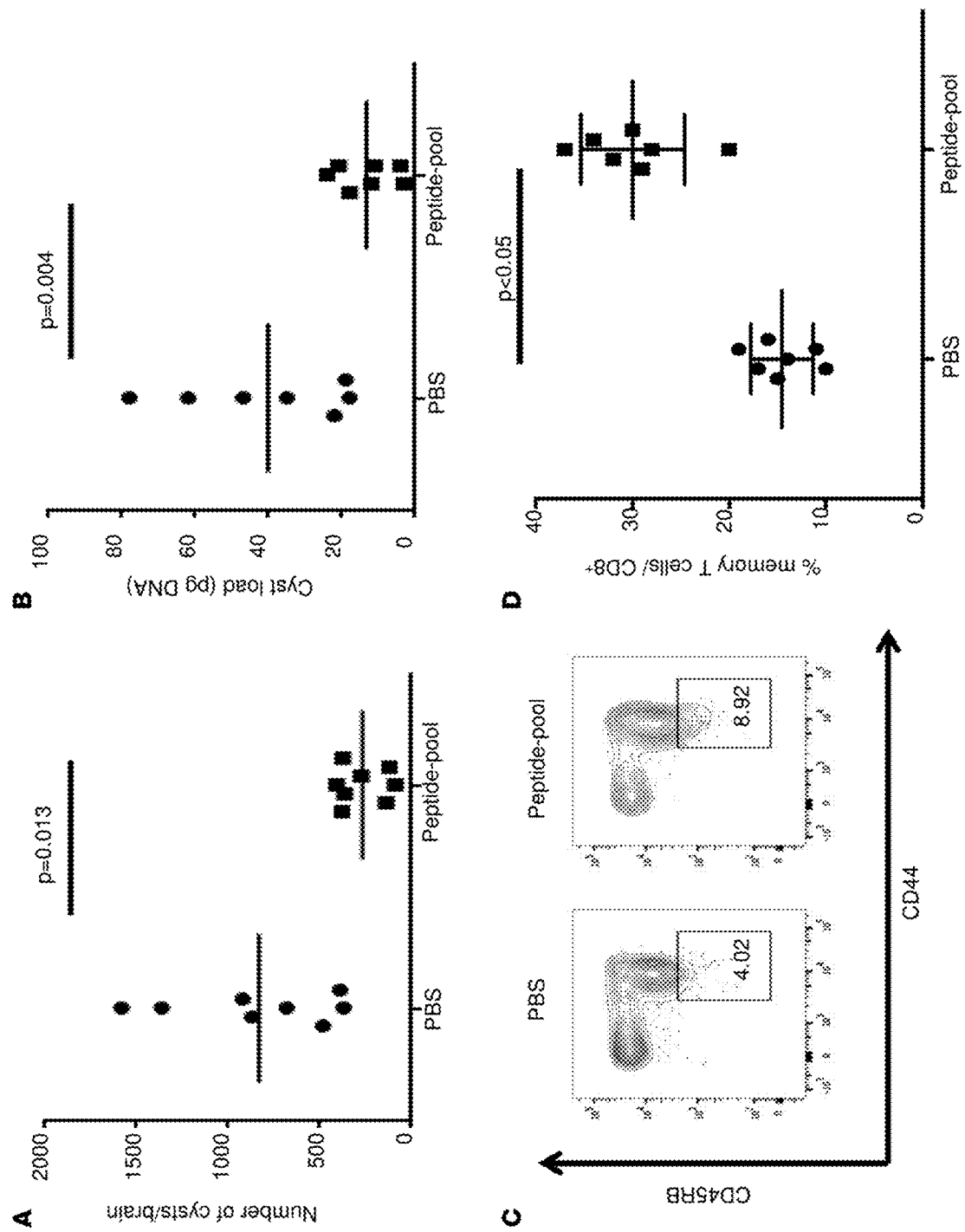
FIG. 2. Immunogenicity and efficacy of 5 identified A11-restricted CD8+ T cell epitope pool peptides in combination with PADRE and GLA-SE adjuvant in HLA-A*11:01 transgenic mice. (A) *T. gondii* brain cysts number was significantly reduced in HLA-A*11:01 mice immunized with pool of peptides plus PADRE and GLA-SE adjuvant at 21 days after challenge with 2,000 *T. gondii* ME49-Fluc (Type II) parasites (n=8 mice per group, in 2 replicate experiments with 4 mice per experiment, pooled; *P<0.013, Student's t test). (B) Quantitative PCR for the parasite burden in the *T. gondii*—challenged HLA-A*11:01 mice brains (n=7 mice per group combining 2 replicate experiments, *P<0.004, Student's t test). (C and D) Flow cytometry gating for CD8+ memory T cells 11 weeks after immunization of HLA-A*11:01 mice with pooled adjuvanted peptides. Cells are gated on CD3+CD8+ T cells. Memory T cells were defined as CD44hiCD45RBlo. For each group, a representative FACS plot is shown with the percent of CD8+ memory T cells shown. For each group, n=3 and differences were significant; P<0.05, Student's t test. This experiment is representative of 2 replicates. Horizontal lines are means and SDs are shown in D.

Vaccination with Peptide Pools, PADRE and GLA-SE Adjuvant Protects Mice and Increase Memory Against Type II Parasite Challenge HLA-A*1101-transgenic mice were immunized with peptide pools combined with GLA-SE adjuvant and PADRE three times at intervals of two weeks. PBS was used as control. Five weeks after the last immunization, mice were challenged with type II parasites. Differences in brain cyst numbers between control and immunized mice were significant (p<0.013) as shown in FIG. 2A-B, with the immunized mice having a reduced cyst burden. Spleens from unchallenged immunized and control mice were tested for the ability of the immunization to induce CD8$^+$ T cell memory response. As shown in FIG. 2C-D, there is an increase of memory CD8$^+$ T cells in the immunized group.

LO and AZ Multi-Epitope Polypeptide Immunogenicity in Vitro

The CD8$^+$ T cell-epitopes identified are intended to form the basis of *Toxoplasma* vaccine for persons with the HLA-A*1101 supertype. We expressed and purified from *E. coli* a protein composed of the five epitopes linked in a sequence with the universal CD4$^+$ T cell epitope, PADRE (AKFVAAWTLKAAA (SEQ ID NO: 19)) and the murine Igκ-chain signal sequence for targeting protein to secretory pathway at the N-terminus. The epitopes were linked together with N/K alanines or GPGPG (SEQ ID NO: 23) as linker, named as LO and AZ, respectively (FIG. 3A-B). Both proteins were purified via Ni-NTA affinity column and the molecular weight was verified by SDS-PAGE analysis (FIG. 3C). Immunogenicity of the two proteins compared to the pool of the 5 individual A11-restricted CD8+ T cell epitope peptides was tested in vitro. Briefly, PBMCs from *T. gondii* seropositive HLA-A03 supertype humans were tested for their ability to generate IFN-γ in response to the stimulation with either LO or AZ protein or a pool of the peptides for 2 days to allow time for processing the proteins and presentation thereof to MHC class I. The data in FIG. 4A-C demonstrate IFN-γ secretion was significantly enhanced by stimulation with either LO or AZ multi-epitope polypeptide compared with a pool of the individual 5 epitope peptides (P<0.03).

Immunization with LO and AZ Multi-Epitope Polypeptides with GLA-SE Adjuvant Confers a Potent Protection in HLA-A*1101 Transgenic Mice Against *T. gondii*.

Figure 5:
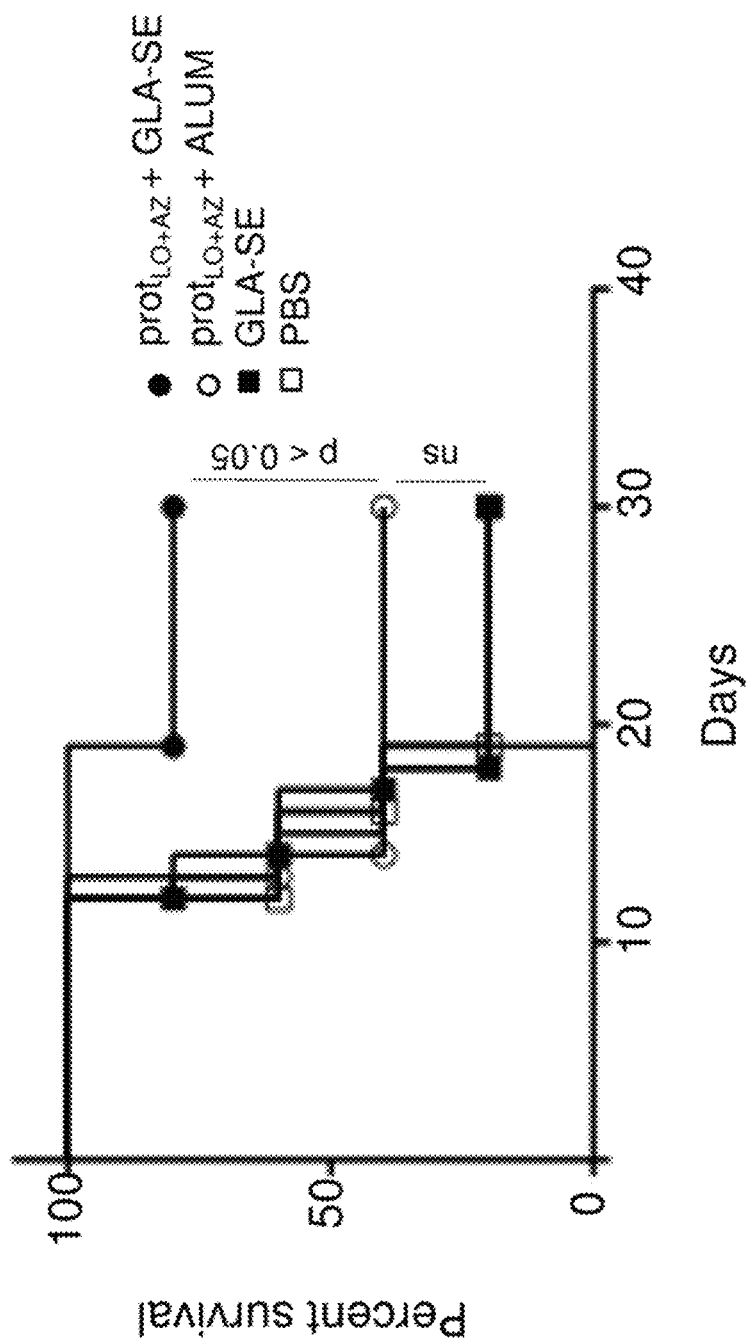
FIG. 5. Multivalent polypeptide LO and AZ protective efficacy in vivo with HLA-A*11:01 transgenic mice survival curve after challenge with Type II parasites. Two weeks after last immunization, the transgenic mice immunized with pooled LO and AZ proteins (prot) in combination with either adjuvant GLA-SE or ALUM adjuvant or injected with PBS were infected with 2,000 Me49 (Fluc) parasites. The survival rates of the 2 groups were recorded. This figure shows data from mice in both of 2 replicate experiments combined (n=5 control and 5 immunized mice). Kaplan-Meier curves were generated and survival compared across groups using the log-rank test, P<0.05. Differences between protLO+AZ+GLA-SE and all other groups were significant (P<0.05) and differences between protLO+AZ+GLA-SE and protLO+AZ+ALUM also were compared for survival using log-rank test and Kaplan-Meier analysis.

HLA-A*1101 transgenic mice were immunized with a combination of LO and AZ multi-epitope polypeptides with GLA-SE or ALUM adjuvant. As a control, mice were immunized with adjuvant alone or PBS. Mice were then challenged 2 weeks after the last immunization with type II strains of *T. gondii*. As shown in FIG. 5, 80% of mice immunized with LO and AZ multi-epitope polypeptides emulsified in GLA-SE adjuvant survived parasite challenge. In contrast, only 30% of mice immunized with the ALUM adjuvant plus polypeptides survived parasite challenge (P<0.04). As a control, neither mice immunized with the adjuvant alone nor those immunized with PBS increase their survival after challenge (FIG. 5).

Figure 6:
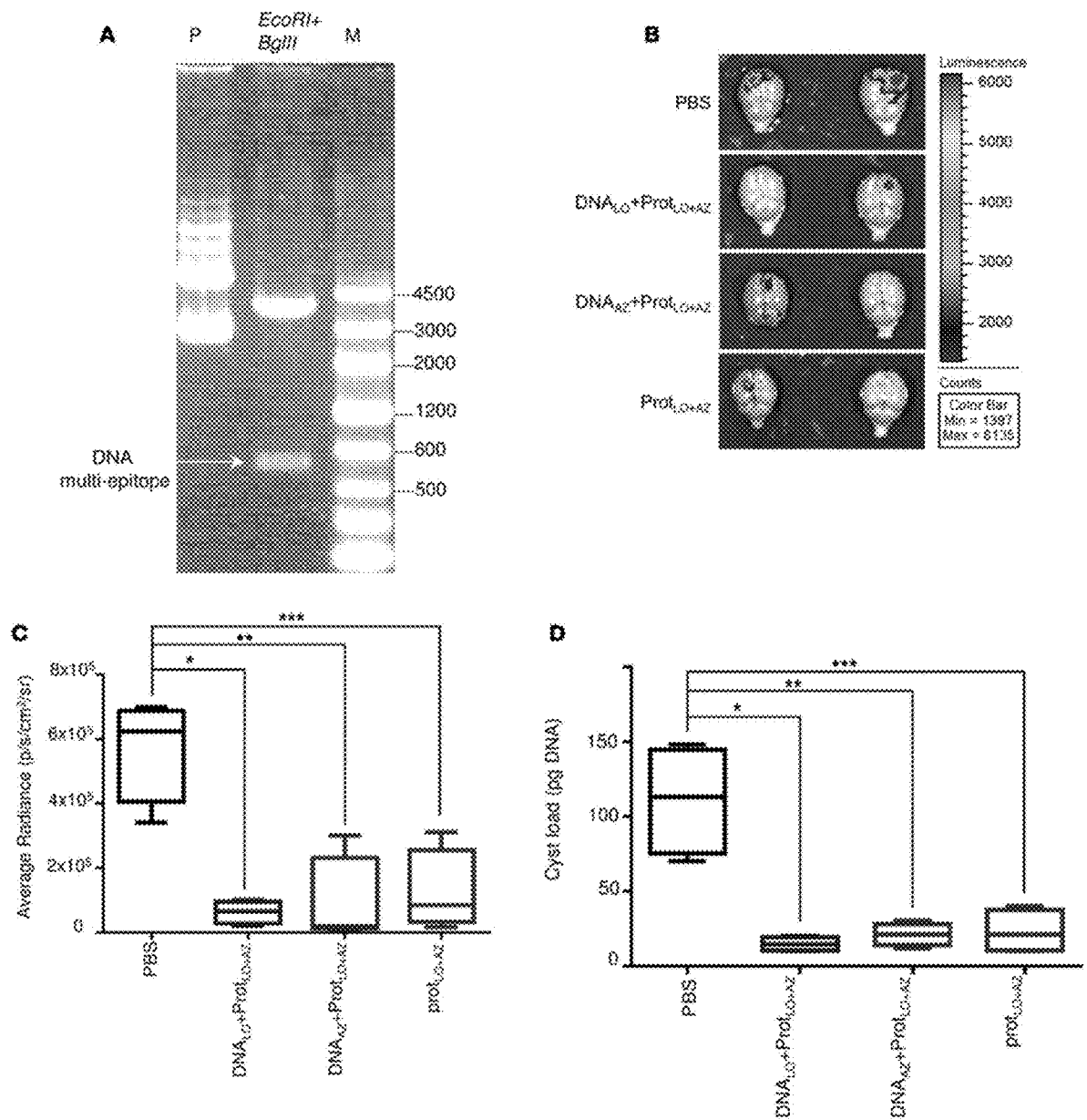
FIG. 6. DNA prime-protein boost regimen. (A) pMB75.6 vector used as a DNA vaccine vector for this study. Lane P: pMB75.6 plasmid; lane 2: pMB75.6 plasmid digested with EcoRI and BglII lane M: K B ladder. (B) *T. gondii* brain cysts luciferase expression was reduced in HLA-A*11:01 mice immunized with DNA/protein boost at 21 days after challenge with 2,000 *T. gondii* ME49-Fluc (Type II) expressing luciferase. (C) Xenogen imaging of brain ex vivo following the injection of luciferin into the retro-orbital plexus and then exposure of the brain to luciferin solution. n=5 per group, *P=0.0008, P=0.004, *P=0.004 (Student's t test after one-way ANOVA). (D) Enumeration of cysts was performed with brains of mice challenged 21 days after final immunization. These experiments were performed at least 2 times, and one representative experiment of 2 is shown: n=5 control and 5 immunized mice. *P=0.002, P=0.003, *P=0.004; Student's t test was used to compere the groups. For C and D, the plots show median, with box extending from the 25th to 75th percentile and the whiskers extending from minimum and maximum values of the data set. One-way ANOVA was performed before the Student's t test to determine whether there was an overall difference between the groups.
Figure 7:
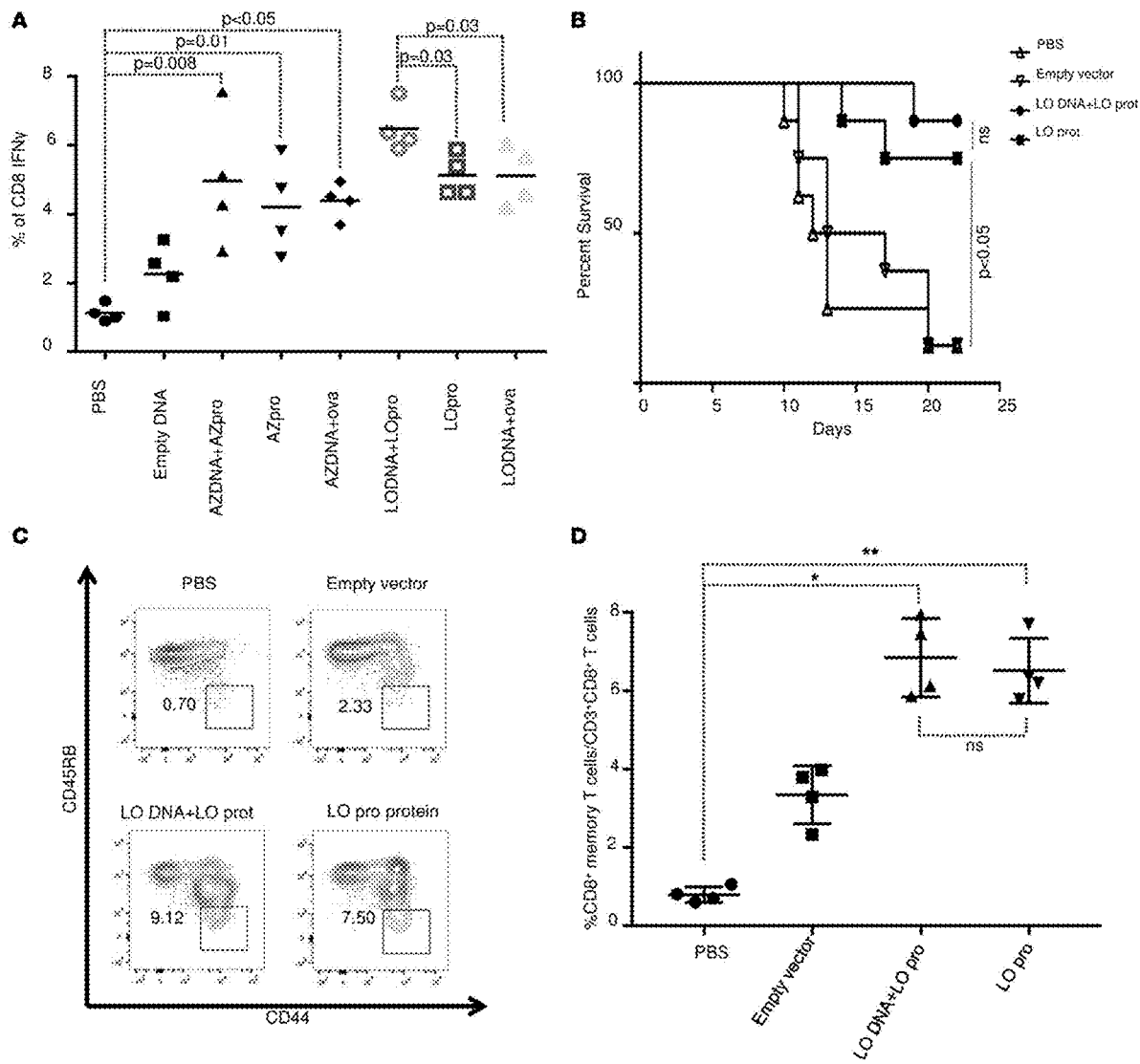
FIG. 7. CD8+ T cell responses in HLA-A*11:01 mice following immunization. (A) Splenocytes from immunized mice with LO DNA, AZ DNA, and multi-epitope polypeptides alone or combined were harvested for 10-14 days after immunization and exposed to LO or AZ polypeptide for ex vivo IFN-γ expression. Quantitation of IFN-γ from mouse splenocytes was evaluated in 2 separate experiments. Each experiment (n=4 mice) was evaluated for comparison for vaccination with AZ protein compared with control and for LO protein compared with control; significance evaluated with Student's t test. (B) HLA-A*11:01 transgenic mice survival curve after challenge with Type II parasites. Two weeks after last immunization, the transgenic mice immunized with empty vector, LO DNA+LO polypeptide, or LO polypeptide, or were injected with PBS were infected with 2,000 *T. gondii* ME49-Fluc (Type II) parasites. The survival rates of the 2 groups were recorded. Mice vaccinated with either LO protein alone or LO DNA+LO protein were compared with control mice (PBS or empty vector). Kaplan-Meier curves were generated and survival compared across groups using the log-rank test, P<0.05. (n=8 mice per group in 2 replicate experiments with 4 mice, shown pooled). (C and D) CD8+ memory T cells. Flow cytometry gating for CD8+ memory T cells. Spleen cells are gated on CD3+ CD8+ T cells. Memory T cells were defined as CD44hiCD45RBlo. For each group, a representative FACS plot is shown with the percent of CD8+ memory T cells shown. All mouse experiments were repeated at least twice (n=2-4 mice in each group). * P<0.001, ** P<0.001. In A and D; one-way ANOVA was performed before the Student's t test to determine whether there was an overall difference between the groups.

Prime/Boost Strategy: LO and AZ DNA Plus Multi-Epitope Polypeptide Immunogenicity in Vivo We next addressed whether a prime/boost strategy using DNA encoding the five individual epitopes plus PADRE and the polypeptides would confer better protection against parasite challenge in HLA-A*1101 mice. We constructed synthetic DNAs in which the 5 poly-epitope nucleotides with the N/K alanines or GPGPG (SEQ ID NO: 23) linkers plus PADRE were cloned in EcoRI and BamHI sites of the vaccine vector pMB75.6 (FIG. 6A). During DNA vaccinations, mice were immunized intramuscularly (i.m.) two times at 2 weeks interval with 100 μg of LO or AZ DNA vectors followed by another two injections of 50 μg of the polypeptides at 2 weeks interval. They were challenged with 2,000 ME49 (Fluc) 2 weeks after the last immunization. Brains from these mice were imaged 21 days after the challenge using a Xenogen in vivo imaging system to assess parasite burden in the brain. As shown in FIG. 6B-C, the numbers of luciferase expressing parasites in HLA-A*1101 mice immunized with LO or AZ DNA plus multi-epitope polypeptide or polypeptides alone were significantly reduced compared to the mice immunized with control empty vector or PBS (P<0.02). This correlates with the reduction of the number of cysts per brain (FIG. 6D). We then analyzed the effect of LO or AZ DNA plus multi-epitope polypeptide on IFN-γ expression in vitro. Briefly, mice were immunized two times at 2 weeks interval with LO or AZ DNA followed by another two injections of either LO polypeptide, AZ polypeptide or ovalbumin peptide as control. Negative controls mice were vaccinated twice with empty vector followed by saline. Two weeks after the last immunization, mice were sacrificed and splenocytes were harvested for immune responses analysis. As shown in FIG. 7A, considerable amount of IFN-γ expressing CD8+ cells were observed following immunization with AZ DNA or LO DNA compared with mice immunized with the empty vector. An even more robust response was achieved when mice immunized with the vectors expressing the polypeptides were stimulated in vitro by the corresponding AZ or LO protein, although the difference was only significant in the LO treated mice. In contrast, there was no increase in the amount of CD8+ IFN-γ producing cells observed when the mice were immunized with AZ or LO DNA followed by a challenge with a non-relevant protein, ovalbumin.

LO DNA Plus Multi-Epitope LO Polypeptide are Protective Against Toxoplasma Challenge in HLA-A* 1101 Transgenic Mice As shown in FIG. 7B, a majority, 7 of 8 (87%) HLA-A*1101 mice immunized with LO DNA plus LO polypeptide emulsified in GLA-SE adjuvant survived parasite challenge. In contrast, only 1 of 8 (12%) unimmunized mice or immunized with empty vector survived parasite challenge.

LO DNA Plus Multi-Epitope Polypeptide increases Memory CD8+ T Cell Response

We then analyzed the effect of LO DNA plus multi-epitope polypeptide on the *T. gondii*—specific CD8+ T cell memory response. This was performed by quantifying the levels of memory T cells in the spleen from HLA-A*1101 mice at 35 days after the last immunization. As shown in FIG. 7C-D, CD8+ memory T cells were significantly increased in mice immunized with either LO protein alone or LODNA plus LO protein compared with mice immunized with the empty vector or PBS.

Discussion

There is a need for improved vaccination and delivery approaches to induce cellular immune responses against *T. gondii*. Herein, we present a novel way to present immunogenic peptide epitopes to a host's immune system based on the assembly of five protective CD8+ T cell epitope for HLA-A*1101-restricted supertypes. These epitopes were constructed with the universal CD4+ T cell epitope, PADRE linked with N/KAAA (SEQ ID NO: 21 and 22) or GPGPG (SEQ ID NO: 23) spacers and a secretory signal. These vaccine design features were incorporated to maximize proteasome processing and, subsequently, epitope and vaccine immunogenicity.

Herein, we examined the immunogenicity of a multi-epitope protein and synthetic consensus DNA, clinically approved mammalian expression vector encoding five *T. gondii* specific HLA-A*1101-restricted epitopes. The DNA plasmid vaccine is encoding the five CD8+ T cell epitopes restricted by HLA-A*1101 supertype alleles and the universal HTL epitope, PADRE. These DNA constructs were optimized using codon optimization, leader sequence addition, plasmid production at high concentration and the DNA was delivered by electroporation. Immunization of HLA-A*1101 mice with recombinant multi-epitope formulated with a Toll-like receptor 4 ligand (TLR4)-containing adjuvant (gluco glucopyranosyl lipid adjuvant in a stable emulsion [GLA-SE]) induced antigen-specific IFN-γ-producing CD8+ T cells in their spleens, increase memory CD8+ T cells population, and conferred a potent protection against *T. gondii* challenge. The adjuvant ALUM formulated to the recombinant multi-epitope was less effective in conferring protection as when compared to the vaccine preparations containing GLA-SE. The present study also demonstrated that DNA prime followed by a multi-epitope protein-GLA-SE boost is more protective than either of the DNA prime followed by ovalbumin (unrelated protein) boost or the recombinant multi-epitope alone.

Our present study showed that protein prime and boost with GLA-SE was also quite effective. The ex vivo stimulation of spleen cells from HLA-A*1101 mice and PBMC from HLA-A03 seropositive individuals showed CD8+ T cells were more responsive to the composite polypeptide than to the pooled or single constituent peptides. Processing and presentation of AZ and LO poly-epitope polypeptide in human cells occur with high efficiency in LO poly-epitope-stimulated cells. These cells demonstrate stronger responses with N/K alanines linker compared to GPGPG (SEQ ID NO: 23).

Figure 8:
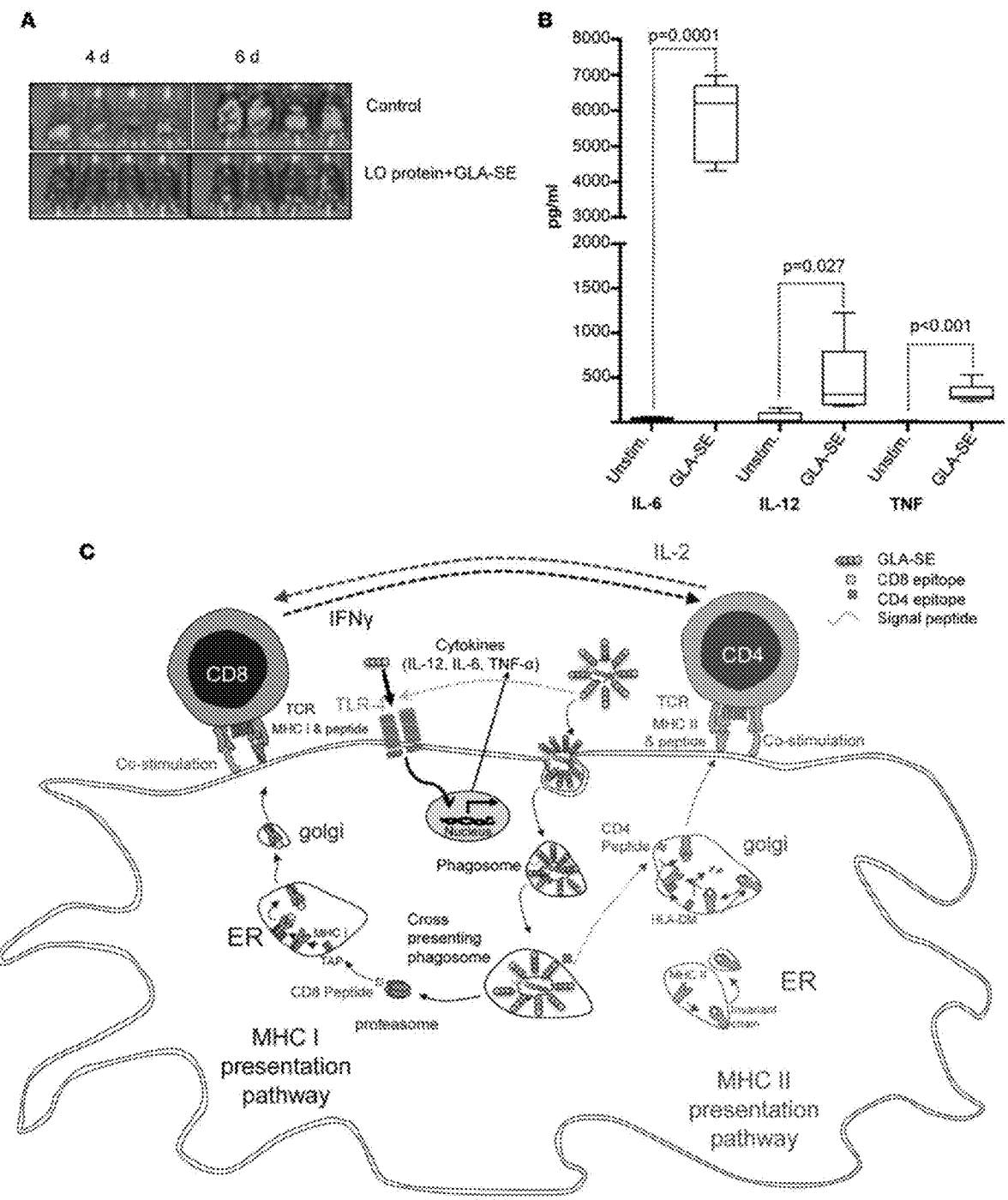
FIG. 8. Multi-epitopes adjuvanted with GLA-SE are captured and presented by MHC molecules on the APCs to T lymphocytes. (A) HLA-A*11:01 transgenic mice immunized with LO protein plus GLA-SE were protected compared with control mice inoculated with PBS when they were challenged with 20,000 *T. gondii* prugneaud strain (Fluc) luciferase expressing parasites after 4 and 6 days. (n=4 mice per group, 2 replicate experiments.) (B) Assay demonstrating that GLA-SE is a TLR4 ligand that leads to production of IL-6, IL-12, and TNF-α by PBMC. Stimulation of human whole blood with GLA-SE. Heparinized whole blood was collected from 6 healthy donors, and 200 µl was stimulated with 5 µg GLA-SE in 96-well plates at 37° C. CO2. After 24 hours, plasma was removed and assayed for IL-6, IL-12(p40), and TNF-α by a custom Luminex-based multiplex immunoassay kit (Affymetrix eBioscience). Data were analyzed using the Masterplex QT software (Miraibio). The cytokine production stimulated by adjuvant was statistically significant for IL-6, IL-12, and TNF-α (P<0.05) compared with the unstimulated groups as assessed by the Mann-Whitney U test (GraphPad Prism software). The plots show median, with box extending from the 25th to 75th percentile and the whiskers extending from minimum and maximum values of the data set. (C) Multi-epitope proteins with GLA-SE are captured by the Antigen-presenting cells (APCs), and the peptides contained are presented by MHC molecules on the APCs to T lymphocytes in both a class I and a class II pathway. This demonstrates that cross presentation into a class I pathway must occur by virtue of effector function. APCs are also activated through recognition of GLA-SE by TLR4 receptors molecules. This activation leads to the production of pro-inflammatory cytokines (IL-12, IL-6, TNF-α) and the expression of costimulatory molecules on the cell surface.

The in vitro and in vivo murine work in the present study indicates that the GLA-SE nano-emulsion must provide protein for cross presentation by antigen presenting cells as shown schematically in FIG. 8. This is a novel and important finding with broad implications for vaccine development when induction of immune responses with protective CD8+ T-cells are critical.

In summary, our study shows a composite protein, with a secretory signal, five CD8+ MHC class I epitopes from *T. gondii*, and PADRE, can be assembled and elicits protective CD8+ T-cells responses. Using HLA-A*1101 transgenic mice, we demonstrate the specificity of 5 HLA-A*1101 restricted epitopes to prime and boost an IFN-γ response. In addition, the recombinant multi-epitope polypeptide emulsified in GLA-SE adjuvant confers more protection and increases memory CD8+ T cell response against *T. gondii* in HLA-A*1101 transgenic mice. It is likely that the GLA-SE emulsion encloses the protein and presents an optimum configuration decorated with the TLR4 ligand GLA that induces a powerful CD8+ and CD4+ T cell immune response (FIG. 8). In addition, DNA encoding the multi-epitope delivered by electroporation and followed by protein boosts is useful for the induction of a strong immune response against *T. gondii*. Thus, our data provide important support suggesting that enhanced electroporation-delivered DNA prime-protein boost, and protein prime protein boost which would be considerably better tolerated, are useful strategies for delivery of a multi-epitope anti- parasite vaccine.

Methods
Bioinformatic Predictions and MHC-Peptide Binding Assays

Protein sequences derived from SAG1, SRS52A, SAG2C, GRA6, and GRA5 were analyzed for CD8+ T cell epitopes based on predicted binding affinity to HLA-A*1101 molecules using algorithms available at the Immune Epitope database (IEDB). Quantitative assays to measure binding of peptides to HLA class I molecules are based on inhibition of binding of radiolabeled standard peptide. Assays were performed as described previously (Sidney, J., et al., Immunome Res, 2008. 4: p. 2). [ ]. Concentration of peptide yielding 50% inhibition of binding of radiolabeled probe peptide ($IC_{50}$) was calculated. Under the conditions utilized, were where [label]<[MHC] and IC50, [MHC], the measured IC50 values are reasonable approximations of the true Kd values.

Human PBMC and ELISpot Assay

PBMC were obtained from individuals seropositive to *T. gondii*, and their HLA haplotype was determined. These cells were processed and cryopreserved as described previously (Tan et al., Vaccine 28(23):3977-89 (Year? Was not listed in references). ELISpot assays with human PBMCs used anti-human IFN-γ mAb (1-D1K) with biotinylated anti-human IFN-γ mAb (7B6-1) with $2 \times 10^5$ PBMCs per well. All antibodies and reagents used for ELISpot assays were from Mabtech (Cincinnati, OH). The PBMC were plated in at least 3 replicate wells for each condition. Results were expressed as number of spot forming cells (SFCs) per $10^6$ PBMCs.

Epitope Peptides

KSFKDILPK (SEQ ID NO: 16) ($SAG1_{224-232}$), STFWPCLLR (SEQ ID NO:) ($SAG2C_{13-21}$), AVVSLLRLLK (SEQ ID NO: 17) ($GRA5_{89-98}$), SSAY-VFSVK (SEQ ID NO: 15) ($SRS52A_{250-258}$), AMLTAFFLR (SEQ ID NO: 18) ($GRA6_{164-172}$) and PADRE-derived universal CD4 helper epitope (AKFVAAWTLKAAA) (SEQ ID NO: 19) were used in the vaccine constructs. GLA-SE adjuvant (TLR4 agonist), synthesized by the Infectious Diseases Research Institute (Seattle, Washington) was used as a stable oil-in-water emulsion with specified epitopes during immunization.

Multi-Epitope DNA Vaccine Design

Figure 3:
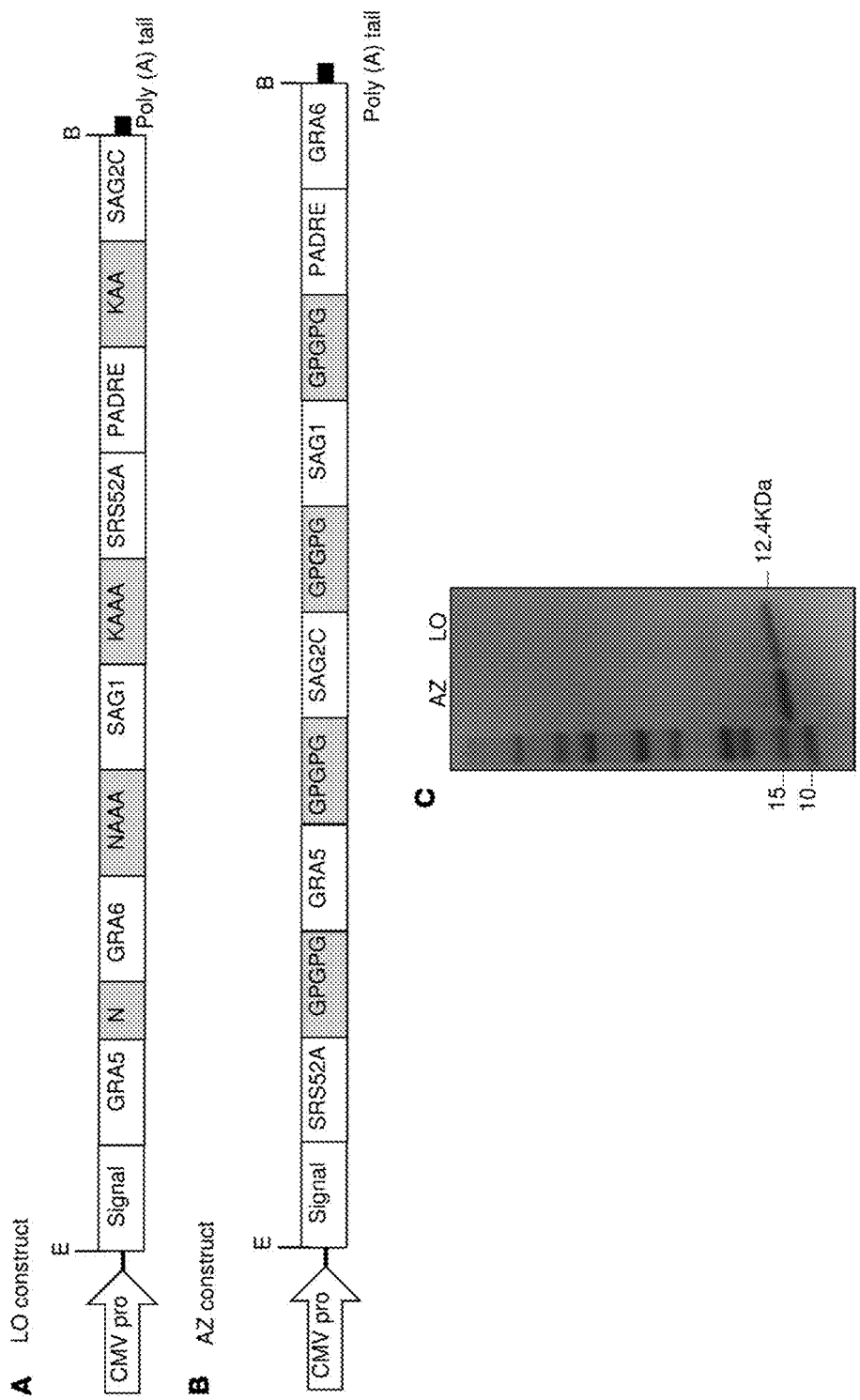
FIG. 3. Schematic diagram of the DNA vaccine construct. (A and B) The orientation of the HLA-A*11:01—restricted CD8+ T cell epitopes and PADRE in the synthetic gene is shown with 2 different types of spacers, called LO and AZ, for N/KAAA and GPGPG (SEQ ID NO: 23) linker, respectively. (C) SDS-PAGE 4%-20% of the purified LO and AZ proteins.
Figure 4:
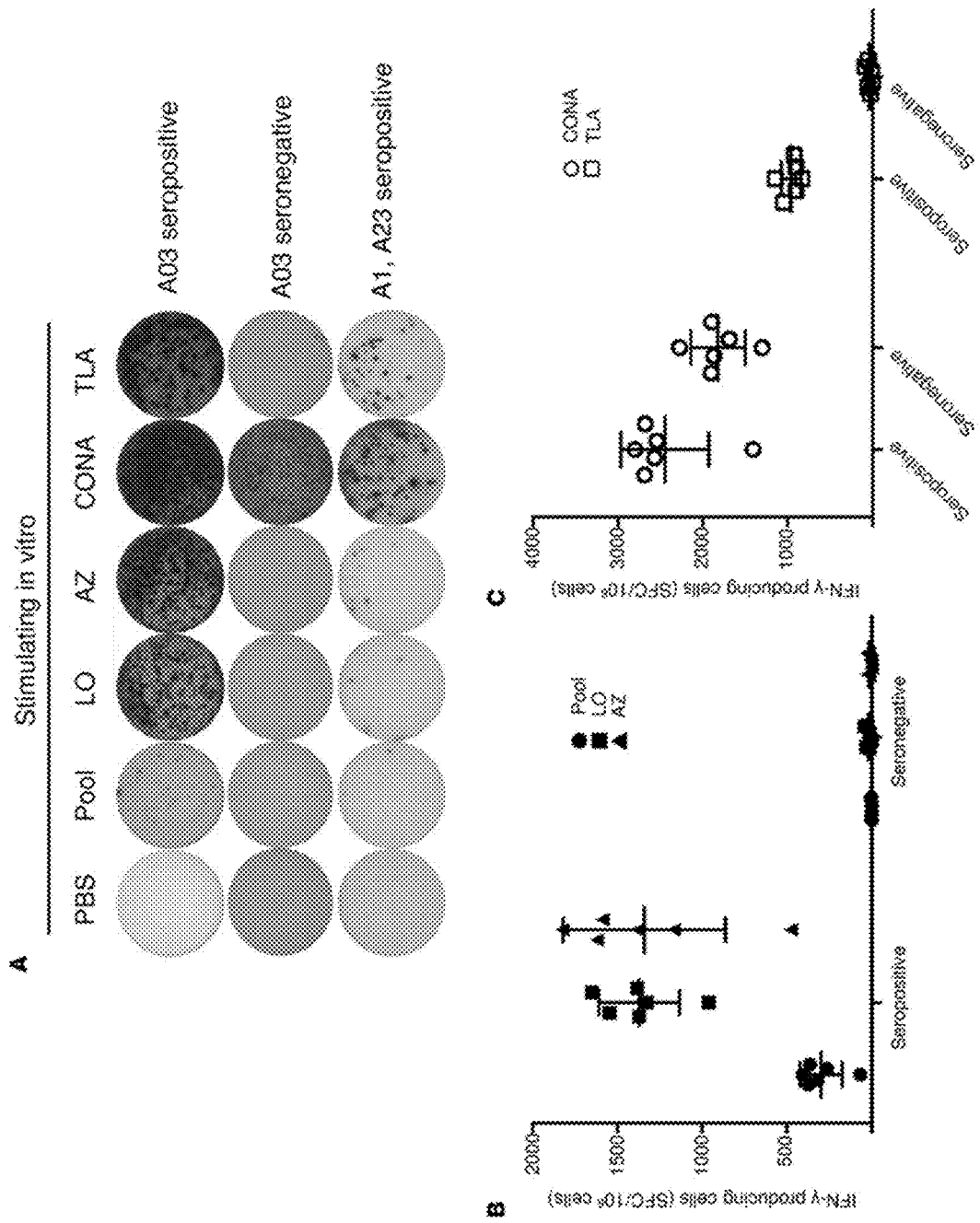
FIG. 4. LO and AZ elicit specific immune responses in HLA-A03 seropositive and seronegative donors. (A-C) ELISpot showing IFN-γ spot formation. PBMCs were tested using LO, AZ, and pool of peptides. (C) Con A and TLA were used as controls. Variability between determinations for single donors are shown in panels A and B with n=6 determinations (as described in FIG. 1). In A and B, the data shown are a single representative experiment from one *T. gondii* seropositive and one *T. gondii* seronegative HLA-A03-supertype donor. Each experiment was carried out with 6 determinations. Replicate experiments also were performed 3 times with PBMCs from 3 *T. gondii* seropositive and 3 *T. gondii* seronegative HLA-A03 individuals. Two-tailed Student's t test was used for statistical analysis comparing differences between the 2 groups (n=3 per group, P<0.05). One-way ANOVA was performed before the Student's t test to determine whether there was an overall difference between the groups. Differences between the stimulation of seropositive and seronegative individuals' PBMCs by the poly-epitope proteins were significant (P<0.05, data not shown). Similarly, TLA stimulated the seropositive persons' PBMCs, but Con A did not (data not shown).

To maximize epitope immunogenicity in vivo, the peptides encoding minigene included starting codon ATG and the mouse Ig k signal sequence at the 5' end of the construct, and spacer sequences N/AAA (SEQ ID NO: 21) (LO construct) and GPGPG (SEQ ID NO: 23) (AZ construct) residues flanking the C-terminus of all epitopes (FIGS. 3 A-C). Whereas the former facilitates processing of the CTL epitopes in the ER, the latter favors proper proteasomal processing and prevents the formation of junctional HLA epitopes. The order of the CTL and HTL epitopes in the minigene and type of spacer sequences that favor proper proteasomal cleavage were determined by a customized computer software program (Epimmune) that identifies the most favorable sequence for epitope processing and simultaneously minimizes the creation of new junctional HLA-A11 determinants.

Purification of Multi-Epitope Protein Vaccine

LO and AZ DNA were PCR-amplified and cloned in the expression vector pET-22 (Novagen). The multi-epitope protein was expressed in the *Escherichia coli* BL21-Codon-Plus strain (Stratagene). Expression clones were grown at 37° C. in Luria broth medium containing 50 μg/μl kanamycin and 34 μg/μl chloramphenicol. A 1-liter culture of *E. coli* was grown to an $A_{600}$ of 0.6, and protein expression was induced by addition of isopropyl-β-D-thiogalactopyranoside (1 mM final concentration). Recombinant protein was extracted under native conditions by using the BugBuster protein extraction reagent (Novagen, 6 ml/g of cell pellet) containing a protease inhibitor mix (Roche Diagnostics) and 10 μg/ml lysozyme. All purification steps were performed under 8 M urea denaturing conditions. The His-tagged polypeptides were purified by using nickel-affinity chromatography and followed by Q-Sepharose, which used to capture the endotoxin. The eluate, which contains 8 M urea, was dialyzed against a buffer containing 5 mM Hepes-KOH (pH 7.8) and 0.5 mM DTT. The purity of the protein was determined by SDS-PAGE, and the protein concentration was measured by the method of Bradford using BSA as a standard. Using E-TOXATE Kits (Sigma-Aldrich, USA), endotoxin concentration in these proteins is <25 EU/ug of protein.

Plasmid and Gene Cloning of Multi-Epitopes DNA Vaccine Construct

The clinically approved mammalian expression vector pMB75.6 (from Inovio Pharmaceuticals, Blue Bell, PA) was used as a DNA vaccine vector. Briefly, the plasmid contains elements essential for expression in mammalian cells: a cytomegalovirus (CMV) promoter, intron, and gene of interest followed by the simian virus 40 (SV40) polyadenylation signal.

The oligonucleotides of 5 individual *T. gondii* peptides shown in Table 1 plus PADRE-derived universal CD4 helper epitope were linked with different spacers and synthesized using 9 overlapping 50-nucleotide oligonucleotides. LO and AZ were first assembled and amplified as three small fragments that were subsequently used as templates to amplify the whole gene. The full-length constructs were cloned into the vaccine vector pMB75.6 using EcoRI/BamHI restriction sites. Neither the pMB75.6 vector backbone nor the epitope-encoding region shares significant homology with known human genomic sequences. All recombinant plasmids were propagated in *Escherichia coli* TOP10 and confirmed by restriction analysis and PCR sequencing. Large-scale plasmid DNA was prepared using the endotoxin-free Mega kit according to the manufacturer's instructions (Qiagen, Hilden, Germany), and the DNA concentrations were determined by A260/A280 absorption measurements. Plasmid DNA was dissolved in sterile endotoxin-free PBS and stored at −20° C. until use.

Mice

HLA-A*1101/$K^b$ transgenic mice were produced at Pharmexa-Epimmune (San Diego, CA), embryo-rederived at Taconic and JAX laboratories and bred at the University of Chicago. These HLA-A*1101/$K^b$ transgenic mice express a chimeric gene consisting of the $1^{st}$ and $2^{nd}$ domains of HLA-A*1101 and the $3^{rd}$ domain of H-$2K^b$, and were created on a C57BL/6 background. Mice were maintained in SPF conditions throughout. All studies were conducted with the approval of the Institutional Animal Care and Use Committee at the University of Chicago.

Immunizations of Mice and Challenge

To evaluate multi-epitope protein immunogenicity, HLA-A*1101 transgenic mice were inoculated subcutaneously (s.c.) at the base of the tail using a 30-gauge needle with 50 μg LO or AZ recombinant protein emulsified in 20 μg of GLA-SE (TLR4 agonist) three times at two weeks intervals. For immunization by DNA, mice were inoculated by injection of 50 μl of PBS containing 100 μg of DNA into each quadriceps muscle using a G26 gauge needle at weeks 0, 2 and 4. In a bid to enhance delivery of DNA, we used an electroporation device. Briefly, following injection of DNA, the surface dermal device was applied to the site of injection. The array was "wiggled" at the injection site to ensure good contact and electro-transfer achieved through pulse generation from the ELGEN 1000 (Inovio Pharm., San Diego) pulse generator. The parameters used were three 15 V pulses of 100 ms duration. Negative control mice were vaccinated with 100 μg empty vector or 50 μl saline. For challenge studies, immunized mice were challenged intraperitoneally (i.p.) 14 days post-immunization using 10,000 *T. gondii* ME49-Fluc (Type II) parasites that express firefly luciferase.

ELISpot Assay to Determine Immune Responses with Murine Splenocytes

Mice were euthanized 14 days after immunization. Spleens were harvested, pressed through a 70 μm screen to form a single-cell suspension, and erythrocytes were lysed with AKC lysis buffer (160 mM $NH_4Cl$, 10 mM $KHCO_3$, 100 mM EDTA). Splenocytes were washed twice with Hank's Balanced Salt Solution (HBSS) and resuspended in complete RPMI medium (RPMI-1640 supplemented with 2 mM L-GlutaMax (Life technologies). Murine ELISPOT assays were performed using anti-mouse IFN-γ mAb (AN18) and the biotinylated anti-mouse IFN-γ mAb (R4-6A2) and 2.5-5×$10^5$ splenocytes were plated per well. All antibodies and reagents used for the ELISPOT assay were obtained from Mabtech (Cincinnati, OH). Cells were plated in at least 3 replicate wells for each condition. Results were expressed as the number of spot forming cells (SFCs) per $10^6$ murine splenocytes.

In Vivo Bioluminescence Imaging for Determining Outcomes of Challenge with Type II Parasites Mice infected with 2,000 *T. gondii* ME49-Fluc (Type II) tachyzoites were imaged 21 days post-challenge using the in vivo imaging system (IVIS; Xenogen, Alameda, CA). Mice were injected retroorbitally with 200 μl (15.4 mg/ml) of D-luciferin, anesthetized in an $O_2$-rich induction chamber with 2% isoflurane, and imaged after 12 minutes. Photonic emissions were assessed using Living image® 2.20.1 software (Xenogen). Data are presented as pseudocolor representations of light intensity and mean photons/region of interest (ROI). All mouse experiments were repeated at least twice.

Enumeration of Cysts in Mouse Brains following Type II Parasite Challenge

Mice were euthanized at 21 days after infection with 10,000 of Me49-Fluc, and brains were collected, homogenized with 1 ml of saline (0.85% NaCl). Tissue cysts were counted microscopically in 50 μl of the homogenate, and the count was multiplied by 20 to obtain the number of tissue cysts per brain. This number was confirmed by staining brain cysts with fluorescein-labeled *Dolichos biflorus* agglutinin (Vector Laboratories) and quantitation using fluorescence microscopy.

Flow Cytometry.

Splenocytes were manually processed using 70 μm filters in DMEM media supplemented with 5% FCS and red blood cells were lysed with ACK lysis buffer. Cells were stained with CD3 APC (145-2C11), CD4 PE (GK1.5), CD8 PerCP (53-6.7), and CD44 AF780 (IM7), CD45RB FITC (C363.16A). All antibodies were purchased from eBioscience (San Diego, CA). Memory T cells were defined as $CD44^{hi}CD45RB^{lo}$. All flow cytometry data was collected on LSRII flow cytometer (BD Biosciences, San Jose, CA) and analyzed using FlowJo software 10.0 (Tree Star, Ashland, OR).

Statistical Analyses

Data for each assay were compared by One-way ANOVA or a Student t test using GraphPad Prism 5 software (GraphPad Software, San Diego, CA). Differences between the groups were identified by ANOVA and multiple comparison procedures, as we previously described [6]. Data are expressed as the means ±SD. Results were considered to be statistically significant at p<0.05.

Study Approval

Experiments and handling of mice were conducted under federal, state, and local guidelines under an IACUC protocol and with approval from the University of Chicago IACUC. Institutional Review Board (IRB) approval was obtained at the University of Chicago for this study. This study also is in compliance with all Health Insurance Portability and Accountability Act of 1996 (HIPAA) regulations.

Example 2. Novel Protein Nanovaccine Confers Robust Immunity Against *Toxoplasma*

We designed and produced a self-assembling protein nanoparticle (SAPN) containing five CD8+ HLA-A03-11 supertypes restricted epitopes from antigens expressed during *Toxoplasma*'s lifecycle, PADRE which is a CD4+ T cell, universal epitope, and flagellin as scaffold and TLR5 agonist. These epitopes were separated by N/KAAA (SEQ ID NO: 21 & 22) spacers and optimized for proteasomal cleavage. SAPN-GLA-SE was evaluated for its efficacy in inducing IFN-γ and protection against *T. gondii* in mice with an HLA-A*1101 transgene. In our data, immunization with SAPN adjuvanted with TLR4 ligand-emulsion (GLA-SE), activated CD8+ T cells to produce IFN-γ. SAPN-GLA-SE also protected against subsequent challenge with type II parasites in mice with an HLA-A*1101 transgene. Hence, combining CD8+ T cell-eliciting peptides and PADRE into a multi-epitope within a single self-assembling protein, administered with adjuvant GLA-SE, leads to efficient presentation by MHC Class I and II. Furthermore, these results suggest that activation of TLR4 and TLR5 could be useful for development of T cell vaccines to prevent toxoplasmosis in humans.

In the present study, five epitopes from the surface antigen (SAG1), the dense granule proteins (GRA3 and GRA6), the surface antigen-1-related sequences (SRS52A), which bind to HLA-A11-01 were evaluated for their efficacy as a SAPN-vaccine in HLA-A11-01 transgenic mice. In these constructs, the CD8+ HLA-A03-11 supertypes restricted epitopes were linked by N/KAAA (SEQ ID NO: 21 and 22) spacers and conjugated with PADRE, a universal CD4+ helper T lymphocyte epitope. PADRE binds promiscuously to MHC class II variants, augments effector functions of CD8+ T cells by producing IL2, which augments induction of CD4+ T helper cells (Brown, et al., *Journal of immunology* 145, 3438-3441 (1990); Gazzinelli, et al. *Journal of immunology* 146, 286-292 (1991)). Epitopes eliciting both CD4+ and CD8+ T cells are important components in the formulation of successful vaccines by driving a protective response. Our data herein show that incorporating this peptide into the SAPN protein constructs and delivering this in TLR4 ligand emulsion adjuvant (GLA-SE), resulted in activation of CD8+ T cells. This led these cells to produce IFN-γ. They thereby protected against subsequent challenge with type II parasites given as a high inoculum. Thus, our work highlights the potential for the use of SAPN as a platform for the delivery of CD8+ and CD4+ -restricted epitopes, in adjuvant formulation to protect against toxoplasmosis.

Results

Preparation and Characterization of CD8-SAPN and Empty-SAPN. The SAPN constructs were expressed, purified and folded to form nanoparticles. The protein has a relative molecular weight of about 48 kDa on a SDS-PAGE (data not shown). Transmission electron microscopy (not shown) showed a relatively uniform distribution of non-aggregated nanoparticles of ~30 nm in diameter.

Figure 9:
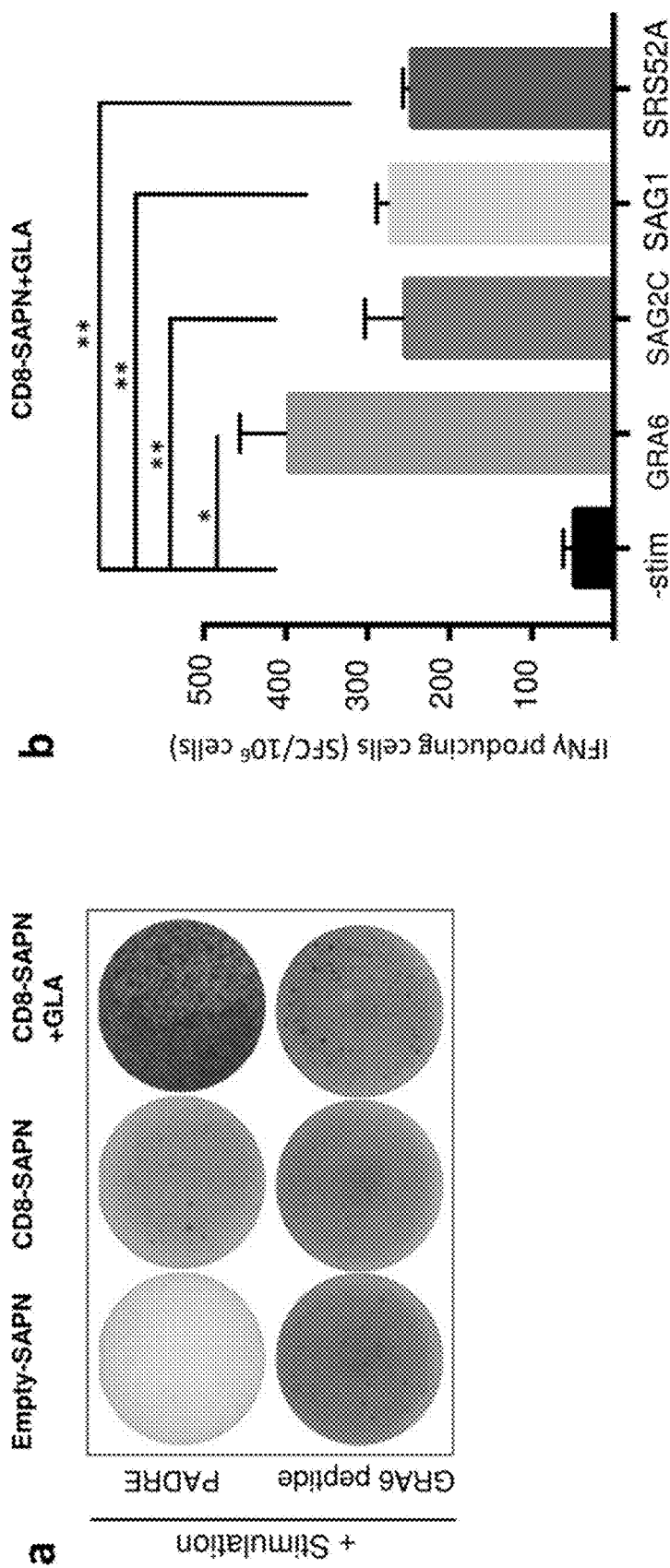
FIG. 9: CD8-SAPNs elicit restricted CD8$^+$ T and CD4$^+$ T cell peptide-specific immune response. ELISpot showing IFN-γ spot formation. Mouse splenocytes from Empty-SAPN, CD8-SAPN, and CD8-SAPN+GLA were tested using GRA6 peptide (GRA6$_{164-172}$) or PADRE. All peptides elicited IFN-γ (p<0.05) compared to unstimulated cultures. Pooled peptides appeared additive. The greatest effect occurred with the polypeptide as also occurred in earlier studies[23]. *=p<0.05.
Figure 10:
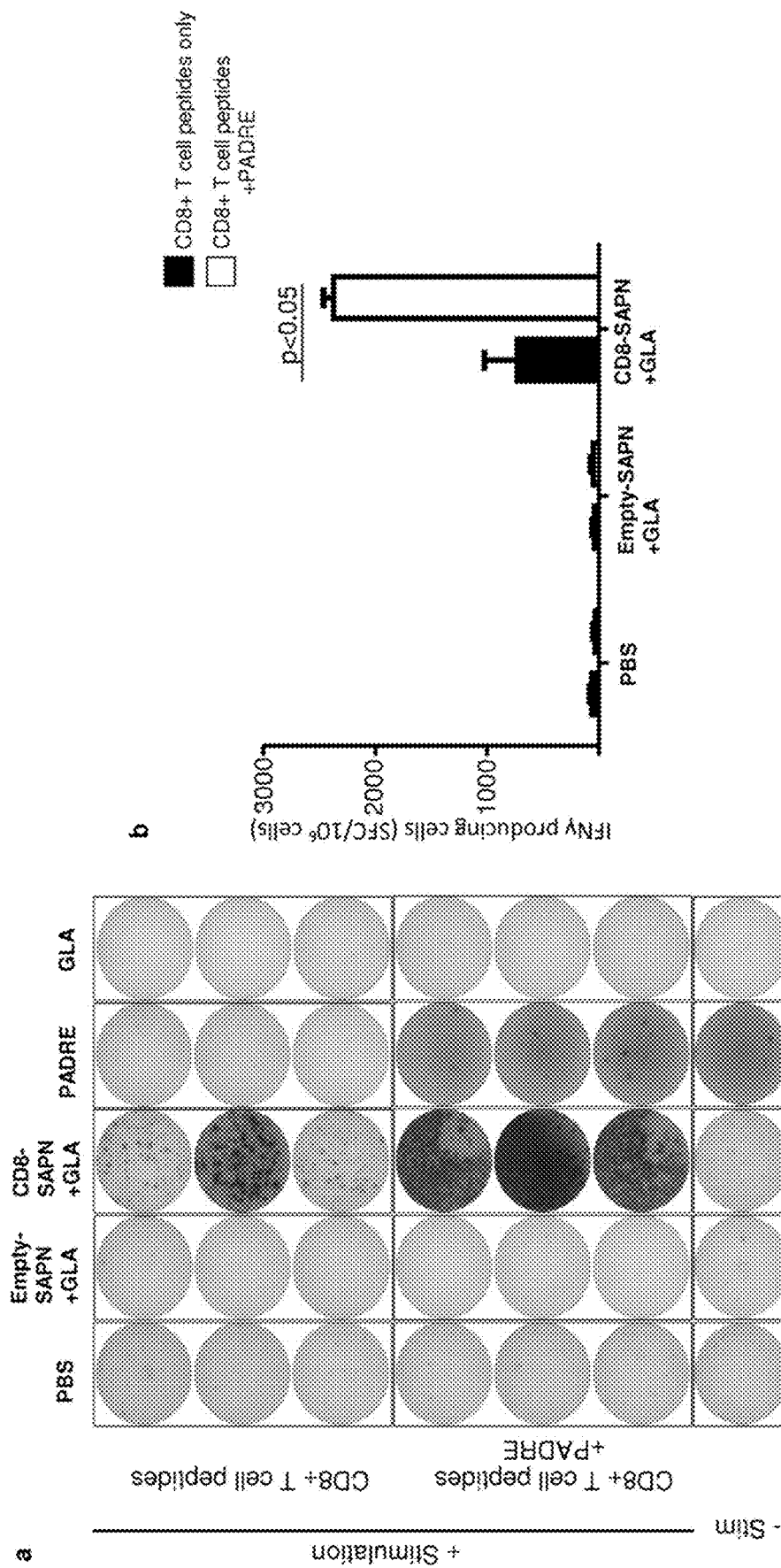
FIG. 10: CD8-SAPNs are potent inducers of cell-mediated immune. a) IFN-γ ELISpot assay stimulated with a group of 5 peptides HLA-A*1101. b) Graph shows the count of spots for splenocytes of untreated, Empty-SAPN+GLA1 CD8-SAPN+GLA group of mice. *=p<0.05 for all IFN-γ ELISpots compared to controls.

In vivo Immunogenicity of CD8-SAPNs. Mice with HLA-A*1101-transgenes were immunized. Immunogen was CD8-SAPNs combined with GLA-SE adjuvant. Immunizations were given three times intramuscularly at two week intervals. Empty-SAPNs plus GLA-SE adjuvant and PBS were used as control. Immunogenicity of the CD8-SAPNs plus adjuvant compared to the Empty-SAPN plus adjuvant were compared in immunized mice with HLA-A*1101 transgenes as described, Spleen cells were obtained from immunized HLA-A*1101 transgenic mice two weeks after final immunization. IFN-γ when cultured with the pool of peptides. FIG. 9 shows IFN-γ secretion is high in mice immunized with CD8-SAPN plus GLA-SE under stimulation either of PADRE or GRA6 peptide. The other peptides also elicited IFN-γ response. The best response, was with the polyepitopes. FIG. 10*a-b* indicate IFN-γ secretion was significantly enhanced by immunization with HLA-A*1101-restricted peptide epitopes eliciting CD8+ T cells and not with Empty-SAPN or PBS when cells are stimulated with HLA-A*1101-restricted peptide epitopes that elicit CD8+ T cells. Significantly more IFN-γ secretion was observed when cells are stimulated with pool of peptides plus PADRE. Thus, the association of CD8+ T cell and CD4+ T cell restricted peptides contributes to IFN-γ production in mice with HLA-A*1101 transgenes.

Figure 11:
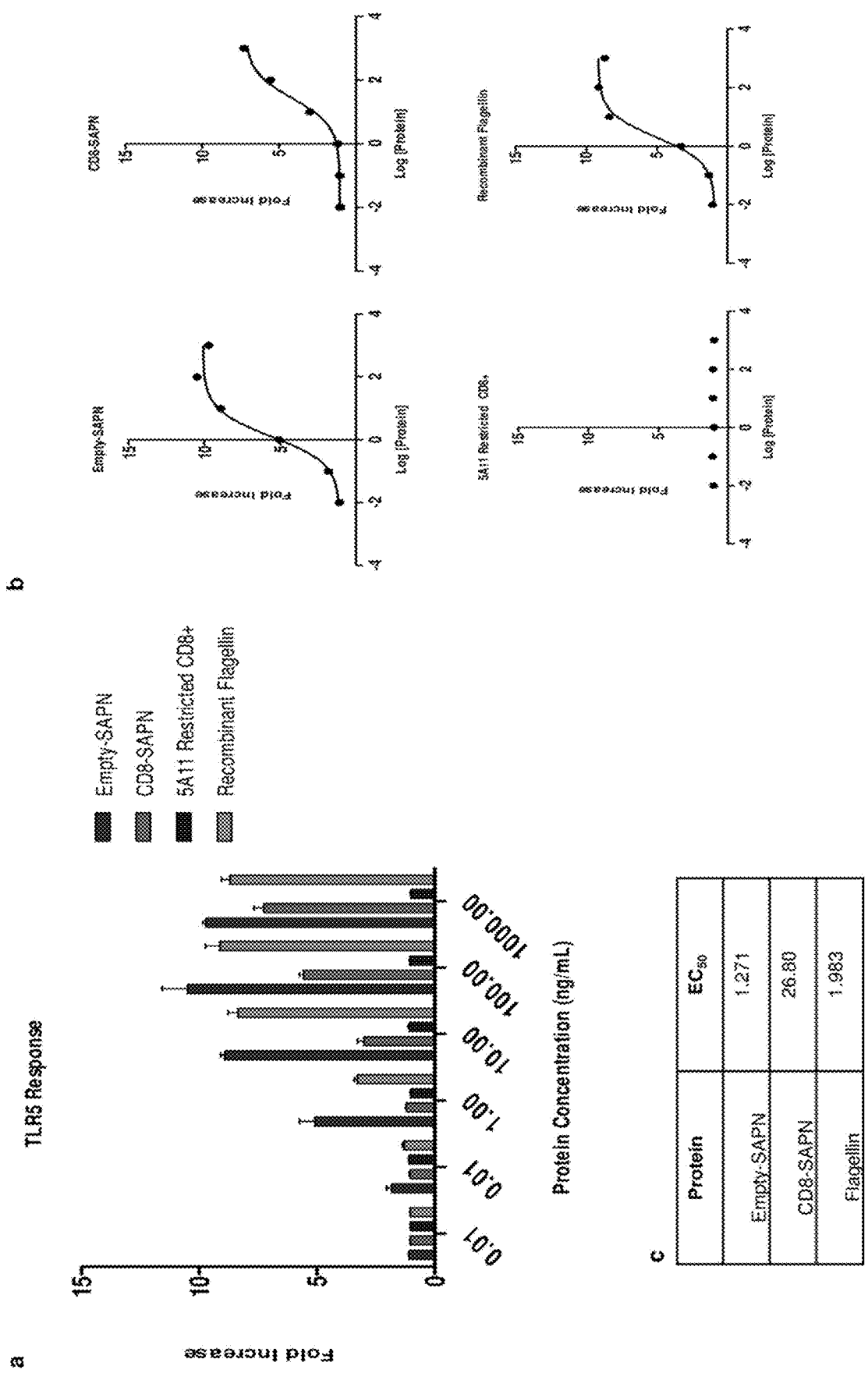
FIG. 11: SeaPorter TLR5 cell-line was exposed to varying concentrations of each indicated protein, and the level of TLR5 stimulation was determined by the level of SEAP expression. Fold increase in SEAP expression for each protein sample over non-treated controls, error bars are standard error of the means. A two-way ANOVA model was fit with protein concentration and type as factors. There was a significant protein concentration by type interaction (p<0.001); this indicated that the differences across types depended on the concentration and that the differences across concentrations varied by type. Specifically, there weren't statistically significant differences across types at the two lowest concentrations (0.01 and 0.1), but there were significant differences between types at the 1, 10, 100, and 1000 ng/mL concentrations (p<0.001 for all). Subsequent pairwise contrasts at these 4 concentrations found that the 5A11 Restricted CD8+ group (the recombinant protein without flagellin) was significantly different from the other 3 groups in all cases except for the 5A11 Restricted CD8+ vs. CD8-SAPN comparison at the 1 ng/mL concentration. In addition, at each of these 4 concentrations, the Empty-SAPN was significantly different (greater than) from the CD8-SAPN. And as expected, there was a significant concentration effect for all protein types (p<0.001) except 5A11 Restricted CD8+ (p>0.9).

In vitro TLR5 Stimulation. SeaPorter™ TLR5 cell-line was exposed to varying concentrations. The concentrations used in ng/ml were 0.01, 0.1, 1, 10, 100, 1000 of Empty-SAPN that don't contain the CD8+ epitopes but still have flagellin, CD8-SAPN containing the polypeptide with the five restricted CD8+, epitopes, and recombinant flagellin (as control). The level of TLR5 stimulation was determined by the level of SEAP expression. Fold increase in SEAP expression for each protein sample over non-treated controls. As shown in FIG. 11A-C, TLR5 activity was significantly enhanced in the Empty-SAPN and the CD8-SAPN and not in the control polypeptide. Surprisingly, flagellin in Empty-SAPN particles have higher TLR5 activity than recombinant flagellin alone.

Figure 12:
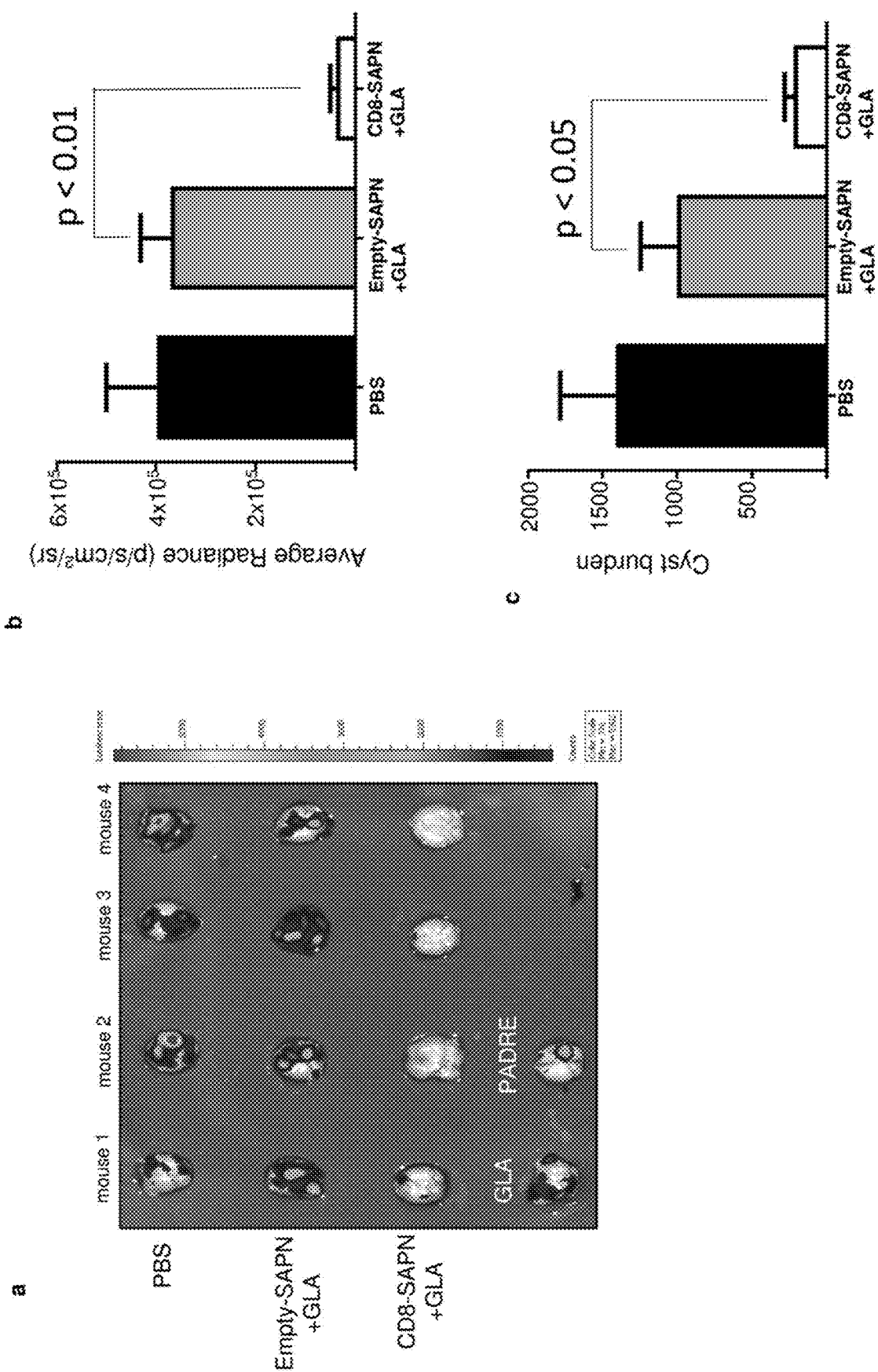
FIG. 12: *T. gondii* brain cysts luciferase expression was significantly reduced in immunized HLA-A*1101 mice. HLA-A*1101 transgenic mice were immunized with GLA-SE adjuvanted Empty-SAPN or CD8-SAPN three times at intervals of two weeks. PBS was used as control. a) *T gondii* brain cysts luciferase expression was significantly reduced in HLA-A*1101 mice immunized with CD8-SAPN plus GLA boost at 21 days after challenge with 2000 Me49 (Fluc) *T. gondii* expressing luciferase. b) Xenogen imaging of brain ex vivo following the injection of luciferin into the retro-orbital plexus and then exposure of the brain to luciferin solution. This figure shows data from mice in one of the replicate experiments (n=4 control and 4 immunized mice). c) Enumeration of cyst was performed with brains of mice challenged 21 days after final immunization. SAPN reduced cyst numbers and luminescence (p<0.05).

SAPN with GLA-SE Adjuvant Confer Robust Protection Against *T. gondii* in mice with HLA-A*1101 Transgenes. We immunized mice by administering either CD8-SAPN with GLA-SE adjuvant or Empty-SAPN with GLA-SE adjuvant, adjuvants alone, PADRE alone, saline and then challenged two weeks after the last immunization with type II strains of *T. gondii*. Brains from these mice were imaged. This xenogen camera imaging took place 21 days challenge with 2,000 Me49-Fluc . This was in vivo imaging system by Xenogen. FIG. 12A-B luminescence in mice that were immunized with CD8-SAPN plus GLA-SE were significantly lower when they were compared with mice immunized with control Empty-SAPN plus GLA-SE, GLA-SE alone, PADRE alone, or PBS. This correlates with the reduction of the number of cysts per brain in CD8-SAPN plus GLA-SE adjuvant mice (FIG. 12*c*).

Discussion

Our capability to control the ability of peptides and proteins to self-assemble into particles well-defined size a shape allows us to design mechanically and chemically stable. Since the SAPNs resemble virus capsids they combine strong immunogenic effect of live attenuated vaccines with high specificity in eliciting immune responses of protein-based vaccines. It is apparent that the SAPN have a great potential to serve as a platform for vaccines beyond their ability to repetitively present antigens. In contrast to live attenuated vaccines, SAPN-derived vaccines pose no risk of infection. They are very versatile and flexible in their design leading to better biophysical and immunological properties. Furthermore, of bacterial protein expression, purification, and self-assembly into nanoparticles reduces time large-scale production.

Here we used the SAPNs to present immunogenic peptide epitopes to a host's immune system based on the assembly of five protective CD8+ CTL HLA-A03-11 restricted supertypes with PADRE in a SAPN. All epitopes were flanked at the carboxy-terminus by N/KAAA (SEQ ID NO: 21 and 22) spacers, which promote optimally immunogenic processing. Our data show potent immunogenicity (high IFN-γ secretion) when splenocytes were stimulated in vivo by these peptides. We found flagellin in a SAPN made protection against influenza much more robust. In the TLR5 activity assay the SAPN shows good stimulation, however, the activity is reduced compared to the Empty-SAPN. There might be some interference with TLR5-binding and the presentation of the CD8+ restricted epitopes as the CD8+ epitopes string was engineered into the flagellin molecule to replace the D2 and D3 flagellin domains.

In the work with this new SAPN-design herein, the flagellin molecule itself serves as a scaffold for the *T. gondii* peptides, while the flagellin molecule itself is an integral part of the SAPN scaffold, with or without the A11 CD8+ epitopes. This SAPN scaffold lacking the CD8+ epitopes conferred only a small amount of protection compared with the scaffold with the inclusion of the A11 peptides. It is not possible to create a relevant separate control without flagellin because in this scaffold the HLA A11 binding peptides are intercalated into the flagellin molecule itself. As can be seen in FIG. 1, these A11 peptides are an integral part of the flagellin molecule within the SAPNs. The inclusion of flagellin also serves as a potential adjuvant.

In summary, our study shows a self-assembling protein nanoparticle, with five CD8[+] MHC class I epitopes from *T. gondii* and PADRE, can be assembled. Using HLA-A*1101 transgenic mice, we demonstrate that the SAPN emulsified in GLA-SE adjuvant elicits a protective MHC class I response. Thus, our work indicates a novel improved assembly of peptides for cross presentation of CD8[+] T cell eliciting epitopes in vaccines to prevent toxoplasmosis.

Materials and Methods

Peptides. KSFKDILPK (SEQ ID NO: 16) (SAG1$_{224\text{-}232}$), STFWPCLLR (SEQ ID NO: 14) (SAG2C$_{13\text{-}21}$), AVVSLLRLLK (SEQ ID NO: 17) (GRA5$_{89\text{-}98}$), SSAYVFSVK (SEQ ID NO: 15) (SRS52A$_{250\text{-}258}$), AMLTAFFLR (SEQ ID NO: 18) (GRA6$_{164\text{-}172}$)[23] and PADRE, a universal CD4[+] helper epitope (AKFVAAWTLKAAA) (SEQ ID NO: 19) were used in the vaccine constructs. Infectious Diseases Research Institute (Seattle, Washington) synthesized the TLR 4 agonist adjuvant called GLA-SE. This was prepared and used as a stable oil-in-water emulsion.

Molecular Biology. The methods using DNA coding for the nanoparticle constructs were similar to those described in our earlier work[18]. Briefly, they were prepared using standard molecular biology procedures. Specifically, plasmids containing the DNA coding for the protein sequence were used[18]. They were constructed by cloning into restriction sites in the SAPN expression plasmid[18]. We used a SAPN construct we had developed and described earlier (Babapoor, S. et al. *Influenza research and treatment* 2011, 126794, doi:10.1155/2011/126794 (2011)). Briefly, this construct is composed of a pentameric coiled-coil tryptophane zipper. This zipper is linked by a glycine residue to a trimeric de-novo designed leucine zipper coiled coil. In this construct, a flagellin construct composed of the D0 and D1 domains (residues 1-177 and 249-372) of *Salmonella enterica* flagellin from the structure with pdb-code 3V47 from the RCSB protein data bank is used to extend the protein chain at the C-terimnus[18] (FIG. 1).

The CD8[+]-peptide sequence AVVSLLRLLKNAMLTAFFLRNAAAKSFKDILPKKAAASSAYVFSVKKAAAKFVAA W TLKAAAKSTFWPCLLR (SEQ ID NO: 36) with the five CD8[+] epitopes also containing PADRE was next inserted into the D1 domain of flagellin. This polypeptide completely replaces the D2 and D3 domains to generate the so-called CD8-SAPN. Overall, the positive charge of this epitope string is balanced with stretches of negative charges at both ends of the epitope sequence. Our Empty-SAPN was generated using the short linker KYKDGKGDDK (SEQ ID NO:38) to replace the D2 and D3 domains of flagellin.

Protein Expression. This was performed as performed and described in Babapoor et al: Plasmids were transformed into *Escherichia coli* BL21 (DE3) cells. *E. coli* were grown at 37° C. in Luria broth with ampicillin. We induced expression using isopropyl β-D-thiogalacto-pyranoside. Cells were removed from 37° C. four hours after induction. They were harvested by centrifugation at 4,000×g. We stored cell pellet at −80° C. We then thawed the cell pellet, keeping this on ice. We then suspended this in a lysis buffer consisting of 9 M urea, 100 mM NaH$_2$PO$_4$, 10 mM Tris pH 8, 20 mM imidazole, and 0.2 mM Tris-2-carboxyethyl phosphine (TCEP). Sodium dodecyl sulfate polyacrylamide gel electrophoresis (SDS-PAGE) was used to assess our protein expression level.

Protein Purification. The same methodology as used in Babapoor, S. et al. was used herein. Briefly, sonication was used to lyse cells. Briefly, centrifuging at 30,500×g for 45 min[18] was used to clear our lysate. Then, for at least 1 hour, our cleared lysate was incubated with Ni-NTA Agarose Beads (Qiagen, Valencia, CA, USA). Then, first the column was washed with lysis buffer. This was then followed by a wash with a buffer containing 9 M urea, 500 mM NaH$_2$PO$_4$, 10 mM Tris pH 8, 20 mM imidazole, and 0.2 mM TCEP. A pH gradient was used to elute our protein. This pH gradient for elution was created as follows: 9 M urea, 100 mM NaH$_2$PO$_4$, 20 mM citrate, 20 mM imidazole, and 0.2 mM TCEP. Subsequent washes were performed as follows: at pH 6.3, 5.9, and 4.5. After the pH gradient, to further elute the protein, we used a gradient of lysis buffer with increasing imidazole concentration.

Protein Refolding. We used methodology described in Babapoor, S. et al. Specifically, for refolding, the protein was first rebuffered to the following conditions: 9 M urea, 20 mM Tris pH 8.5, 50 mM NaCl, 5% glycerol, 2 mM EDTA. Four µl of a solution with a concentration of 1.8 mg/ml protein was added to the same buffer solution without urea to a final concentration of 0.05 mg/ml for quick refolding of a first screen. We used this because this quick dilution from denaturing (urea) to native (no urea) buffer conditions triggers refolding of protein. We then used negative stain transmission electron microscopy at different resolutions to analyze our solution. We then used further screens for optimal refolding conditions. These were performed with smaller sampling sizes of the pH and ionic strength.

In vitro TLR5 Response Assay. Activation through TLR5 was assessed for SAPN as described in Karch, et al. *Nanomedicine*, doi:10.1016/j.nano.2016.08.030 (2016)). Testing was done using TLR/NF-κB/SEAPorter™ Stably Transfected HEK 293 Cell Lines as follows: All cell lines were stably co-transfected cell lines. They express TLR5 and secreted alkaline phosphatase (SEAP) reporter gene under transcriptional control of an NF-κB response element. Fourteen thousand cells per well were seeded in a 96 well plate at passages 5-9. Twenty-four hours later, we removed growth media. Growth media was replaced with DMEM high glucose (Hyclone, Logan, UT). This contained either a SAPN, or recombinant flagellin (Novus Biologicals, Littleton, CO), 0.1, 1, 10, 100, 1000 ng/mL in triplicate. Media alone was present in control wells. Wells were exposed for 24 hours. Then supernatant was collected. Supernatant was used to determine whether secreted alkaline phosphate was present. This was determined with a Reporter Assay kit for secreted alkaline phosphates (Novus Biologicals, Littleton, CO). This was done using the manufacturer's instructions. Media only controls were used to normalize SEAP activity. This was used to determine each construct's EC50. Triplicate determinations were utilized for each experimental condition.

Mice. HLA-A*1101/K$^b$ transgenic mice were created and then bred/produced at Pharmexa-Epimmune (San Diego, CA). They were then embryo-rederived at Taconic and JAX laboratories. Colonies were then expanded and they were then maintained and produced in isolators at the University of Chicago. These mice express a chimeric gene called HLA-A*1101/K$^b$ transgene. This chimeric gene consists of the 1st and 2nd domains of HLA-A*1101 and the 3rd domain of H-2K$^b$. Mice were maintained in SPF conditions throughout. All of our studies were performed with the Institutional Animal Care and Use Committee at the University of Chicago's review, approval, and oversight.

Immunizations of Mice and Challenge. To assess the immunogenicity of the SAPNs, mice with the HLA-A*1101 transgene were inoculated intramusculary (i.m.). In this injection, 20 µg SAPN was emulsified in the TLR4 agonist, i.e., 5 µg of GLA-SE. The immunizations were three times at two weeks intervals. For the experiments in which these mice were challenged, challenge was at 14 days postimmunization. Specifically, they were challenged using 2,000 Type II (Me49-Fluc) parasites. These parasites were injected intraperitoneally.

ELISpot Assay to Determine Immune Responses with Murine Splenocytes. Mice were euthanized 14 days after immunization. Spleens were harvested as follows: Initially, they were pressed through a 70 µm screen. This allowed for formation of a suspension of single-cells. Erythrocytes were depleted from this suspension. AKC lysis buffer (160 mM NH$_4$Cl, 10 mM KHCO$_3$, 100 mM EDTA) was used to deplete the RBCs. Hank's Balanced Salt Solution (HBSS) was used to was splenocytes twice. Then they were resuspended. The medium used to resuspend them was RPMI-1640 supplemented with 2 mM L-GlutaMax. Murine splenocyte ELISPOT assays were performed as described earlier. This was done using anti-mouse IFN-γ mAb (AN18) and biotinylated anti-mouse IFN-γ mAb (R4-6A2). In each well, 2.5-5×10$^5$ splenocytes were plated. Mabtech (Cincinnati, OH) was the source of all of the antibodies and all of the reagents used to perform ELISPOT assays. A mimimum of 3 three replicate wells were used to plate cells for each condition, as we described earlier, to measure spot forming cells (SFCs) per 10$^6$ murine splenocytes.

Bioluminescence Imaging for Determining Outcomes of Challenge with Type II Parasites. We imaged mice infected with 2,000 Fluc tachyzoites of the Me49 strain of T. gondii. These mice were imaged 21 days after challenge. An in vivo imaging system (IVIS; Xenogen, Alameda, CA) allowed us to visualize luciferin injected retroorbitally interacting with luciferase in the parasites. These mice were anesthetized. Anesthesia was performed in an O$_2$-rich induction chamber with 2% isoflurane. Twelve minutes after receiving luciferin, imaging took place. Living image® 2.20.1 software (Xenogen) was used for assessment of photonic emissions. Pseudocolor representations of light intensity and mean photons/region of interest (ROI) represent parasite burden in the imaging. All these mouse experiments were replicated a minimum of two times as in our earlier work[23]. In each group we used five mice[23].

Enumeration of Cysts in Mouse Brains Following Type II Parasite Challenge. Mouse brains were collected at day 21. They were homogenized in 1 ml of saline (0.85% NaCl). 50 µl of the homogenate was the used to count tissue cysts, microscopically. Cyst count was then multiplied by 20. This product was then used to determine the number of tissue cysts per brain. This number was confirmed by staining brain cysts with fluorescein-labeled *Dolichos billorus* agglutinin (Vector Laboratories) and quantitation using fluorescence microscopy.

Statistical Analyses. Data were compared for each assay by ANOVA and a Student t test. GraphPad Prism 5 software (GraphPad Software, San Diego, CA) as described. Differences between the groups were identified by ANOVA and multiple comparison procedures, as we previously described. Means±SD are used to express data. A p value <0.05 was considered to be statistically significant for our results.

Example 3. Novel, Immunogenic, Self-Replicating RNA Nanoparticle, Platform Encoding Immunosense Designed *Toxoplasma* Peptides is a Vaccine that Protects HLA-A*1101 Transgenic Mice We designed and produced a self-replicating RNA nanoparticle displaying peptide epitopes that induces protective CD8$^+$ and CD4$^+$ T cells against T. gondii infection. These RNA replicons are composed of Venezuelan Equine Encephalitis (VEE) alphavirus backbone, 5 CD8+ HLA-A03-1101 supertype-restricted epitopes from antigens expressed during the life cycle of *Toxoplasma*, and a universal CD4$^+$ T cell epitope (PADRE). All are encapsulated in lipid nanoparticles and evaluated for their immunogenic and protective potential against T. gondii in HLA- A*1101 transgenic mice. Administered without the need for an adjuvant, the self-replicon nanoparticles elicit T cells producing IFN-γ and protect mice against parasite burden when challenged with type II T. gondii strain. Thus, this work demonstrates that RNA replicon nanoparticles can present selected antigenic epitopes that elicit CD8+ T cells that produce interferon y and thereby act as a powerful immunostimulatory protective vaccine.

Materials and Methods

RNA Synthesis

The DNA plasmid contains alphavirus RNA replication machinery genes encoding the self-amplifying RNA (pTK159) and our linked 5 HLA*A-1101 antigenic peptides plus PADRE is synthesized by GENEWIZ. The RNA sequence is as follow:

(SEQ ID NO: 29)
GAAUUUGCUGCGACGAUGGGUAUGCAAGUCCAGAUCCAGAGCCUGUUC

CUGCUGCUGCUGUGGGUGCCGGGUUCACGCGGUAUGGCGGUGGUUAGC

CUGCUGCGUCUGCUGAAAAACGCCAUGCUGACCGCAUUUUUCCUGCGC

AAUGCGGCCGCAAAGAGUUUCAAGGAUAUCCUGCCGAAAAAGGCUGCG

GCCAGCUCUGCGUAUGUCUUUUCCGUGAAAAAGGCAGCUGCGAAAUUC

GUUGCUGCCUGGACCCUGAAAGCUGCCGCUAAAUCGACGUUCUGGCCG

UGUCUGCUGCGU

The encoded sequence is:

(SEQ ID NO: 37)
EFAATMGMQVQIQSLFLLLLWVPGSRGMAVVSLLRLLKNAMLTAFFLR

NAAAKSFKDILPKKAAASSAYVFSVKKAAAKFVAAWTLKAAAKSTFWP

CLLR STOP.

Plasmids were amplified from *E. coli* and purified using Qiagen Plasmid Maxi kits (Qiagen). DNA is linearized by restriction enzyme digestion. Linearized DNA templates were transcribed into RNA and purified using MEGA script T7 kit (Life Technologies) and purified using lithium chloride (LiCl) procedures. The self-RNA replicating was then encapsulated with lipids using the Vaccinia Capping system (New England BioLabs) and purified by LiCl precipitation before formulation.

Mice

We used HLA-A*1101 transgenic mice that express a chimeric HLA-A*1101/H2-Db MHC Class I Molecule and are on a C57BL/6×Balb/C background backcrossed to study the 5 HLA-A*1101 peptides responses. They originally were produced at Pharmexa-Epimmune (San Diego, CA) and bred at the University of Chicago.

Protein Synthesis

5 HLA*A-1101 antigenic peptides plus PADRE were linked with the spacer sequences N/AAA (SEQ ID NO: 21). To make proteins, DNA was PCR-amplified and cloned in the expression vector pET-22 (Novagen). The multi-epitope protein was expressed in the *Escherichia coli* BL21-Codon-Plus strain (Stratagene). Proteins were purified using standard protocols.

Immunogencity of RNA Nanoparticles

To test the RNA nanoparticles, self-assembling RNA replicon encoding *Toxoplasma* immunogenic antigens and PADRE were evaluated for immunogenicity in mice. Purified RNA (1 µM) was injected intramuscularly, 50 µL in each quadriceps muscle, in mice as a prime and a boost. 10 days after the boost, spleens from immunized were harvested, pressed through a 70 µm screen to form a single-cell suspension, and depleted of erythrocytes with ACK lysis buffer (160 mM $NH_4Cl$, 10 mM $KHCO_3$, 100 µM EDTA). Splenocytes were then washed twice in PBS supplemented with 5% FBS (Atlanta Biologicals, Flowery Branch, GA), and resuspended in complete RPMI medium (RPMI-1640 supplemented with 2 mM L-GlutaMax (Life Technologies), 100 U/ml penicillin, 100 µg/ml streptomycin, 1 mM sodium pyruvate, 50 µM β-mercaptoethanol, and 10% FBS) before use in the ELISpot assay. To evaluate protective effects of RNA replicons in vivo, immunized HLA-A*1101 transgenic mice were challenged with 10,000 type II (Me49-Fluc) parasites and parasite burden quantitated as described previously(10).

Enzyme-Linked Immunospot (ELISpot) Assay

Multiscreen MSIPS4W10 HTS-IP filter 96-well plates (Millipore, Billerica, MA) were washed first with 35% ethanol for 1 min and incubated with 15 µg/ml α-mouse IFN-γ capture mAb (AN18; Mabtech, Cincinnati, OH) in sterile PBS overnight, and washed with sterile PBS. The plate was blocked with RPMI-1640 medium containing 10% FBS at room temperature for 2 hours. ~2-5×$10^5$ murine splenocytes were plated per well and incubated with CD8+ HLA-A03-11 supertypes restricted epitope peptides at 10 µg/ml for 48 hours at 37° C. Plates were then washed with sterile PBS and incubated with 1 ng/ml biotinylated α-mouse IFN-γ detection mAb (R4-6A2) for 2 hours at room temperature, washed with PBS, incubated with streptavidin-conjugated alkaline phosphatase at 1/1000 dilution for 1 hour at room temperature. Spots were developed using 5-bromo-4-chloro-3-indolyl-phosphate/p-nitro blue tetrazolium chloride (BCIP/NBT). The spots were counted using an automated ELISpot reader (CTL Immunospot).

Cyst Count in Mouse Brains Following Type II Parasite Challenge

Mice brains collected at day 21 were homogenized in saline and tissue cysts were counted in a mounted-slide using optical microscope. The cysts are confirmed with fluorescein-labeled *Dolichos biflorus* agglutinin (Vector Laboratories).

Statistical Analyses

Statistical analyses for all applicable assays were performed using a 2-tailed student's t-test.

Results

Development of RNA Replicons as a Platform for Peptides Delivery

We produced RNA replicons containing 5 linked CD8+ HLA-A03 supertypes restricted epitopes from highly immunogenic antigens described above and linked with N/AAA spacer with PADRE. The self-assembling RNA derived from an alphavirus genome contains the genes encoding the viral proteins required for RNA replication. The structural protein genes were replaced with our composite linked antigens eliciting protective $CD8^+$ and $CD4^+$ T cells. The size and RNA encapsulation were characterized. Encapsulation of RNA was determined by dynamic light scattering (data not shown). For this study, we tested 3 lipid nanoparticles (LNP); empty LNPs (without RNA), LNP-encapsulated RNA without *Toxoplasma* antigens (pTK159) to determine whether RNA encapsulation is necessary for efficient RNA delivery and reporter gene expression, LNPs with *Toxoplasma* insert (pTK 426)

Figure 13:
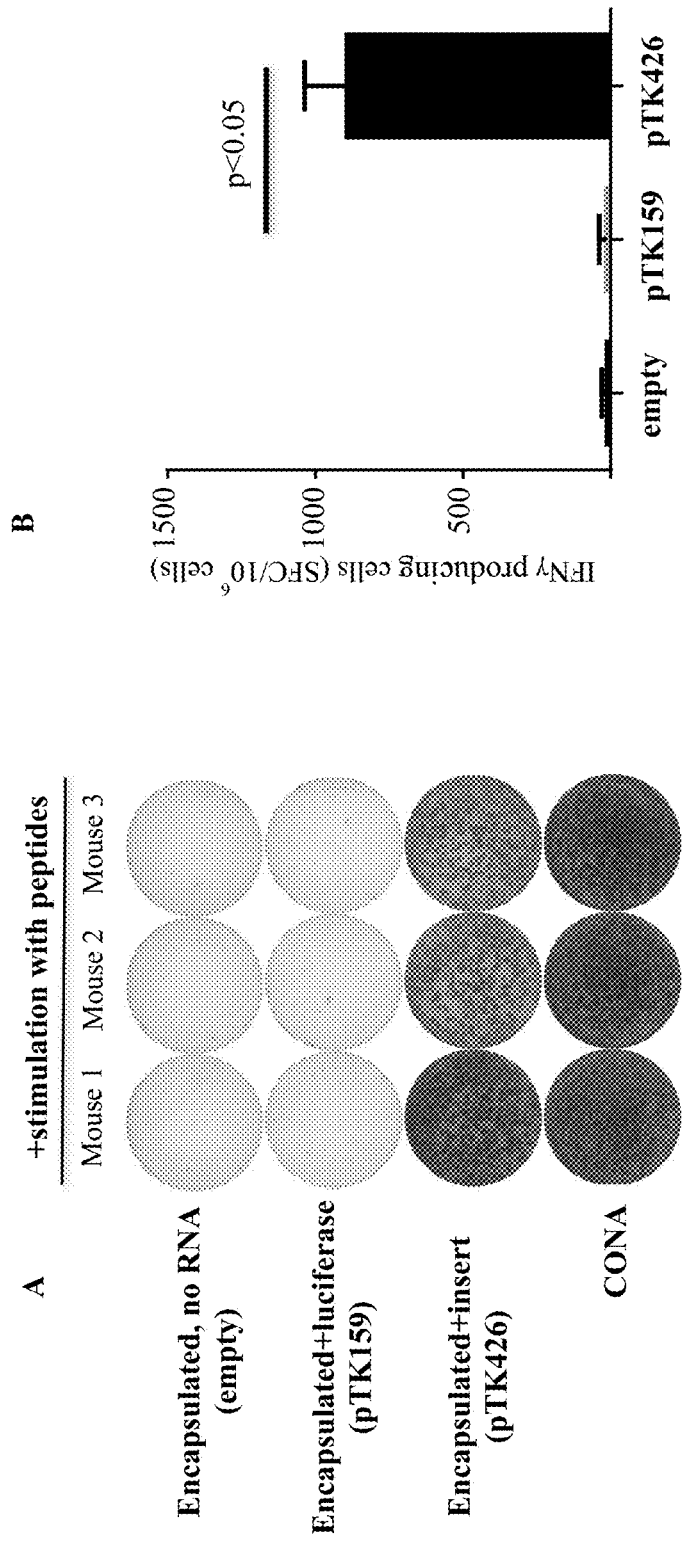
FIG. 13: (A) Immunization with replicon elicits CD8 T splenocytes that respond to the immunizing CD8 T cell elicity peptides. Interferon gamma elisspot shows that response. (B) Histogram showing amounts of interferon gamma produced by immunization with the Toxoplasma gondii sequence in the replicon. These immunizations were protective (data not shown).

RNA Replicons with HLA*A-1101-Restricted CD8+ T Cell Epitope Peptides Immunogenicity in Vitro HLA-A*1101 transgenic mice were immunized twice at intervals of three weeks with RNA replicons. Two weeks after the last immunization, the spleens were removed from immunized mice and the ability of splenocytes to produce IFN-γ upon stimulation with peptides or full-length protein was analyzed. Empty RNA and pTK159 were used as control. FIG. 13A indicates IFN-γ secretion was significantly enhanced by immunization with self-assembling RNA containing *Toxoplasma* insert and not with control RNAs when splenocytes were stimulated with either pool of HLA*A-1101-restricted CD8+ T cell epitope peptides or whole protein (FIG. 13B). These results demonstrate that HLA*A-1101-restricted CD8+ T cell epitopes and PADRE in this nanoparticle RNA vaccine delivers help of IFN-γ production.

Protective Immune Responses of Encapsulated Self-Assembling RNA Against Type II Strain in Mice HLA*A-1101 mice were immunized and challenged 2 weeks after the last immunization with type II (Me49 Fluc) parasites. A majority, 4 of 5 (80%) mice immunized with pTK426 survived parasite challenge. In contrast, only 2 of 5 (40%) immunized with empty RNA survived parasite challenge. Mice immunized with composite protein were less protected than mice immunized with self-assembling RNA.

Discussion

Herein, we present a novel way to present *Toxoplasma* immunogenic peptide epitopes to a host's immune system based on a self-assembling RNA replicon. This RNA is based on VEE alphavirus backbone. The RNA encodes for non-structural proteins, involved in RNA replication and insert of *T. gondii* peptides. The selection of peptides was based on previous studies that show these peptides elicited immuneresponse and activated T cell responses. All are encapsulated in lipid self-assembling RNA nanoparticles and used for vaccination. This approach showed to be safe and confered protection from type I allergy.

These RNA nanoparticles were evaluated for their efficacy in eliciting IFN-γ by HLA-A*1101 transgenic mice and for their protection against *Toxoplasma* challenge. This work demonstrates the feasibility of using this RNA platform for the delivery of potentially protective restricted by human major histocompatibilty (HLA) class I in our model HLA-A*1101 mice.

The self-amplifying RNA based on an alphavirus genome contains the genes encoding the alphavirus RNA replication machinery, and the genes encoding the parasite insert combines epitopes from *T. gondii* with this new methodlogy for RNA delivery. The genes encoding the antigen replaced the genes encoding the viral structural proteins that are highly expressed in the cytoplasm. Therefore it is important to have a system, which is driving the expression of antigens in this location. No live viral subunits were generated by the self-assembling of the viral nanoparticles. After immunization, replication and amplification of RNA leading to self-assembling of RNA occurs in the cytoplasm. Therefore, delivery barriers for the epitopes are excluded with this model. We found that these RNA particles are highly immunogenenic compared to the empty RNA or peptide with GLA adjuvant (data not shown). However, there is no protection against *Toxoplasma* type I strain (data not shown). Although the induction of interferon protection is robust, the protection against type II *T. gondii* is not complete. By using an adjuvant, perhaps even something like profiling encoded in the RNA, or inclusion of other epitopes that elicit helper T cells, or adding invasion blocking B cell epitopes, the efficacy of the RNA nanoparticle vaccine can be increased. It also will be of interest to our RNA replicon vaccines to add protective peptide epitopes responses for three HLA supermotifs, A02, A03 and B07 present in 90% of people and study responses in the supertype mice HLA-A*0201, HLA-A11*01, and HLA-B*0702.

Example 4. Protection and Harm from $CD4^+$ T Cell-Eliciting Vaccines

The role of $CD4^+$ T cells for the control of both acute and chronic *Toxoplasma* infection is relatively unexplored. Previous studies identified a protective role of $CD4^+$ T Cell-stimulating peptide, AS15 in C57BL/6 brain mice. Here, we show that a boost immunization of HLA-A*1101 mice with AS15 administered with GLA-SE adjuvant, robustly increase cytokines expression (IFN-γ, TNF α, and IL6) and leads to gut pathology. The mice that survived the cytokines storm confer robust protection against type I strain parasites. Introduction of $CD8^+$ T-cell stimulating *T. gondii* peptides or the universal $CD4^+$ helper T cell epitope, PADRE, in a vaccine formulation with adjuvanted AS15 suppress the necrosis and reduces IFN-γ production. Thus, these findings demonstrate quantitative and qualitative features of an effective *Toxoplasma*-specific $CD4^+$ T cell response that should be considered in the testing of the next generation of different vaccine designs against toxoplasmosis.

Materials and Methods

Peptides and Adjuvants

The $CD4^+$ T cell-stimulating peptide AS15 (AVEIHRPVPGTAPPS (SEQ ID NO: 20)), the universal human $CD4^+$ T cell eliciting epitope, PADRE (AKFVAAWTLKAAA (SEQ ID NO: 19)), the $CD8^+$ T cell-stimulating peptides GRA6 (AMLTAFFLR (SEQ ID NO: 18)), SAG1 (KSFKDILPK (SEQ ID NO: 16)), SAG2C (STFWPCLLR (SEQ ID NO: 14)), SPA (SSAYVFSVK (SEQ ID NO: 15)), SPA (AVVSLLRLLK (SEQ ID NO: 17)) were synthesized by Synthetic Biomolecules, San Diego at >90% purity in lyophilized form. The TLR4 agonist was a GLA-SE mimetic that was synthesized by the Infectious Diseases Research Institute (IDRI, Seattle, WA).

Analysis of Peptide Solubility

Peptides were dissolved in DMSO. Samples were centrifuged at 15,000 rpm at room temperature for 1 h. Supernatant concentrations were determined by measuring absorbance at 280 nm and by HPLC. The percentage solubility of the samples was calculated, although no detailed studies of optimal concentrations of peptides or adjuvant were performed herein.

ELISpot Assays

In order to measure the IFN-γ production spleen, ELISpot assays were performed. Mice were euthanized 7 to 14 days after immunization. Spleens were harvested, and depleted of erythrocytes with AKC lysis buffer (160 mM $NH_4Cl$, 10 mM $KHCO_3$, 100 M EDTA). Splenocytes were washed twice with Hank's Balanced Salt Solution (HBSS) and suspended in complete RPMI medium (RPMI-1640 supplemented with 2 mM L-GlutaMax [Invitrogen], 100 U/ml penicillin, 100 μg/ml streptomycin, 1 mM sodium pyruvate, 50 M -mercaptoethanol, and 10% FCS) before they were used in subsequent in vitro assays. Peptide concentration used for stimulation of splenocytes was 20 mg/ml. ELISpot assays with murine splenocytes were performed using a-mouse IFN-γ mAb (AN18) and biotinylated α-mouse IFN-γ mAb (R4-6A2) as the cytokine-specific capture antibodies. Antibodies were monoclonal antibodies. $5\times10^5$ splenocytes were plated per well.

Mice

Female HLA-A*1101 transgenic mice express a chimeric HLA-B07/H2-Db MHC Class I molecule, are on a C57BL/6×Balb/c background backcrossed through many generations and have been previously described [8, 12], which were produced at Pharmexa-Epimmune (San Diego, CA) and bred at the University of Chicago. All studies were conducted with the approval of the Institutional Animal Care and Use Committee at the University of Chicago.

Challenge Experiments

We infected the HLA-A11 mice with a type II strain (ME49) of *T. gondii*, which is most frequently associated with human toxoplasmosis. The HLA-A11 mice were inoculated subcutaneously at the base of the tail using a 30-gauge needle with the peptides described earlier. Control mice were injected with PBS. The mice were challenged intraperitonially with 2000 ME49 tachyzoites 10-14 days after the last immunization.

In Vivo Bioluminescence Imaging for Determining Outcomes of Challenge with Type II Parasites Mice infected with 2,000 Me49-FLUC tachyzoites were imaged 21 days post-challenge using the in vivo imaging system (IVIS; Xenogen, Alameda, CA). Mice were injected retroorbitally with 200 μl (15.4 mg/ml) of D-luciferin, anesthetized in an $O_2$-rich induction chamber with 2% isoflurane, and imaged after 12 minutes. Photonic emissions were assessed using Living image® 2.20.1 software (Xenogen). Data are presented as pseudocolor representations of light intensity and mean photons/region of interest (ROI). All mouse experiments were repeated at least twice.

Enumeration of Cysts in Mouse Brains Following Type II Parasite Challenge

Mice were euthanized at 21 days after infection with 10,000 of Me49-Fluc, and brains were collected, homogenized with 1 ml of saline (0.85% NaCl). Tissue cysts were counted microscopically in 50 μl of the homogenate, and the count was multiplied by 20 to obtain the number of tissue cysts per brain. This number was confirmed by staining brain cysts with fluorescein-labeled *Dolichos biflorus* agglutinin (Vector Laboratories) and quantitation using fluorescence microscopy.

Flow Cytometry.

Splenocytes were manually processed using 70 μm filters in DMEM media supplemented with 5% FCS and red blood cells were lysed with ACK lysis buffer. Cells were stained with CD3 APC (145-2C11), CD4 PE (GK1.5), CD8 PerCP (53-6.7), and CD44 AF780 (IM7), CD45RB FITC (C363.16A). All antibodies were purchased from eBioscience (San Diego, CA). Memory T cells were defined as CD44$^{hi}$CD45RB$^{lo}$. All flow cytometry data was collected on LSRII flow cytometer (BD Biosciences, San Jose, CA) and analyzed using FlowJo software 10.0 (Tree Star, Ashland, OR).

Statistical Analyses

Data for each assay were compared by One-way ANOVA or a Student t test using GraphPad Prism 5 software (GraphPad Software, San Diego, CA). Differences between the groups were identified by ANOVA and multiple comparison procedures, as we previously described [7]. Data are expressed as the means±SD. Results were considered to be statistically significant at p<0.05.

Results

CD4 T Cell-Stimulating Peptide, AS15 with the Adjuvant GLA-SE (Lipid TLR-4 Agonist) Resulted in an Increased IFN-γ Production.

Splenocytes were isolated from immunized HLA-A11 transgenic mice 24 hours after the second immunization. Their ability of lymphocytes to generate IFN-γ and proliferate in response to AS15 peptide was assessed using ELISpot assay. The data (not shown)indicate IFN-γ production by AS15 peptide stimulation in vitro was significantly enhanced in mice immunized with adjuvanted AS15 peptide compare to AS15 peptide alone.

AS15 with the Adjuvant GLA-SE Causes Storm of Cytokines Expression and T Cell Marker, Correlated with Serious Defects in HLA-A11 Transgenic Mice Pathology and Death.

There is a remarkable susceptibility of HLA-A11 transgenic mice to the immunization with AS15 plus GLA-SE. At day 3-4 post-boost immunization, a majority of mice died. To better understand the fate of these mice after second immunization and to avoid the loss of mice after second immunization, blood was collected and the cytokine levels in the sera were analyzed before and after 24 hours post immunization. There was a significant increase of the level of IFN-γ, TNF α, and IL6, in the sera of immunized mice. Because, a majority of these mice died at day 3-4 after boost-immunization, we examined at 24 h the cytokines levels in the serum.

GLA-SE was found to induce a strong Th1 response that includes initial induction of IL-12, which in turn stimulates IFN-γ production. To confirm that AS15 with the adjuvant GLA-SE treatment increased Th1 cytokine production and to understand how the immunogen was affecting the fate of mice, we measured serum levels of IFN-γ, IL-12p70, IL-2, IL-10, and IL-6 by a cytokine bead array at 24 hours before and after second immunization (data not shown). When AS15 combined to GLA-SE, there is a significant increase of the level of IFN-γ, tumor necrosis factor α, and interleukin 6 after 24 hours post-II immunization. We also evaluated whether weight loss and mortality in mice immunized with adjuvanted AS15 was associated with liver damage and/or damages in the gut during infection. Severe necrosis of the ilea, predominantly within the villi, was observed in treated mice. Using Caspase3 marker, we demonstrated the presence of apoptotic cells in small intestine region (data not shown). In contrast, the ileum of untreated mice has a normal distribution. This is correlated with increase of infiltration of CD3 T-Cell. Changes also occur in the liver of treated mice.

Surprisingly, 5 out of 13 mice which survive the storm reduce parasite burden when mice are infected with the virulent *Toxoplasma* type I. More interestingly, there is a difference between the sex of mice in response to the immunization by AS15 and adjuvant. Our results showed that male HLA-A11 transgenic mice are more resistant to the boost immunization. None of mice (15 mice tested) died and all are resistant against death after infection.

Addition of HLA-A11-Restricted CD8$^+$ T cell Epitope Peptides and/or PADRE Abrogates AS15 Phenotype.

Figure 14:
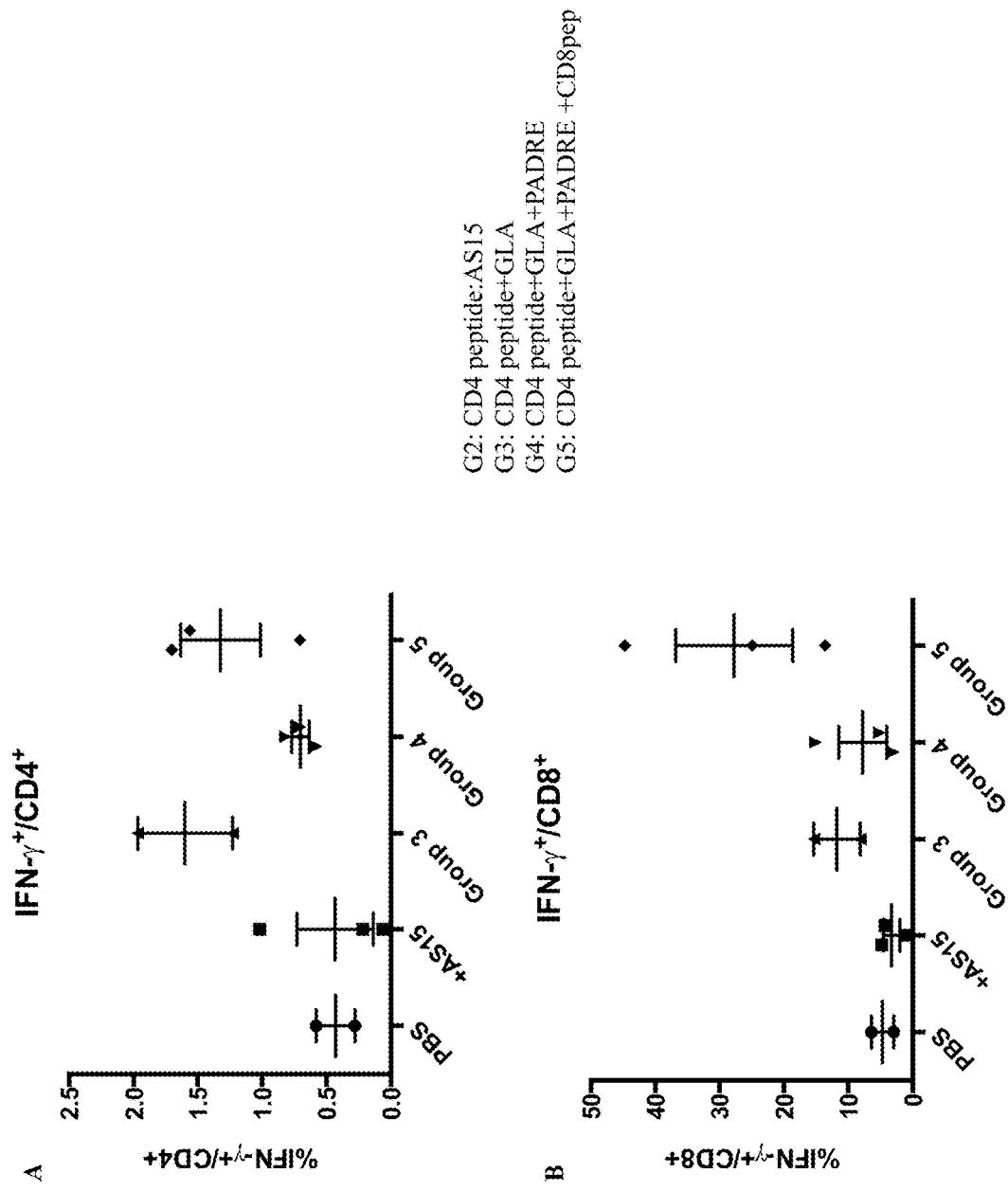
FIG. 14: Interferon gamma production by CD4 nd CD8 T cells. A. Interferon gamma production per CD4+T cell. Note that there is the most production in G3 CD4 peptide AS15 plus GLA-SE where when PADRE is present this is diminished. B. Interferon gamma production per CD8+ T cells. Note the group that contains CD9 peptides produces the most interferon gamma.

Since IFN-γ and CD8$^+$ T Cells have been shown to be critical for survival of mice after infection with *Toxoplasma*, we sought to combine AS15 peptide, PADRE and HLA-A11 restricted CD8$^+$ peptides for more increase of IFN-γ and better protection against *T. gondii*. As expected, immunization with AS15-GLA induced effective IFN-γ production from CD4 T cells (FIG. 14A). Surprisingly, when PADRE helper epitope was added to AS15 plus GLA, it reduces the amount of IFN-γ production. In other handwhen HLA A-11-restricted CD8$^+$ T cell epitope peptides from GRA6 (AMLTAFFLR (SEQ ID NO: 18)), SAG1 (KSFDILPK (SEQ ID NO:)), SAG2C (STFWPCLLR(SEQ ID NO: 14)), SPA (SSAYVFSVK (SEQ ID NO: 15)), SPA (AVVSLLRLLK (SEQ ID NO: 17)) were added, robust CD8$^+$ T cell production of IFN-γ was achieved (FIG. 14B).

PADRE Added to AS15 Plus GLA Protects Mice at Early Stage Against Type I and II Parasite Challenge.

Figure 15:
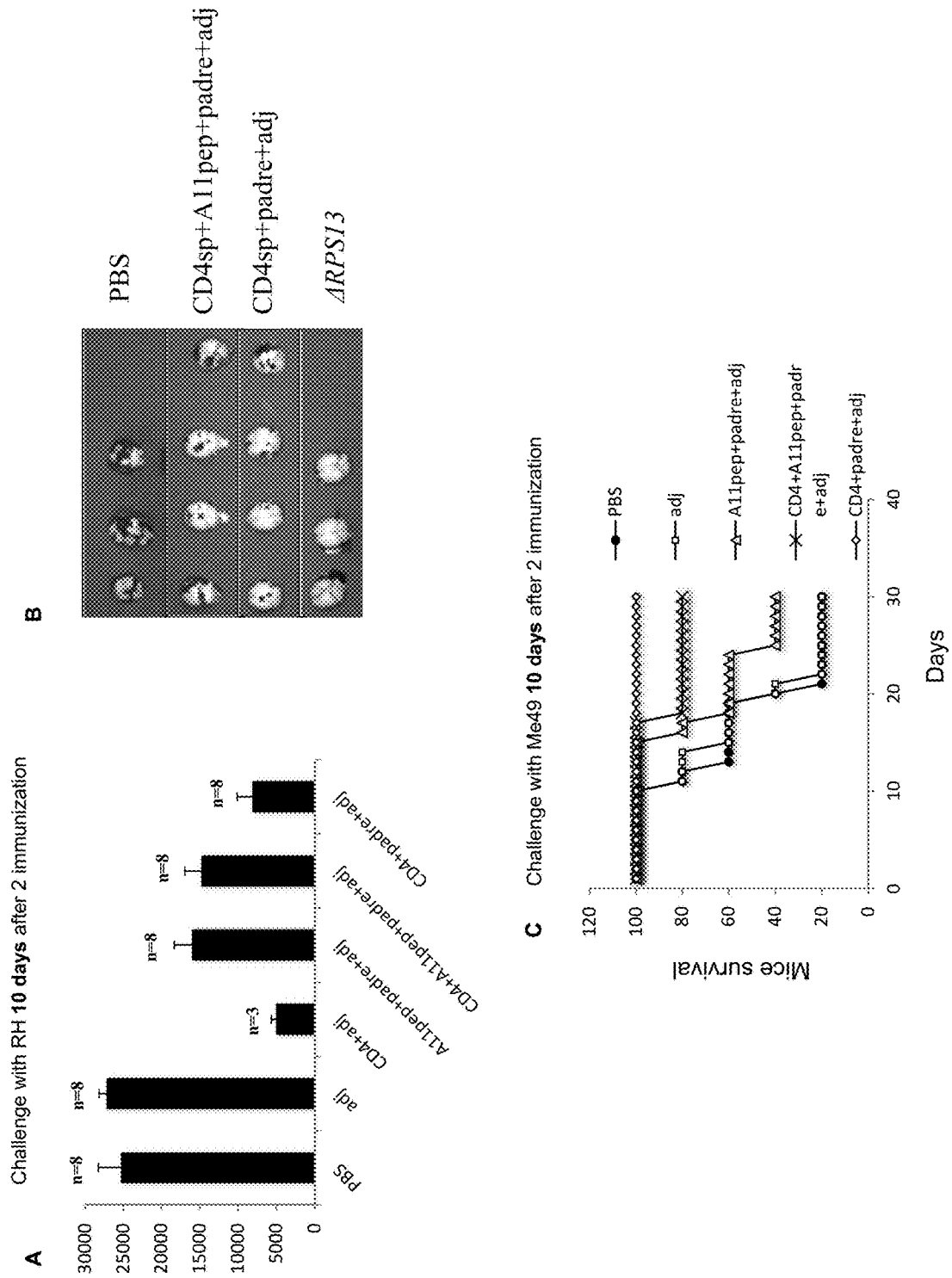
FIG. 15: Protection by immunization with AS15. A. AS15=CD4 plus adjuvant(GLA-SE) confers the greets protection measured as the least fluorescence by the RH tachyzoite challenge. B. Luminescence in brain. AS15 (CD4sp) protects against parasite burden luminescence. The live parasite that is attenuated , delta RPS13 is robustly protective as an internal control. All are significantly less than PBS control. C. Challenge with Me49 strain of *T. gondii*, 10 days after the second immunization. These mice have been immunized (or received PBS or adjuvant alone). The most robust protection was following immunization with AS15=CD4 peptide which is from *T. gondii* (diamonds and X).

We immunized twice HLA-A11 mice with AS15-GLA, AS15-GLA-PADRE, CD8$^+$ T cell restricted peptides-PADRE-GLA, AS15-CD8$^+$ T cell restricted peptides-PADRE. PBS or adjuvants alone were used as control. We challenged mice after 10 days with type I strain of *T. gondii* (2000 RH tachyzoites). Peritoneal fluid was collected 5 days post-infection and parasite fluorescence and numbers were measured using fluorometer and hemocytometer, respectively. Compared to control, fluorescence from all immunized mice was significantly lower (FIG. 15A). This reduction was also observed in the measurements of the total parasite burden (data not shown). Most interestingly, immunized mice with AS15-GLA (n=8 mice) show serious defects in growth and death 3 days after the second immunization, however adding PADRE abrogates this phenotype. The survived mice (n=3 mice) show the most protective protection against RH parasites. We decided to investigate in more details the response of mice to AS15-GLA and not include this group in our survival analysis with *T. gondii* type II strain.

We next addressed whether the combination of epitopes that were identified could confer protection against Me49 type II parasite challenge in HLA-A11 mice. Ten days after the second immunization, mice were challenged with 2000 Me49 (Fluc) that expresses the Firefly luciferase (FLUC) gene and imaged the brain at 21 days using the in vivo imaging system. As shown in FIG. 15B, the number of luciferase expressing parasites in the immunized HLA-A11 mice was significantly reduced compared to the unimmunized mice. The attenuated parasites by knockout of the ribosomal protein 13 gene (rps13Δ) were used as positive control. This correlates with survival studies shown in FIG. 15C, which shown a majority of mice immunized with the AS15-GLA-PADRE, AS15-CD8$^+$ T cell restricted peptides-PADRE-GLA survived parasite challenge. In contrast, only 1 of 5 (20%) unimmunized mice survived parasite challenge.

CD4$^+$ T cell and CD8$^+$ T Cell Response Deliver Respectively Protection Help at Early and Late Stage after Immunization.

Figure 16:
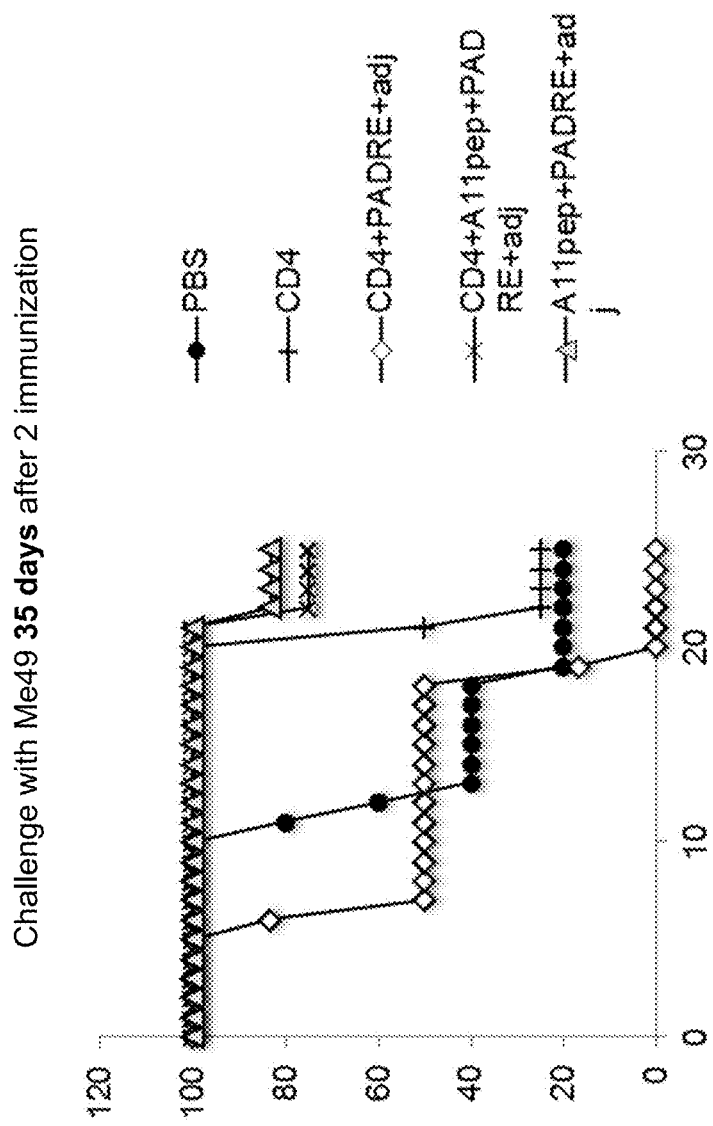
FIG. 16: HLA A-11-restricted CD8$^+$ T cell epitope peptides induce CD8+ Memory T cells.

The ability of AS15-GLA-PADRE and AS15-CD8$^+$ T cell restricted peptides-PADRE-GLA to protect mice against *T. gondii* was evaluated. Mice were immunized with same groups and were the subject of challenge after 10 or 35 days. As shown in FIG. 16, great protection after 35 days post immunization was observed when HLA-A11 mice CD8+ T cell restricted peptides were added. This is in contrast with the response of these peptides after 10 days post immunization (FIG. 15A).

PADRE has Better Outcome than AS15 Plus GLA When Added to CD8+ T Cell to Increase Memory CD8+ T Cell Response We then analyzed the effect of PADRE or AS15 added to CD8+ T cell peptides on the *T. gondii*—specific CD8+ T cell memory response. This was performed by quantifying the levels of memory T cells in the spleen from *T. gondii* immunized 35 days after the last immunization. CD8+ memory T cells was significantly increased with mice immunized with PADRE plus GLA- to CD8+ T cell peptides compared with the adjuvant alone or PBS (data not shown).

Discussion

We sought to combine AS15 peptide, PADRE and HLA A-11 restricted CD8+ peptides for more increase of IFN-γ and better protection against *T. gondii*. Our data show help from CD8+ T cell peptides for increase of IFN-γ expression. Interestingly, addition of PADRE, another restricted CD4+ T Cell to AS15 peptide reduces the increase of IFN-γ from CD4+ T Cell and abrogates AS15 phenotype.

We didn't see the presence of apoptotic cells or necrosis in liver and small intestine cells when PADRE was added. Furthermore, AS15 and PADRE seems playing a protective role immediately after boost immunization. However, CD8+ T cell peptides help to protect mice after long immunization period. This might be explained by the long lasting immune response and contribution of CD8+ T cell restricted peptides to increase memory CD8+ T Cell response. It is not clear why PADRE abrogates the AS15 phenotype. Two hypotheses might explain this role. PADRE might activate T regulatory cells (Treg) to reduce the response induced by AS15 or PADRE is competing with AS15 for T Cell stimulation. To rule out this possibility, we examined the PADRE and AS15 -specific CD4+ T cells generated for their expression of FoxP3, a marker for CD4+CD25+ T regulatory cells. We found that there is no difference in the expression of FoxP3 between the two groups, suggesting that the PADRE effect is not due to the activation of CD4+CD25+ T regulatory cells (data not shown). Furthermore, we examined the T cell stimulation generated by AS15 or AS15+PADRE for their expression to CD107a and b, a marker for cytotoxic T cells. We found that some mice from the group stimulated with AS15 presented high level of cd107a/b. This is in correlation with the variation found in this group.

Example 5

"Tox-All" is another example of a SAPN. Tox-all follows the same principle as the A11 SAPN (SEQ ID NO:27) but it has multiple components to stimulate diverse HLA haplotype CD8 T cells, CD4Tcells, B cells to make antibody, and contains the TLR5 ligand flagellin. These are included to stimulate multiple arms of the immune response. This is called "Tox-All" to reflect all the components. The sequence of Tox-All is:

(SEQ ID NO: 28)
(MGDDHHHHHHHHHH)WFMGVLVNSLQDITMGSLFFVQDFMIVSISLV
QDGLAAAVVAVQDLPQFATAATRDSPASGRYIQQMLDQRCQEIAAELC
QSGLRKMCVPSSRIVARNAVGITHQNTLQWRCFDTASLLESNQENNGV
NCVDDCGHTIPCPGGVHRQNSNHATRHEILSKLVEEGVQRFCSPYQAS
ANKYCNDKFPGTIARRSKGFGNNVEVAWRCYEKASLLYSVYAECASNC
GTTWYCPGGRRGTSTELDKRHYTEEEGIRQAIGSVDSPCSEVEVCLPK
DENPPLCLDESGQISRGSWEEWNARWDEWENDWNDWREDWQAWRDDWA
RWRATWMGGRLLSRLERLERRNEELRRLLQLIRHENRMVLQFVRALSM
QNAELERRLEELARGMAQVINTNSLSLLTQNNLNRSQSALGTAIERLS
SGLRINSARDDAAGQAIANRFTANIRGLTQASRNANDGISIAQTTEGA
LNEINNNLQRVRELAVQSANSTNSQSDLDSIQAEITQRLNEIDRVSGQ
TQFNGVRVLAQDNTLTIQVGANDGETIDIDLRQINSQTLGLDQLNVQQ
EYESDDAVVSLLRLLKNAMLTAFFLRNAAAKSFKDILPKKAAASSAYV
FSVKKAAAKFVAAWTLKAAAKSTFWPCLLRDSDSDTENPLQRIDAALA
QVDALRSDLGAVQNRFNSAITNLGNTVNNLSEARSRIEDSDYATEVSN
MSRAQILQQAGTSVLAQANQVPQNVLSLLR

Figure 17B:
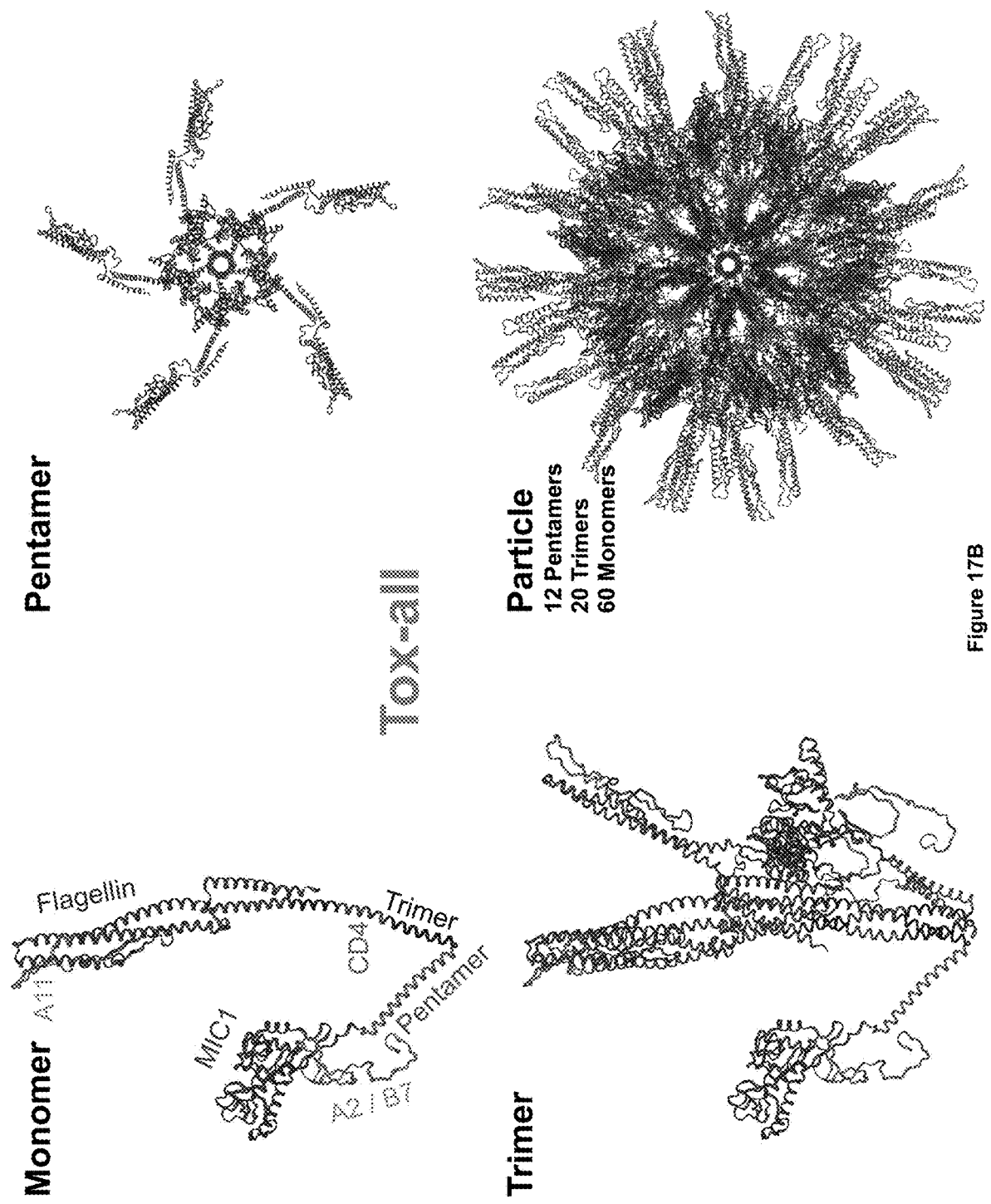
FIG. 17B: Schematic drawing of the ToxAll SAPN (SEQ ID NO:28) in monomeric, trimeric, pentameric, and particle form.
Figure 17C:
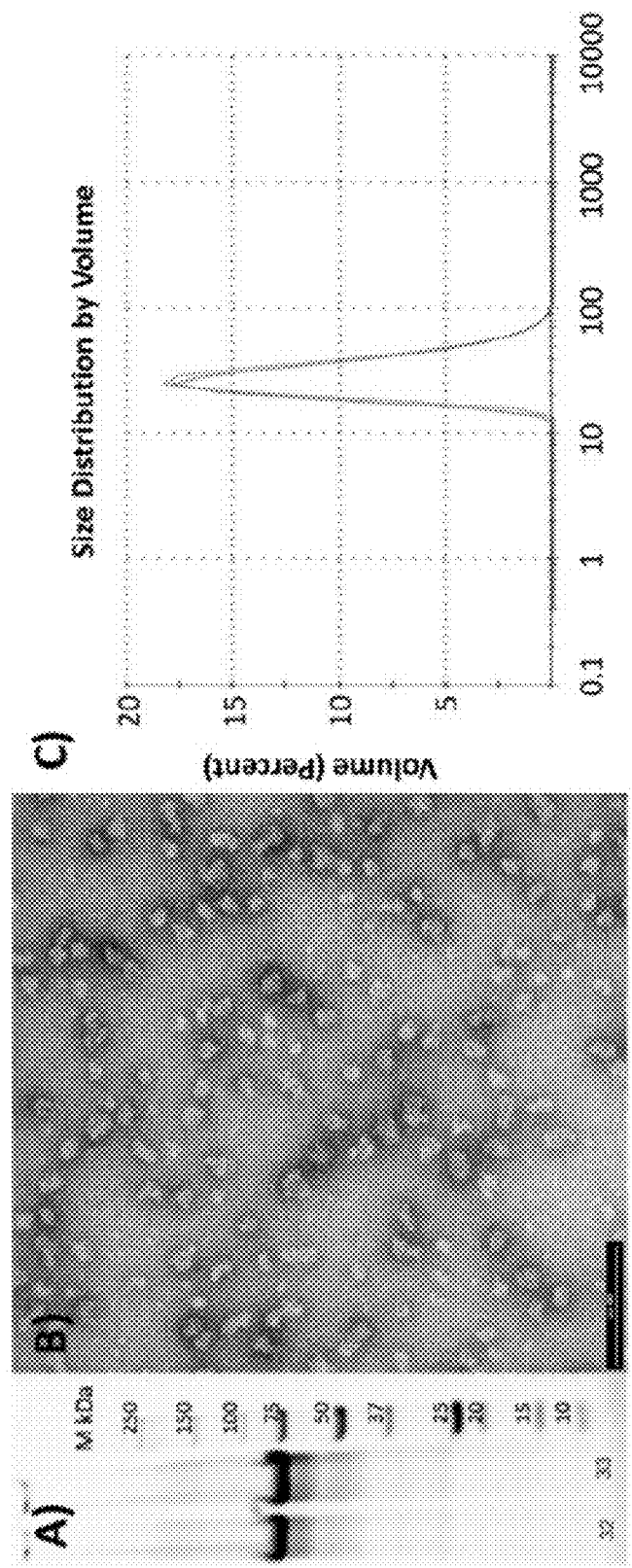
FIG. 17C: Predicted and actual proper folding and size of ToxAll. (A) Western blot; (B) Electron micrograph; (C) Size Distribution by volume.

The schematic diagrams of SAPN A11 (SEQ ID NO:27) in FIG. 17A 12e is similar to the schematic diagram of the more complex SAPN Tox-All (FIG. 17B). (FIG. 12f). FIG. 17C shows that this Tox-All has the proper size and folding and purity of the desired SAPN. Tox-All contains CD8 T cell eliciting epitopes by binding to HLA All, A2, and B7, PADRE a universal CD4 T cell eliciting epitope, protein domains that can elicit antibody (data not shown). Tox-All has the same scaffold flagellin that is shown for SAPN A11. Tox-All and the data provided demonstrate that we can produce and begin to build a multicomponent/epitope protein that stimulates an immune response in HLA A2 and HLA A11 mice and antibody, and a response to the CD4 epitope PADRE. It also contains the TLR5 adjuvant Flagellin and also stimulates TLR5 (data not shown). Additional CD8 peptides that bind to other HLA molecules to broaden population coverage and CD4 peptides can be added in this complex SAPN. Additional proteins that elicit B cells can also be included in the SAPN. This allows us to tailor an immune response for each component of the immune system we wish to stimulate. The methods and approaches are those described for the A11 SAPN.

SEQUENCE LISTING

<160> NUMBER OF SEQ ID NOS: 48

<210> SEQ ID NO 1
<211> LENGTH: 9
<212> TYPE: PRT
<213> ORGANISM: Artificial Sequence
<220> FEATURE:
<223> OTHER INFORMATION: Synthetic

<400> SEQUENCE: 1

Phe Leu Ser Leu Ser Leu Leu Val Ile
1               5

<210> SEQ ID NO 2
<211> LENGTH: 10
<212> TYPE: PRT
<213> ORGANISM: Artificial Sequence
<220> FEATURE:
<223> OTHER INFORMATION: Synthetic

<400> SEQUENCE: 2

Phe Met Ile Ala Phe Ile Ser Cys Phe Ala
1               5                   10

<210> SEQ ID NO 3
<211> LENGTH: 9
<212> TYPE: PRT
<213> ORGANISM: Artificial Sequence
<220> FEATURE:
<223> OTHER INFORMATION: Synthetic

<400> SEQUENCE: 3

Phe Val Ile Phe Ala Cys Asn Phe Val
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic

<400> SEQUENCE: 4

Phe Met Ile Val Ser Ile Ser Leu Val
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic

<400> SEQUENCE: 5

Phe Leu Leu Gly Leu Leu Val His Val
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic

<400> SEQUENCE: 6

Phe Leu Thr Asp Tyr Ile Pro Gly Ala
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic

```
<400> SEQUENCE: 7

Ile Thr Met Gly Ser Leu Phe Phe Val
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic

<400> SEQUENCE: 8

Gly Leu Ala Ala Ala Val Val Ala Val
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic

<400> SEQUENCE: 9

Val Leu Leu Pro Val Leu Phe Gly Val
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic

<400> SEQUENCE: 10

Phe Ala Ala Ala Phe Phe Pro Ala Val
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic

<400> SEQUENCE: 11

Val Val Phe Val Val Phe Met Gly Val
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic

<400> SEQUENCE: 12

Phe Met Gly Val Leu Val Asn Ser Leu
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic

<400> SEQUENCE: 13
```

```
Phe Leu Val Pro Phe Val Val Phe Leu
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic

<400> SEQUENCE: 14

Ser Thr Phe Trp Pro Cys Leu Leu Arg
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic

<400> SEQUENCE: 15

Ser Ser Ala Tyr Val Phe Ser Val Lys
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic

<400> SEQUENCE: 16

Lys Ser Phe Lys Asp Ile Leu Pro Lys
1               5

<210> SEQ ID NO 17
<211> LENGTH: 10
<212> TYPE: PRT
<213> ORGANISM: Artificial Sequence
<220> FEATURE:
<223> OTHER INFORMATION: Synthetic

<400> SEQUENCE: 17

Ala Val Val Ser Leu Leu Arg Leu Leu Lys
1               5                   10

<210> SEQ ID NO 18
<211> LENGTH: 9
<212> TYPE: PRT
<213> ORGANISM: Artificial Sequence
<220> FEATURE:
<223> OTHER INFORMATION: Synthetic

<400> SEQUENCE: 18

Ala Met Leu Thr Ala Phe Phe Leu Arg
1               5

<210> SEQ ID NO 19
<211> LENGTH: 13
<212> TYPE: PRT
<213> ORGANISM: Artificial Sequence
<220> FEATURE:
<223> OTHER INFORMATION: Synthetic

<400> SEQUENCE: 19
```

```
Ala Lys Phe Val Ala Ala Trp Thr Leu Lys Ala Ala Ala
1               5                   10
```

<210> SEQ ID NO 20
<211> LENGTH: 15
<212> TYPE: PRT
<213> ORGANISM: Artificial Sequence
<220> FEATURE:
<223> OTHER INFORMATION: Synthetic

<400> SEQUENCE: 20

```
Ala Val Glu Ile His Arg Pro Val Pro Gly Thr Ala Pro Pro Ser
1               5                   10                  15
```

<210> SEQ ID NO 21
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(4)
<223> OTHER INFORMATION: optionally absent

<400> SEQUENCE: 21

```
Asn Ala Ala Ala
1
```

<210> SEQ ID NO 22
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(4)
<223> OTHER INFORMATION: optionally absent

<400> SEQUENCE: 22

```
Lys Ala Ala Ala
1
```

<210> SEQ ID NO 23
<211> LENGTH: 5
<212> TYPE: PRT
<213> ORGANISM: Artificial Sequence
<220> FEATURE:
<223> OTHER INFORMATION: Synthetic

<400> SEQUENCE: 23

```
Gly Pro Gly Pro Gly
1               5
```

<210> SEQ ID NO 24
<211> LENGTH: 72
<212> TYPE: PRT
<213> ORGANISM: Artificial Sequence
<220> FEATURE:
<223> OTHER INFORMATION: Synthetic

<400> SEQUENCE: 24

```
Ala Val Val Ser Leu Leu Arg Leu Leu Lys Asn Ala Met Leu Thr Ala
1               5                   10                  15

Phe Phe Leu Arg Asn Ala Ala Lys Ser Phe Lys Asp Ile Leu Pro
            20                  25                  30
```

Lys Lys Ala Ala Ala Ser Ser Ala Tyr Val Phe Ser Val Lys Lys Ala
                35                  40                  45

Ala Ala Lys Phe Val Ala Ala Trp Thr Leu Lys Ala Ala Lys Ser
     50                  55                  60

Thr Phe Trp Pro Cys Leu Leu Arg
65                  70

<210> SEQ ID NO 25
<211> LENGTH: 37
<212> TYPE: PRT
<213> ORGANISM: Artificial Sequence
<220> FEATURE:
<223> OTHER INFORMATION: Synthetic

<400> SEQUENCE: 25

Trp Glu Glu Trp Asn Ala Arg Trp Asp Glu Trp Asn Asp Trp Asn
1               5                   10                  15

Asp Trp Arg Glu Asp Trp Gln Ala Trp Arg Asp Asp Trp Ala Arg Trp
                20                  25                  30

Arg Ala Thr Trp Met
            35

<210> SEQ ID NO 26
<211> LENGTH: 51
<212> TYPE: PRT
<213> ORGANISM: Artificial Sequence
<220> FEATURE:
<223> OTHER INFORMATION: Synthetic

<400> SEQUENCE: 26

Arg Leu Leu Ser Arg Leu Glu Arg Leu Glu Arg Arg Asn Glu Glu Leu
1               5                   10                  15

Arg Arg Leu Leu Gln Leu Ile Arg His Glu Asn Arg Met Val Leu Gln
                20                  25                  30

Phe Val Arg Ala Leu Ser Met Gln Asn Ala Glu Leu Glu Arg Arg Leu
            35                  40                  45

Glu Glu Leu
    50

<210> SEQ ID NO 27
<211> LENGTH: 466
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(14)
<223> OTHER INFORMATION: optionally absent

<400> SEQUENCE: 27

Met Gly Asp Lys His His His His His His His His Lys Asp
1               5                   10                  15

Gly Ser Asp Lys Gly Ser Trp Glu Glu Trp Asn Ala Arg Trp Asp Glu
                20                  25                  30

Trp Glu Asn Asp Trp Asn Asp Trp Arg Glu Asp Trp Gln Ala Trp Arg
            35                  40                  45

Asp Asp Trp Ala Arg Trp Arg Ala Thr Trp Met Gly Gly Arg Leu Leu
        50                  55                  60

Ser Arg Leu Glu Arg Leu Glu Arg Arg Asn Glu Glu Leu Arg Arg Leu
65                  70                  75                  80

```
Leu Gln Leu Ile Arg His Glu Asn Arg Met Val Gln Phe Val Arg
             85                  90                  95

Ala Leu Ser Met Gln Asn Ala Glu Leu Glu Arg Arg Leu Glu Glu Leu
        100                 105                 110

Ala Arg Gly Met Ala Gln Val Ile Asn Thr Asn Ser Leu Ser Leu Leu
        115                 120                 125

Thr Gln Asn Asn Leu Asn Arg Ser Gln Ser Ala Leu Gly Thr Ala Ile
        130                 135                 140

Glu Arg Leu Ser Ser Gly Leu Arg Ile Asn Ser Ala Arg Asp Asp Ala
145                 150                 155                 160

Ala Gly Gln Ala Ile Ala Asn Arg Phe Thr Ala Asn Ile Arg Gly Leu
                165                 170                 175

Thr Gln Ala Ser Arg Asn Ala Asn Asp Gly Ile Ser Ile Ala Gln Thr
        180                 185                 190

Thr Glu Gly Ala Leu Asn Glu Ile Asn Asn Asn Leu Gln Arg Val Arg
        195                 200                 205

Glu Leu Ala Val Gln Ser Ala Asn Ser Thr Asn Ser Gln Ser Asp Leu
210                 215                 220

Asp Ser Ile Gln Ala Glu Ile Thr Gln Arg Leu Asn Glu Ile Asp Arg
225                 230                 235                 240

Val Ser Gly Gln Thr Gln Phe Asn Gly Val Arg Val Leu Ala Gln Asp
                245                 250                 255

Asn Thr Leu Thr Ile Gln Val Gly Ala Asn Asp Gly Glu Thr Ile Asp
        260                 265                 270

Ile Asp Leu Arg Gln Ile Asn Ser Gln Thr Leu Gly Leu Asp Gln Leu
        275                 280                 285

Asn Val Gln Gln Glu Tyr Glu Ser Asp Asp Ala Val Val Ser Leu Leu
290                 295                 300

Arg Leu Leu Lys Asn Ala Met Leu Thr Ala Phe Phe Leu Arg Asn Ala
305                 310                 315                 320

Ala Ala Lys Ser Phe Lys Asp Ile Leu Pro Lys Lys Ala Ala Ser
                325                 330                 335

Ser Ala Tyr Val Phe Ser Val Lys Lys Ala Ala Lys Phe Val Ala
            340                 345                 350

Ala Trp Thr Leu Lys Ala Ala Lys Ser Thr Phe Trp Pro Cys Leu
            355                 360                 365

Leu Arg Asp Ser Asp Ser Asp Thr Glu Asn Pro Leu Gln Arg Ile Asp
        370                 375                 380

Ala Ala Leu Ala Gln Val Asp Ala Leu Arg Ser Asp Leu Gly Ala Val
385                 390                 395                 400

Gln Asn Arg Phe Asn Ser Ala Ile Thr Asn Leu Gly Asn Thr Val Asn
                405                 410                 415

Asn Leu Ser Glu Ala Arg Ser Arg Ile Glu Asp Ser Asp Tyr Ala Thr
        420                 425                 430

Glu Val Ser Asn Met Ser Arg Ala Gln Ile Leu Gln Gln Ala Gly Thr
        435                 440                 445

Ser Val Leu Ala Gln Ala Asn Gln Val Pro Gln Asn Val Leu Ser Leu
450                 455                 460

Leu Arg
465

<210> SEQ ID NO 28
<211> LENGTH: 748
<212> TYPE: PRT
```

<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(14)
<223> OTHER INFORMATION: optionally absent

<400> SEQUENCE: 28

```
Met Gly Asp Asp His His His His His His His His Trp Phe
1               5                   10                  15

Met Gly Val Leu Val Asn Ser Leu Gln Asp Ile Thr Met Gly Ser Leu
            20                  25                  30

Phe Phe Val Gln Asp Phe Met Ile Val Ser Ile Ser Leu Val Gln Asp
        35                  40                  45

Gly Leu Ala Ala Val Val Ala Val Gln Asp Leu Pro Gln Phe Ala
            50                  55                  60

Thr Ala Ala Thr Arg Asp Ser Pro Ala Ser Gly Arg Tyr Ile Gln Gln
65                  70                  75                  80

Met Leu Asp Gln Arg Cys Gln Glu Ile Ala Ala Glu Leu Cys Gln Ser
                85                  90                  95

Gly Leu Arg Lys Met Cys Val Pro Ser Ser Arg Ile Val Ala Arg Asn
            100                 105                 110

Ala Val Gly Ile Thr His Gln Asn Thr Leu Gln Trp Arg Cys Phe Asp
            115                 120                 125

Thr Ala Ser Leu Leu Glu Ser Asn Gln Glu Asn Asn Gly Val Asn Cys
130                 135                 140

Val Asp Asp Cys Gly His Thr Ile Pro Cys Pro Gly Val His Arg
145                 150                 155                 160

Gln Asn Ser Asn His Ala Thr Arg His Glu Ile Leu Ser Lys Leu Val
                165                 170                 175

Glu Glu Gly Val Gln Arg Phe Cys Ser Pro Tyr Gln Ala Ser Ala Asn
            180                 185                 190

Lys Tyr Cys Asn Asp Lys Phe Pro Gly Thr Ile Ala Arg Arg Ser Lys
        195                 200                 205

Gly Phe Gly Asn Asn Val Glu Val Ala Trp Arg Cys Tyr Glu Lys Ala
    210                 215                 220

Ser Leu Leu Tyr Ser Val Tyr Ala Glu Cys Ala Ser Asn Cys Gly Thr
225                 230                 235                 240

Thr Trp Tyr Cys Pro Gly Gly Arg Arg Gly Thr Ser Thr Glu Leu Asp
                245                 250                 255

Lys Arg His Tyr Thr Glu Glu Glu Gly Ile Arg Gln Ala Ile Gly Ser
            260                 265                 270

Val Asp Ser Pro Cys Ser Glu Val Glu Val Cys Leu Pro Lys Asp Glu
        275                 280                 285

Asn Pro Pro Leu Cys Leu Asp Glu Ser Gly Gln Ile Ser Arg Gly Ser
    290                 295                 300

Trp Glu Glu Trp Asn Ala Arg Trp Asp Glu Trp Asn Asp Trp Asn
305                 310                 315                 320

Asp Trp Arg Glu Asp Trp Gln Ala Trp Arg Asp Asp Trp Ala Arg Trp
                325                 330                 335

Arg Ala Thr Trp Met Gly Gly Arg Leu Leu Ser Arg Leu Glu Arg Leu
            340                 345                 350

Glu Arg Arg Asn Glu Glu Leu Arg Leu Leu Gln Leu Ile Arg His
        355                 360                 365
```

```
Glu Asn Arg Met Val Leu Gln Phe Val Arg Ala Leu Ser Met Gln Asn
        370                 375                 380

Ala Glu Leu Glu Arg Arg Leu Glu Glu Leu Ala Arg Gly Met Ala Gln
385                 390                 395                 400

Val Ile Asn Thr Asn Ser Leu Ser Leu Leu Thr Gln Asn Asn Leu Asn
                405                 410                 415

Arg Ser Gln Ser Ala Leu Gly Thr Ala Ile Glu Arg Leu Ser Ser Gly
            420                 425                 430

Leu Arg Ile Asn Ser Ala Arg Asp Asp Ala Ala Gly Gln Ala Ile Ala
        435                 440                 445

Asn Arg Phe Thr Ala Asn Ile Arg Gly Leu Thr Gln Ala Ser Arg Asn
450                 455                 460

Ala Asn Asp Gly Ile Ser Ile Ala Gln Thr Thr Glu Gly Ala Leu Asn
465                 470                 475                 480

Glu Ile Asn Asn Asn Leu Gln Arg Val Arg Glu Leu Ala Val Gln Ser
                485                 490                 495

Ala Asn Ser Thr Asn Ser Gln Ser Asp Leu Asp Ser Ile Gln Ala Glu
            500                 505                 510

Ile Thr Gln Arg Leu Asn Glu Ile Asp Arg Val Ser Gly Gln Thr Gln
        515                 520                 525

Phe Asn Gly Val Arg Val Leu Ala Gln Asp Asn Thr Leu Thr Ile Gln
530                 535                 540

Val Gly Ala Asn Asp Gly Glu Thr Ile Asp Ile Asp Leu Arg Gln Ile
545                 550                 555                 560

Asn Ser Gln Thr Leu Gly Leu Asp Gln Leu Asn Val Gln Gln Glu Tyr
                565                 570                 575

Glu Ser Asp Asp Ala Val Val Ser Leu Leu Arg Leu Leu Lys Asn Ala
            580                 585                 590

Met Leu Thr Ala Phe Phe Leu Arg Asn Ala Ala Ala Lys Ser Phe Lys
        595                 600                 605

Asp Ile Leu Pro Lys Lys Ala Ala Ala Ser Ser Ala Tyr Val Phe Ser
610                 615                 620

Val Lys Lys Ala Ala Ala Lys Phe Val Ala Ala Trp Thr Leu Lys Ala
625                 630                 635                 640

Ala Ala Lys Ser Thr Phe Trp Pro Cys Leu Leu Arg Asp Ser Asp Ser
                645                 650                 655

Asp Thr Glu Asn Pro Leu Gln Arg Ile Asp Ala Ala Leu Ala Gln Val
            660                 665                 670

Asp Ala Leu Arg Ser Asp Leu Gly Ala Val Gln Asn Arg Phe Asn Ser
        675                 680                 685

Ala Ile Thr Asn Leu Gly Asn Thr Val Asn Asn Leu Ser Glu Ala Arg
690                 695                 700

Ser Arg Ile Glu Asp Ser Asp Tyr Ala Thr Glu Val Ser Asn Met Ser
705                 710                 715                 720

Arg Ala Gln Ile Leu Gln Gln Ala Gly Thr Ser Val Leu Ala Gln Ala
                725                 730                 735

Asn Gln Val Pro Gln Asn Val Leu Ser Leu Leu Arg
            740                 745

<210> SEQ ID NO 29
<211> LENGTH: 300
<212> TYPE: RNA
<213> ORGANISM: Artificial Sequence
<220> FEATURE:
<223> OTHER INFORMATION: Synthetic
```

<400> SEQUENCE: 29

```
gaauuugcug cgacgauggg uaugcaaguc cagauccaga gccuguuccu gcugcugcug     60
ugggugccgg uucacgcgg uaggcggug guuagccugc ucgucugcu gaaaacgcc        120
```
```
gaauuugcug cgacgauggg uaugcaaguc cagauccaga gccuguuccu gcugcugcug     60
ugggugccgg uucacgcgg uauggcggug guuagccugc ugcgucugcu gaaaaacgcc    120
augcugaccg cauuuuuccu gcgcaaugcg ccgcaaaga guuucaagga uauccugccg    180
aaaaaggcug cggccagcuc ugcguaugac uuuccguga aaaaggcagc ugcgaaauuc    240
guugcugccu ggacccugaa agcugccgcu aaaucgacgu ucuggccgug ucugcugcgu    300
```

<210> SEQ ID NO 30
<211> LENGTH: 232
<212> TYPE: DNA
<213> ORGANISM: Artificial Sequence
<220> FEATURE:
<223> OTHER INFORMATION: Synthetic

<400> SEQUENCE: 30

```
catgggtatg caggtccaga ttcagtcact ctttctcctc ctcctctggg tccccggtag     60
ccggggtatg ccgtggtca gcctgctcag gctgctcaag aacgccatgc tgaccgcttt    120
ctttctcaga aatgccgctg caaagtcttt caaagacatc ctgcccaaga aagccgctgc    180
aagctccgcc tacgtgttca gtgtcaagaa agccgctgca aatttgtgg cc           232
```

<210> SEQ ID NO 31
<211> LENGTH: 16
<212> TYPE: PRT
<213> ORGANISM: Artificial Sequence
<220> FEATURE:
<223> OTHER INFORMATION: Synthetic

<400> SEQUENCE: 31

```
Asp Phe Leu Val Ile Tyr Ile Glu Glu Ala His Ala Ser Asp Gly Trp
1               5                   10                  15
```

<210> SEQ ID NO 32
<211> LENGTH: 12
<212> TYPE: PRT
<213> ORGANISM: Artificial Sequence
<220> FEATURE:
<223> OTHER INFORMATION: Synthetic

<400> SEQUENCE: 32

```
Ala Asp Phe Leu Tyr Ile Glu Ala His Asp Gly Trp
1               5                   10
```

<210> SEQ ID NO 33
<211> LENGTH: 20
<212> TYPE: PRT
<213> ORGANISM: Artificial Sequence
<220> FEATURE:
<223> OTHER INFORMATION: Synthetic

<400> SEQUENCE: 33

```
Gln Gly Pro Lys Glu Pro Phe Arg Asp Tyr Val Asp Arg Phe Tyr Lys
1               5                   10                  15

Thr Leu Arg Ala
            20
```

<210> SEQ ID NO 34
<211> LENGTH: 25
<212> TYPE: PRT
<213> ORGANISM: Artificial Sequence
<220> FEATURE:

<223> OTHER INFORMATION: Synthetic

<400> SEQUENCE: 34

His Met Lys Gln Leu Asp Val Glu Glu Leu Ser Asn Tyr His Leu Asn
1               5                   10                  15

Val Ala Arg Leu Lys Val Gly Glu Arg
            20                  25

<210> SEQ ID NO 35
<211> LENGTH: 33
<212> TYPE: PRT
<213> ORGANISM: Artificial Sequence
<220> FEATURE:
<223> OTHER INFORMATION: Synthetic

<400> SEQUENCE: 35

Gly Val Thr Gln Leu Met Arg Glu Met Leu Gln Leu Ile Lys Phe Gln
1               5                   10                  15

Phe Ser Leu Asn Tyr Gln Glu Glu Ser Leu Ser Tyr Gln Arg Leu Val
            20                  25                  30

Thr

<210> SEQ ID NO 36
<211> LENGTH: 72
<212> TYPE: PRT
<213> ORGANISM: Artificial Sequence
<220> FEATURE:
<223> OTHER INFORMATION: Synthetic

<400> SEQUENCE: 36

Ala Val Val Ser Leu Leu Arg Leu Leu Lys Asn Ala Met Leu Thr Ala
1               5                   10                  15

Phe Phe Leu Arg Asn Ala Ala Ala Lys Ser Phe Lys Asp Ile Leu Pro
            20                  25                  30

Lys Lys Ala Ala Ala Ser Ser Ala Tyr Val Phe Ser Val Lys Lys Ala
        35                  40                  45

Ala Ala Lys Phe Val Ala Ala Trp Thr Leu Lys Ala Ala Ala Lys Ser
    50                  55                  60

Thr Phe Trp Pro Cys Leu Leu Arg
65                  70

<210> SEQ ID NO 37
<211> LENGTH: 99
<212> TYPE: PRT
<213> ORGANISM: Artificial Sequence
<220> FEATURE:
<223> OTHER INFORMATION: Synthetic

<400> SEQUENCE: 37

Glu Phe Ala Ala Thr Met Gly Met Gln Val Gln Ile Gln Ser Leu Phe
1               5                   10                  15

Leu Leu Leu Leu Trp Val Pro Gly Ser Arg Gly Met Ala Val Val Ser
            20                  25                  30

Leu Leu Arg Leu Leu Lys Asn Ala Met Leu Thr Ala Phe Phe Leu Arg
        35                  40                  45

Asn Ala Ala Ala Lys Ser Phe Asp Ile Leu Pro Lys Lys Ala Ala Ala
    50                  55                  60

Ser Ser Ala Tyr Val Phe Ser Val Lys Lys Ala Ala Ala Lys Phe Val
65                  70                  75                  80

Ala Ala Trp Thr Leu Lys Ala Ala Ala Lys Ser Thr Phe Trp Pro Cys

```
                85                  90                  95

Leu Leu Arg

<210> SEQ ID NO 38
<211> LENGTH: 10
<212> TYPE: PRT
<213> ORGANISM: Artificial Sequence
<220> FEATURE:
<223> OTHER INFORMATION: Synthetic

<400> SEQUENCE: 38

Lys Tyr Lys Asp Gly Lys Gly Asp Asp Lys
1               5                   10

<210> SEQ ID NO 39
<211> LENGTH: 9
<212> TYPE: PRT
<213> ORGANISM: Artificial Sequence
<220> FEATURE:
<223> OTHER INFORMATION: Synthetic

<400> SEQUENCE: 39

Ile Arg Leu Leu Ala Ser Leu His His
1               5

<210> SEQ ID NO 40
<211> LENGTH: 9
<212> TYPE: PRT
<213> ORGANISM: Artificial Sequence
<220> FEATURE:
<223> OTHER INFORMATION: Synthetic

<400> SEQUENCE: 40

Leu Ile Arg Leu Leu Ala Ser Leu His
1               5

<210> SEQ ID NO 41
<211> LENGTH: 9
<212> TYPE: PRT
<213> ORGANISM: Artificial Sequence
<220> FEATURE:
<223> OTHER INFORMATION: Synthetic

<400> SEQUENCE: 41

Leu Thr Leu Gln Leu Ile Arg Leu Leu
1               5

<210> SEQ ID NO 42
<211> LENGTH: 8
<212> TYPE: PRT
<213> ORGANISM: Artificial Sequence
<220> FEATURE:
<223> OTHER INFORMATION: Synthetic

<400> SEQUENCE: 42

Val Ile Glu Glu Phe Asn Arg Ile
1               5

<210> SEQ ID NO 43
<211> LENGTH: 9
<212> TYPE: PRT
<213> ORGANISM: Artificial Sequence
<220> FEATURE:
<223> OTHER INFORMATION: Synthetic

<400> SEQUENCE: 43
```

```
Leu Gln Leu Ile Arg Leu Leu Ala Ser
1               5

<210> SEQ ID NO 44
<211> LENGTH: 9
<212> TYPE: PRT
<213> ORGANISM: Artificial Sequence
<220> FEATURE:
<223> OTHER INFORMATION: Synthetic

<400> SEQUENCE: 44

Ile Asp Val Val Ile Glu Glu Leu Phe
1               5

<210> SEQ ID NO 45
<211> LENGTH: 175
<212> TYPE: PRT
<213> ORGANISM: Artificial Sequence
<220> FEATURE:
<223> OTHER INFORMATION: Synthetic

<400> SEQUENCE: 45

Met Ala Gln Val Ile Asn Thr Asn Ser Leu Ser Leu Leu Thr Gln Asn
1               5                   10                  15

Asn Leu Asn Arg Ser Gln Ser Ala Leu Gly Thr Ala Ile Glu Arg Leu
            20                  25                  30

Ser Ser Gly Leu Arg Ile Asn Ser Ala Arg Asp Asp Ala Ala Gly Gln
        35                  40                  45

Ala Ile Ala Asn Arg Phe Thr Ala Asn Ile Arg Gly Leu Thr Gln Ala
    50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Leu Gln Arg Val Arg Glu Leu Ala
                85                  90                  95

Val Gln Ser Ala Asn Ser Thr Asn Ser Gln Ser Asp Leu Asp Ser Ile
            100                 105                 110

Gln Ala Glu Ile Thr Gln Arg Leu Asn Glu Ile Asp Arg Val Ser Gly
        115                 120                 125

Gln Thr Gln Phe Asn Gly Val Arg Val Leu Ala Gln Asp Asn Thr Leu
    130                 135                 140

Thr Ile Gln Val Gly Ala Asn Asp Gly Glu Thr Ile Asp Ile Asp Leu
145                 150                 155                 160

Arg Gln Ile Asn Ser Gln Thr Leu Gly Leu Asp Gln Leu Asn Val
                165                 170                 175

<210> SEQ ID NO 46
<211> LENGTH: 91
<212> TYPE: PRT
<213> ORGANISM: Artificial Sequence
<220> FEATURE:
<223> OTHER INFORMATION: Synthetic

<400> SEQUENCE: 46

Thr Glu Asn Pro Leu Gln Arg Ile Asp Ala Ala Leu Ala Gln Val Asp
1               5                   10                  15

Ala Leu Arg Ser Asp Leu Gly Ala Val Gln Asn Arg Phe Asn Ser Ala
            20                  25                  30

Ile Thr Asn Leu Gly Asn Thr Val Asn Leu Ser Glu Ala Arg Ser
        35                  40                  45

Arg Ile Glu Asp Ser Asp Tyr Ala Thr Glu Val Ser Asn Met Ser Arg
```

```
                50                  55                  60
Ala Gln Ile Leu Gln Gln Ala Gly Thr Ser Val Leu Ala Gln Ala Asn
 65                  70                  75                  80

Gln Val Pro Gln Asn Val Leu Ser Leu Leu Arg
                 85                  90

<210> SEQ ID NO 47
<211> LENGTH: 22
<212> TYPE: PRT
<213> ORGANISM: Artificial Sequence
<220> FEATURE:
<223> OTHER INFORMATION: Synthetic

<400> SEQUENCE: 47

Met Gly Met Gln Val Gln Ile Gln Ser Leu Phe Leu Leu Leu Leu Trp
 1               5                  10                  15

Val Pro Gly Ser Arg Gly
                 20

<210> SEQ ID NO 48
<211> LENGTH: 13
<212> TYPE: RNA
<213> ORGANISM: Artificial Sequence
<220> FEATURE:
<223> OTHER INFORMATION: Synthetic

<400> SEQUENCE: 48
gccgccrcca ugg                                                          13
```

We claim:

1. An isolated polynucleotide encoding a chimeric polypeptide, wherein the chimeric polypeptide comprises the amino acid sequence (SEQ ID NO: 24)
AVVSLLRLLKNAMLTAFFLRNAAAKSFKDILPKKAAASSAYVFSVKKA

AAKFVAAWTLKAAAKSTFWPCLLR.

2. The isolated polynucleotide of claim 1, wherein the chimeric polypeptide further comprises a further peptide domain comprising a peptide capable of promoting self-assembly/multimerization of the polypeptide.

3. The isolated polynucleotide of claim 2, wherein the further peptide domain comprises the sequence selected from the group consisting of:

(SEQ ID NO: 25)
WEEWNARWDEWENDWNDWREDWQAWRDDWARWRATWM;

(SEQ ID NO: 26)
RLLSRLERLERRNEELRRLLQLIRHENRMVLQFVRALSMQNAELERR

LEEL;

or both.

4. The isolated polynucleotide of claim 2, wherein the chimeric polypeptide comprises the amino acid sequence selected from the group consisting of SEQ ID NOS: 27-28 wherein residues in parentheses are optional and may be present or absent.

A11 (residues in parentheses are optional)

(SEQ ID NO: 27)
((MGDKHHHHHHHHHH))KDGSDKGSWEEWNARWDEWENDWNDWREDW

QAWRDDWARWRATWMGGRLLSRLERLERRNEELRRLLQLIRHENRMVL

QFVRALSMQNAELERRLEELARGMAQVINTNSLSLLTQNNLNRSQSAL

GTAIERLSSGLRINSARDDAAGQAIANRFTANIRGLTQASRNANDGIS

IAQTTEGALNEINNNLQRVRELAVQSANSTNSQSDLDSIQAEITQRLN

EIDRVSGQTQFNGVRVLAQDNTLTIQVGANDGETIDIDLRQINSQTLG

LDQLNVQQEYESDDA*VVSLLRLLK*NAMLTAFFLRNAAAKSFKDILPKK

AAA*SSAYVFSVK*KAAA*KFVAAWTLK*AAAKSTFWPCLLRDSDSDTENPL

QRIDAALAQVDALRSDLGAVQNRFNSAITNLGNTVNNLSEARSRIEDS

DYATEVSNMSRAQILQQAGTSVLAQANQVPQNVLSLLR

Tox-all (residues in parentheses are optional)

(SEQ ID NO: 28)
(MGDDHHHHHHHHHH)

WFMGVLVNSLQDITMGSLFFVQDFMIVSISLVQDGLAAAVVAVQDLPQ

FATAATRDSPASGRYIQQMLDQRCQEIAAELCQSGLRKMCVPSSRIVA

RNAVGITHQNTLQWRCFDTASLLESNQENNGVNCVDDCGHTIPCPGGV

HRQNSNHATRHEILSKLVEEGVQRFCSPYQASANKYCNDKFPGTIARR

-continued

```
SKGFGNNVEVAWRCYEKASLLYSVYAECASNCGTTWYCPGGRRGTSTE

LDKRHYTEEEGIRQAIGSVDSPCSEVEVCLPKDENPPLCLDESGQISR

GSWEEWNARWDEWENDWNDWREDWQAWRDDWARWRATWMGGRLLSRLE

RLERRNEELRRLLQLIRHENRMVLQFVRALSMQNAELERRLEELARGM

AQVINTNSLSLLTQNNLNRSQSALGTAIERLSSGLRINSARDDAAGQA

IANRFTANIRGLTQASRNANDGISIAQTTEGALNEINNNLQRVRELAV

QSANSTNSQSDLDSIQAEITQRLNEIDRVSGQTQFNGVRVLAQDNTLT

IQVGANDGETIDIDLRQINSQTLGLDQLNVQQEYESDDAVVSLLRLLK

NAMLTAFFLRNAAAKSFKDILPKKAAASSAYVFSVKKAAAKFVAAWTL

KAAAKSTFWPCLLRDSDSDTENPLQRIDAALAQVDALRSDLGAVQNRF
```

-continued

```
NSAITNLGNTVNNLSEARSRIEDSDYATEVSNMSRAQILQQAGTSVLA

QANQVPQNVLSLLR.
```

5. The isolated polynucleotide of claim 1, wherein the chimeric polypeptide further comprises a secretory signal.

6. The isolated polynucleotide of claim 5, wherein the secretory signal is present at the N-terminus of the chimeric polypeptide.

7. A recombinant expression vector, comprising the isolated polynucleotide of claim 1 operatively linked to a control sequence.

8. A pharmaceutical composition, comprising:
  (a) the isolated polynucleotide encoding a chimeric polypeptide of claim 1; and
  (b) a pharmaceutically acceptable carrier.

9. The pharmaceutical composition of claim 8, wherein the composition comprises an adjuvant.

\* \* \* \* \*